(12) United States Patent
Lee et al.

(10) Patent No.: US 12,297,480 B2
(45) Date of Patent: May 13, 2025

(54) METHODS FOR PRODUCING DESIGNER ESTERS AND ASSESSING ALCOHOL ACYLTRANSFERASE SPECIFICITY FOR ESTER BIOSYNTHESIS

(71) Applicant: UNIVERSITY OF TENNESSEE RESEARCH FOUNDATION, Knoxville, TN (US)

(72) Inventors: Jong-Won Lee, Knoxville, TN (US); Cong T. Trinh, Knoxville, TN (US)

( * ) Notice: Subject to any disclaimer, the term of this patent is extended or adjusted under 35 U.S.C. 154(b) by 0 days.

(21) Appl. No.: 17/822,547

(22) Filed: Aug. 26, 2022

(65) Prior Publication Data
US 2023/0235368 A1  Jul. 27, 2023

Related U.S. Application Data

(60) Provisional application No. 63/260,654, filed on Aug. 27, 2021.

(51) Int. Cl.
*C12P 7/62* (2022.01)
*C12N 15/10* (2006.01)
*C12N 15/52* (2006.01)

(52) U.S. Cl.
CPC ............ *C12P 7/62* (2013.01); *C12N 15/1058* (2013.01); *C12N 15/1089* (2013.01); *C12N 15/52* (2013.01); *C12Y 101/01* (2013.01); *C12Y 102/0101* (2013.01); *C12Y 102/04001* (2013.01); *C12Y 203/01009* (2013.01); *C12Y 203/01075* (2013.01)

(58) Field of Classification Search
None
See application file for complete search history.

(56) References Cited

U.S. PATENT DOCUMENTS

2015/0376655 A1* 12/2015 Lee .................... C12N 15/52
435/160

OTHER PUBLICATIONS

Accession P76461. Nov. 1, 1997 (Year: 1997).*
Accession P52041. Oct. 1, 1996 (Year: 1996).*
Accession P52046. Oct. 1, 1996 (Year: 1996).*
Accession Q73Q47. Mar. 29, 2005. (Year: 2005).*
Accession P06672. Jan. 1, 1988 (Year: 1988).*
Accession PODJA2. Dec. 14, 2011 (Year: 2011).*
Accession O13437. May 18, 2010 (Year: 2010).*
Accession P40353. Feb. 1, 1995 (Year: 1995).*
Chica et al. Curr Opin Biotechnol. Aug. 2005;16(4):378-84. (Year: 2005).*
Singh et al. Curr Protein Pept Sci. 2017, 18, 1-11 (Year: 2017).*
Atsumi et al., Metabolic engineering of *Escherichia coli* for 1-butanol production. Metabolic Engineering, Nov. 2008, pp. 305-311, vol. 10 Issue 6.
Bond-Watts et al., Enzyme mechanism as a kinetic control element for designing synthetic biofuel pathways, Nature Chemical Biology, Apr. 2011, pp. 222-227, vol. 7 Issue 4.
Lee et al., Towards renewable flavors, fragrances, and beyond. Curr Opin Biotechnol, Feb. 2020, pp. 168-180, vol. 61.
Seo et al., Single mutation at a highly conserved region of chloramphenicol acetyltransferase enables isobutyl acetate production directly from cellulose by Clostridium thermocellum at elevated temperatures, Biotechnology for Biofuels, Oct. 15, 2019, vol. 12.
Seo et al., Engineering promiscuity of chloramphenicol acetyltransferase for microbial designer ester biosynthesis, Metab Eng, Jul. 2021, pp. 179-190, vol. 66.
Shen et al., Driving Forces enable high-titer anaerobic 1-butanol synthesis in *Escherichia coli*, Appl. Environ. Microbiol, May 2011, pp. 2905-2915, vol. 77 Issue 9.
Trinh et al., Rational design of efficient modular cells, Metabolic engineering, Nov. 2015, pp. 220-231, vol. 32.
Trinh et al., Minimal *Escherichia coli* cell for the most efficient production of ethanol from hexoses and pentoses, Applied and Environmental Microbiology, Jun. 2008, pp. 3634-3643, vol. 74 Issue 12.
Waugh, The remarkable solubility-enhancing power of *Escherichia coli* maltose-binding protein, Postepy Biochem, 2016, pp. 377-382, vol. 62 Issue 3.
Wilbanks et al., A Prototype for Modular Cell Engineering, ACS Synthetic Biology, 2018, pp. 187-199, vol. 7 Issue 1.

* cited by examiner

*Primary Examiner* — Christian L Fronda

(74) *Attorney, Agent, or Firm* — FisherBroyles, LLP; Susan M. Oiler

(57) ABSTRACT

Methods of microbial screening for identifying alcohol acyltransferases for ester biosynthesis and submodules for ester pathways to produce butyryl-coenzyme A derived esters are disclosed. The method includes the introduction preselected plasmids into a respective host strain to form engineered microbes, in situ fermentation thereof followed by a colorimetric assay for quantification of production of the target ester. In situ fermentation includes inoculating each well of a microplate that have a culture media for producing target esters with one of the engineered microbes, adding an overlay of a solvent to each, and incubating the same. The colorimetric assay includes transfer of a quantity of the overlay from each well to respective clean wells of a new microplate, treatment of each well to form an iron-hydroxamic acid complex aqueous phase, centrifugation of the microplate, and measurement of the absorbance at 520 nm and comparison to a standard curve for the target ester.

13 Claims, 26 Drawing Sheets

Specification includes a Sequence Listing.

FIG. 12

| Strains | Plasmid 1 | Plasmid 2 |
|---|---|---|
| EcJWBA1 | pACYCD $P_{T7lac}$::atoB$_{Ec}$::hbd$_{Ca}$::crt$_{Ca}$-$P_{T7lac}$::ter$_{Td}$ | pETD $P_{T7lac}$::adhE2$_{Ca}$::fdh$_{Cb}$-$P_{T7lac}$::ATF1$_{Sc}$ |
| EcJWBA2 | pACYCD $P_{T7lac}$::atoB$_{Ec}$::hbd$_{Ca}$::crt$_{Ca}$-$P_{T7lac}$::ter$_{Td}$ | pRSFD $P_{T7lac}$::adhE2$_{Ca}$::fdh$_{Cb}$-$P_{T7lac}$::ATF1$_{Sc}$ |
| EcJWBA3 | pETD $P_{T7lac}$::atoB$_{Ec}$::hbd$_{Ca}$::crt$_{Ca}$-$P_{T7lac}$::ter$_{Td}$ | pACYCD $P_{T7lac}$::adhE2$_{Ca}$::fdh$_{Cb}$-$P_{T7lac}$::ATF1$_{Sc}$ |
| EcJWBA4 | pETD $P_{T7lac}$::atoB$_{Ec}$::hbd$_{Ca}$::crt$_{Ca}$-$P_{T7lac}$::ter$_{Td}$ | pRSFD $P_{T7lac}$::adhE2$_{Ca}$::fdh$_{Cb}$-$P_{T7lac}$::ATF1$_{Sc}$ |
| EcJWBA5 | pRSFD $P_{T7lac}$::atoB$_{Ec}$::hbd$_{Ca}$::crt$_{Ca}$-$P_{T7lac}$::ter$_{Td}$ | pACYCD $P_{T7lac}$::adhE2$_{Ca}$::fdh$_{Cb}$-$P_{T7lac}$::ATF1$_{Sc}$ |
| EcJWBA6 | pRSFD $P_{T7lac}$::atoB$_{Ec}$::hbd$_{Ca}$::crt$_{Ca}$-$P_{T7lac}$::ter$_{Td}$ | pETD $P_{T7lac}$::adhE2$_{Ca}$::fdh$_{Cb}$-$P_{T7lac}$::ATF1$_{Sc}$ |
| EcJWBA7 | pACYCD $P_{T7lac}$::atoB$_{Ec}$::hbd$_{Ca}$::crt$_{Ca}$-$P_{T7lac}$::ter$_{Td}$ | pRSFD $P_{T7lac}$::adhE2$_{Ca}$::fdh$_{Cb}$-$P_{T7lac}$::ATF1$_{Sc}^{opt}$ |
| EcJWBA8 | pACYCD $P_{T7lac}$::atoB$_{Ec}$::hbd$_{Ca}$::crt$_{Ca}$-$P_{T7lac}$::ter$_{Td}$ | pRSFD $P_{T7lac}$::adhE2$_{Ca}$::fdh$_{Cb}$-$P_{T7lac}$::malE_ATF1$_{Sc}^{opt}$ |
| EcJWBA9 | pACYCD $P_{T7lac}$::atoB$_{Ec}$::hbd$_{Ca}$::crt$_{Ca}$-$P_{T7lac}$::ter$_{Td}$ | pRSFD $P_{T7lac}$::adhE2$_{Ca}$::fdh$_{Cb}$-$P_{T7lac}$::nusA_ATF1$_{Sc}^{opt}$ |
| EcJWBA10 | pACYCD $P_{T7lac}$::atoB$_{Ec}$::hbd$_{Ca}$::crt$_{Ca}$-$P_{T7lac}$::ter$_{Td}$ | pRSFD $P_{T7lac}$::adhE2$_{Ca}$::fdh$_{Cb}$-$P_{T7lac}$::trxA_ATF1$_{Sc}^{opt}$ |
| EcJWBA11 | pACYCD $P_{T7lac}$::atoB$_{Ec}$::hbd$_{Ca}$::crt$_{Ca}$-$P_{T7lac}$::ter$_{Td}$ | pRSFD $P_{T7lac}$::adhE2$_{Ca}^{opt}$::fdh$_{Cb}$-$P_{T7lac}$::trxA_ATF1$_{Sc}^{opt}$ |
| EcJWBA12 | pACYCD $P_{T7lac}$::atoB$_{Ec}$::hbd$_{Ca}$::crt$_{Ca}$-$P_{T7lac}$::ter$_{Td}$ | pRSFD $P_{T7lac}$::malE_adhE2$_{Ca}^{opt}$::fdh$_{Cb}$-$P_{T7lac}$::trxA_ATF1$_{Sc}^{opt}$ |
| EcJWBA13 | pACYCD $P_{T7lac}$::atoB$_{Ec}$::hbd$_{Ca}$::crt$_{Ca}$-$P_{T7lac}$::ter$_{Td}$ | pRSFD $P_{T7lac}$::nusA_adhE2$_{Ca}^{opt}$::fdh$_{Cb}$-$P_{T7lac}$::trxA_ATF1$_{Sc}^{opt}$ |
| EcJWBA14 | pACYCD $P_{T7lac}$::atoB$_{Ec}$::hbd$_{Ca}$::crt$_{Ca}$-$P_{T7lac}$::ter$_{Td}$ | pRSFD $P_{T7lac}$::trxA_adhE2$_{Ca}^{opt}$::fdh$_{Cb}$-$P_{T7lac}$::trxA_ATF1$_{Sc}^{opt}$ |
| EcJWBA15 | pACYCD $P_{T7lac}$::atoB$_{Ec}$::hbd$_{Ca}$::crt$_{Ca}$-$P_{T7lac}$::ter$_{Td}$ | pRSFD $P_{T7lac}$::trxA_adhE2$_{Ca}^{opt}$::fdh$_{Cb}$-$P_{T7lac}$::trxA_ATF1$_{Sc}^{opt}$ |
| EcJWEB1 | pACYCD $P_{T7lac}$::atoB$_{Ec}$::hbd$_{Ca}$::crt$_{Ca}$-$P_{T7lac}$::ter$_{Td}$ | pETD $P_{T7lac}$::pdc$_{Zm}$::adhB$_{Zm}$::fdh$_{Cb}$-$P_{T7lac}$::SAAT$_{Fa}$ |
| EcJWEB2 | pACYCD $P_{T7lac}$::atoB$_{Ec}$::hbd$_{Ca}$::crt$_{Ca}$-$P_{T7lac}$::ter$_{Td}$ | pRSFD $P_{T7lac}$::pdc$_{Zm}$::adhB$_{Zm}$::fdh$_{Cb}$-$P_{T7lac}$::SAAT$_{Fa}$ |
| EcJWEB3 | pETD $P_{T7lac}$::atoB$_{Ec}$::hbd$_{Ca}$::crt$_{Ca}$-$P_{T7lac}$::ter$_{Td}$ | pACYCD $P_{T7lac}$::pdc$_{Zm}$::adhB$_{Zm}$::fdh$_{Cb}$-$P_{T7lac}$::SAAT$_{Fa}$ |
| EcJWEB4 | pETD $P_{T7lac}$::atoB$_{Ec}$::hbd$_{Ca}$::crt$_{Ca}$-$P_{T7lac}$::ter$_{Td}$ | pRSFD $P_{T7lac}$::pdc$_{Zm}$::adhB$_{Zm}$::fdh$_{Cb}$-$P_{T7lac}$::SAAT$_{Fa}$ |
| EcJWEB5 | pRSFD $P_{T7lac}$::atoB$_{Ec}$::hbd$_{Ca}$::crt$_{Ca}$-$P_{T7lac}$::ter$_{Td}$ | pACYCD $P_{T7lac}$::pdc$_{Zm}$::adhB$_{Zm}$::fdh$_{Cb}$-$P_{T7lac}$::SAAT$_{Fa}$ |

FIG. 12 Continuation

| Strains | Plasmid 1 | Plasmid 2 |
|---|---|---|
| EcJWEB6 | pRSFD $P_{T7lac}$::atoB$_{Ec}$::hbd$_{Ca}$::crt$_{Ca}$-$P_{T7lac}$::ter$_{Td}$ | pETD $P_{T7lac}$::pdc$_{Zm}$::adhB$_{Zm}$::fdh$_{Cb}$-$P_{T7lac}$::SAAT$_{Fa}$ |
| EcJWEB7 | pACYCD $P_{T7lac}$::atoB$_{Ec}$::hbd$_{Ca}$::crt$_{Ca}$-$P_{T7lac}$::ter$_{Td}$ | pRSFD $P_{T7lac}$::pdc$_{Zm}$::adhB$_{Zm}$::fdh$_{Cb}$-$P_{T7lac}$::SAAT$_{Fa}$ |
| EcJWBB1 | pACYCD $P_{T7lac}$::atoB$_{Ec}$::hbd$_{Ca}$::crt$_{Ca}$-$P_{T7lac}$::ter$_{Td}$ | pETD $P_{T7lac}$::adhE2$_{Ca}$::fdh$_{Cb}$-$P_{T7lac}$::SAAT$_{Fa}$ |
| EcJWBB2 | pACYCD $P_{T7lac}$::atoB$_{Ec}$::hbd$_{Ca}$::crt$_{Ca}$-$P_{T7lac}$::ter$_{Td}$ | pRSFD $P_{T7lac}$::adhE2$_{Ca}$::fdh$_{Cb}$-$P_{T7lac}$::SAAT$_{Fa}$ |
| EcJWBB3 | pETD $P_{T7lac}$::atoB$_{Ec}$::hbd$_{Ca}$::crt$_{Ca}$-$P_{T7lac}$::ter$_{Td}$ | pACYCD $P_{T7lac}$::adhE2$_{Ca}$::fdh$_{Cb}$-$P_{T7lac}$::SAAT$_{Fa}$ |
| EcJWBB4 | pETD $P_{T7lac}$::atoB$_{Ec}$::hbd$_{Ca}$::crt$_{Ca}$-$P_{T7lac}$::ter$_{Td}$ | pRSFD $P_{T7lac}$::adhE2$_{Ca}$::fdh$_{Cb}$-$P_{T7lac}$::SAAT$_{Fa}$ |
| EcJWBB5 | pRSFD $P_{T7lac}$::atoB$_{Ec}$::hbd$_{Ca}$::crt$_{Ca}$-$P_{T7lac}$::ter$_{Td}$ | pACYCD $P_{T7lac}$::adhE2$_{Ca}$::fdh$_{Cb}$-$P_{T7lac}$::SAAT$_{Fa}$ |
| EcJWBB6 | pRSFD $P_{T7lac}$::atoB$_{Ec}$::hbd$_{Ca}$::crt$_{Ca}$-$P_{T7lac}$::ter$_{Td}$ | pETD $P_{T7lac}$::adhE2$_{Ca}$::fdh$_{Cb}$-$P_{T7lac}$::SAAT$_{Fa}$ |
| EcJWBB7 | pACYCD $P_{T7lac}$::atoB$_{Ec}$::hbd$_{Ca}$::crt$_{Ca}$-$P_{T7lac}$::ter$_{Td}$ | pRSFD $P_{T7lac}$::adhE2$_{Ca}$::fdh$_{Cb}$-$P_{T7lac}$::SAAT$_{Fa}$ |
| EcJWBB8 | pACYCD $P_{T7lac}$::atoB$_{Ec}$::hbd$_{Ca}$::crt$_{Ca}$-$P_{T7lac}$::ter$_{Td}$ | pRSFD $P_{T7lac}$::trxA_adhE2$_{Ca}^{opt}$::fdh$_{Cb}$-$P_{T7lac}$::SAAT$_{Fa}$ |
| EcJWATF1 | pET29 $P_{T7lac}$::ATF1$_{Sc}$ | - |
| EcJWATF1$^{opt}$ | pET29 $P_{T7lac}$::ATF1$_{Sc}^{opt}$ | - |
| EcJWATF1$^{MBP}$ | pET29 $P_{T7lac}$::malE_ATF1$_{Sc}$ | - |
| EcJWATF1$^{NusA}$ | pET29 $P_{T7lac}$::nusA_ATF1$_{Sc}$ | - |
| EcJWATF1$^{TrxA}$ | pET29 $P_{T7lac}$::trxA_ATF1$_{Sc}$ | - |
| EcJWATF1$^{Chp1}$ | pET29 $P_{T7lac}$::ATF1$_{Sc}$ | pACYC $P_{araB}$::tig |
| EcJWATF1$^{Chp2}$ | pET29 $P_{T7lac}$::ATF1$_{Sc}$ | pACYC $P_{araB}$::groES::groEL |
| EcJWATF1$^{Chp3}$ | pET29 $P_{T7lac}$::ATF1$_{Sc}$ | pACYC $P_{pzt-1}$::groES::groEL::tig |
| EcJWATF1$^{Chp4}$ | pET29 $P_{T7lac}$::ATF1$_{Sc}$ | pACYC $P_{araB}$::dnaK::dnaJ::grpE |
| EcJWATF1$^{Chp5}$ | pET29 $P_{T7lac}$::ATF1$_{Sc}$ | pACYC $P_{araB}$::dnaK::dnaJ::grpE-$P_{pzt-1}$::groES::groEL |
| EcJWSAAT | pETD $P_{T7lac}$::atoB$_{Ec}$::hbd$_{Ca}$::crt$_{Ca}$-$P_{T7lac}$::ter$_{Td}$ | pET29 $P_{T7lac}$::SAAT$_{Sc}$ |
| EcJWSAAT$^{opt}$ | pETD $P_{T7lac}$::atoB$_{Ec}$::hbd$_{Ca}$::crt$_{Ca}$-$P_{T7lac}$::ter$_{Td}$ | pET29 $P_{T7lac}$::SAAT$_{Fa}^{opt}$ |
| EcJWSAAT$^{MBP}$ | pETD $P_{T7lac}$::atoB$_{Ec}$::hbd$_{Ca}$::crt$_{Ca}$-$P_{T7lac}$::ter$_{Td}$ | pET29 $P_{T7lac}$::malE_SAAT$_{Fa}$ |
| EcJWSAAT$^{NusA}$ | pETD $P_{T7lac}$::atoB$_{Ec}$::hbd$_{Ca}$::crt$_{Ca}$-$P_{T7lac}$::ter$_{Td}$ | pET29 $P_{T7lac}$::nusA_SAAT$_{Fa}$ |
| EcJWSAAT$^{TrxA}$ | pETD $P_{T7lac}$::atoB$_{Ec}$::hbd$_{Ca}$::crt$_{Ca}$-$P_{T7lac}$::ter$_{Td}$ | pET29 $P_{T7lac}$::trxA_SAAT$_{Fa}$ |
| EcJWSAAT$^{Chp1}$ | pETD $P_{T7lac}$::atoB$_{Ec}$::hbd$_{Ca}$::crt$_{Ca}$-$P_{T7lac}$::ter$_{Td}$ | pET29 $P_{T7lac}$::SAAT$_{Sc}$ |
| EcJWSAAT$^{Chp2}$ | pETD $P_{T7lac}$::atoB$_{Ec}$::hbd$_{Ca}$::crt$_{Ca}$-$P_{T7lac}$::ter$_{Td}$ | pET29 $P_{T7lac}$::SAAT$_{Sc}$ |
| EcJWSAAT$^{Chp3}$ | pETD $P_{T7lac}$::atoB$_{Ec}$::hbd$_{Ca}$::crt$_{Ca}$-$P_{T7lac}$::ter$_{Td}$ | pET29 $P_{T7lac}$::SAAT$_{Sc}$ |
| EcJWSAAT$^{Chp4}$ | pETD $P_{T7lac}$::atoB$_{Ec}$::hbd$_{Ca}$::crt$_{Ca}$-$P_{T7lac}$::ter$_{Td}$ | pET29 $P_{T7lac}$::SAAT$_{Sc}$ |
| EcJWSAAT$^{Chp5}$ | pETD $P_{T7lac}$::atoB$_{Ec}$::hbd$_{Ca}$::crt$_{Ca}$-$P_{T7lac}$::ter$_{Td}$ | pET29 $P_{T7lac}$::SAAT$_{Sc}$ |

FIG. 13

| Strains | Plasmid 1 | Plasmid 2 | Plasmid 3 |
|---|---|---|---|
| EcJWBB7 | pACYCD $P_{T7lac}$::atoB$_{Ec}$::hbd$_{Ca}$::crt$_{Ca}$-$P_{T7lac}$::ter$_{Td}$ | pRSFD $P_{T7lac}$::adhE2$_{Ca}$::fdh$_{Cb}$-$P_{T7lac}$::SAAT$_{Fa}$ | pACYC $P_{araB}$::groES::groEL; Amp$^R$ |
| EcJWSAAT$^{Chp1}$ | pETD $P_{T7lac}$::atoB$_{Ec}$::hbd$_{Ca}$::crt$_{Ca}$-$P_{T7lac}$::ter$_{Td}$ | pET29 $P_{T7lac}$::SAAT$_{Sc}$ | pACYC $P_{araB}$::tig |
| EcJWSAAT$^{Chp2}$ | pETD $P_{T7lac}$::atoB$_{Ec}$::hbd$_{Ca}$::crt$_{Ca}$-$P_{T7lac}$::ter$_{Td}$ | pET29 $P_{T7lac}$::SAAT$_{Sc}$ | pACYC $P_{araB}$::groES::groEL |
| EcJWSAAT$^{Chp3}$ | pETD $P_{T7lac}$::atoB$_{Ec}$::hbd$_{Ca}$::crt$_{Ca}$-$P_{T7lac}$::ter$_{Td}$ | pET29 $P_{T7lac}$::SAAT$_{Sc}$ | pACYC $P_{pzt-1}$::groES::groEL::tig |
| EcJWSAAT$^{Chp4}$ | pETD $P_{T7lac}$::atoB$_{Ec}$::hbd$_{Ca}$::crt$_{Ca}$-$P_{T7lac}$::ter$_{Td}$ | pET29 $P_{T7lac}$::SAAT$_{Sc}$ | pACYC $P_{araB}$::dnaK::dnaJ::grpE |
| EcJWSAAT$^{Chp5}$ | pETD $P_{T7lac}$::atoB$_{Ec}$::hbd$_{Ca}$::crt$_{Ca}$-$P_{T7lac}$::ter$_{Td}$ | pET29 $P_{T7lac}$::SAAT$_{Sc}$ | pACYC $P_{araB}$::dnaK::dnaJ::grpE-$P_{pzt-1}$::groES::groEL |

FIG. 14

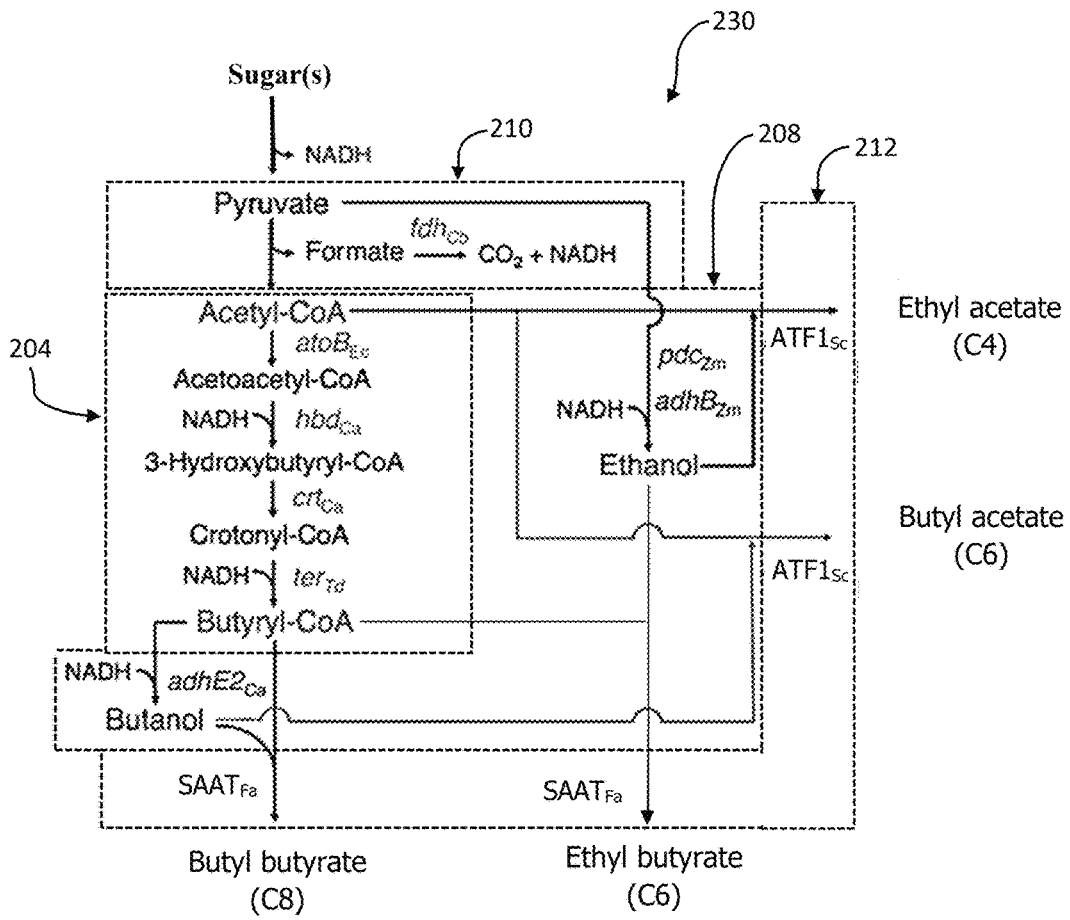

KEY:

AtoB$_{Ec}$ = acetyl-CoA acetyltransferase from *E. Coli*.
Hbd$_{Ca}$ = 3-hydroxybutyryl-CoA dehydrogenase from *C. acetobutylicum*.
Crt$_{Ca}$ = 3-enoyl-CoA dehydratase from *C. acetobutylicum*.
Ter$_{Td}$ = trans-2-enoyl=CoA reductase from *T. denticola*.
PDC$_{Zm}$ = pyruvate decarboxylase from *Z. mobilis*.
AdhB$_{Zm}$ = alcohol dehydrogenase from *Z. mobilis*.
AdhE2$_{Ca}$ = bifunctional acetaldehyde dehydrogenase/alcohol dehydrogenase from *C. acetobutylicum*.
Fdh$_{Cb}$ = formate dehydrogenase from *C. boidinii*.
ATF1$_{Sc}$ = alcohol acyltransferase from *S. cerevisiae*.
SAAT$_{Fa}$ = alcohol acyltransferase from *F. ananassa* (strawberry).

BUTYL ACETATE

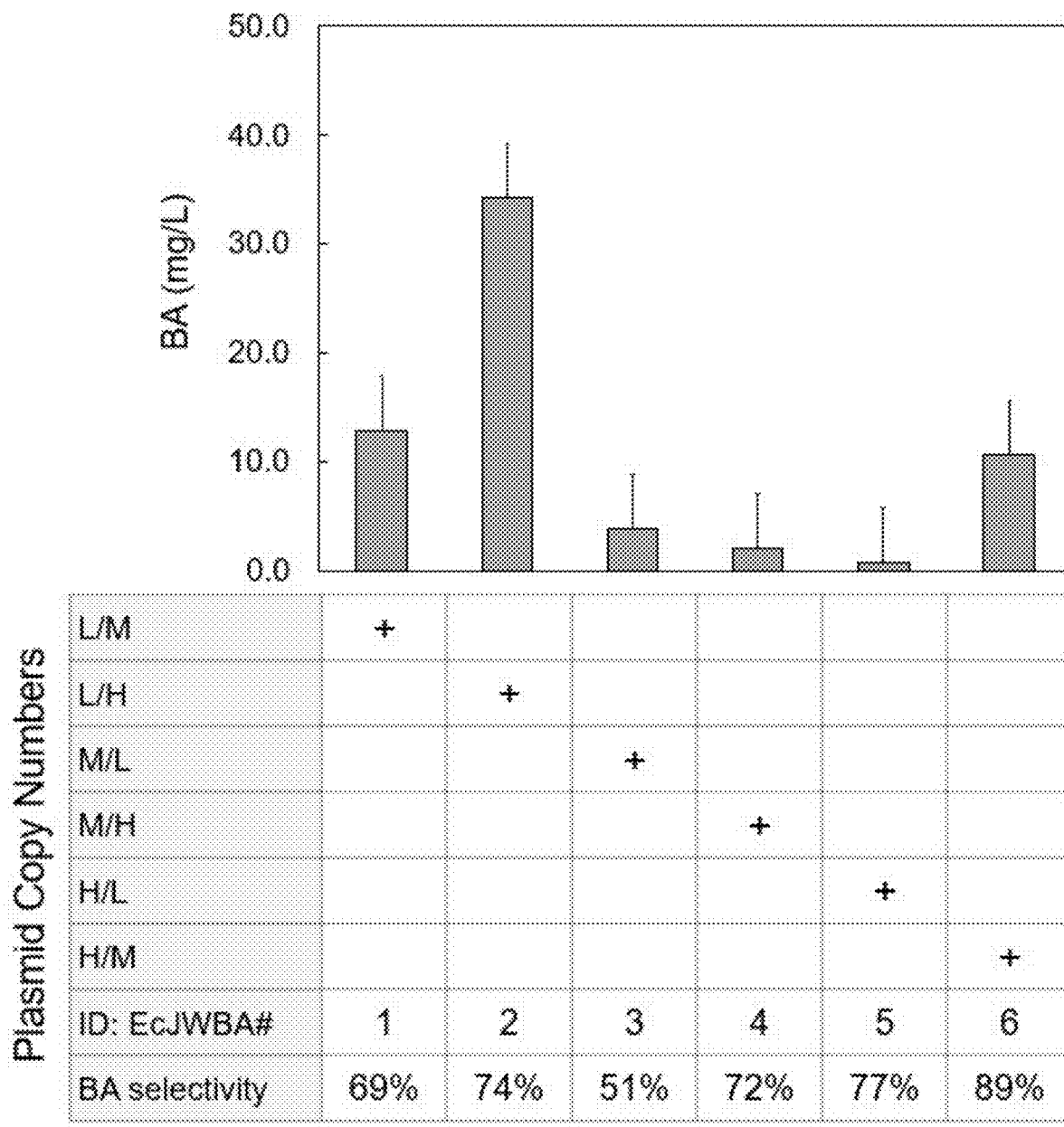

METHODS FOR PRODUCING DESIGNER ESTERS AND ASSESSING ALCOHOL ACYLTRANSFERASE SPECIFICITY FOR ESTER BIOSYNTHESIS

RELATED APPLICATIONS

This application claims the benefit of U.S. Provisional Application No. 63/260,654, filed Aug. 27, 2021, the entirety of which is incorporated herein by reference.

STATEMENT REGARDING FEDERALLY SPONSORED RESEARCH

This invention was made with government support under grant number NSF 1553250 awarded by the National Science Foundation and grant numbers DE-AC05-00OR22725 and DE-SC0019412 awarded by the Department of Energy. The government has certain rights in the invention.

REFERENCE TO SEQUENCE LISTING SUBMITTED VIA EFS-WEB

A Table of Sequences is provided at the end of the specification. Additionally, this application includes an electronically submitted sequence listing: "005820.0032US1.xml" created on Feb. 26, 2023 having a size of 135,763 bytes, the contents of which are incorporated by reference herein in its entirety.

TECHNICAL FIELD

This application relates to methods of microbial screening for identifying alcohol acyltransferases (AATs) for ester biosynthesis, more particularly, a microplate method of in situ fermentation with a solvent overlay followed by a colorimetric microplate assay of the solvent overlay for ester concentration. This application also relates to methods of selectively synthesizing a butyryl-coenzyme A (CoA) derived ester via microbial biosynthesis using submodules built into expression vectors for plug-and-play assembly of ester pathways.

BACKGROUND

Esters are industrially important chemicals with applications as, but not limited to, flavors, fragrances, solvents, and drop-in fuels, including biofuels. To replace conventional petroleum-based ester synthesis, which is neither renewable or sustainable, metabolic engineering and synthetic biology approaches have been pursued for at least a decade. However, harnessing metabolic capacities of various microbes for ester production is limited due to a lack of robust and efficient alcohol acyltransferases exhibiting high compatibility with various precursor pathways and microbial hosts.

Short-chain esters (C5-C10) often formulate volatile compounds commonly found in flowers, ripe fruits, and fermenting yeasts. Isoamyl acetate (3-methyl-1-butyl acetate) is known as banana oil. Banana oil had a global market of $5 billion in 2019. An isomer of isoamyl acetate, ethyl valerate, is fully compatible for blending with gasoline or diesel fuel, thereby having a potential application as a drop-in biofuel. For bioenergy applications, it is believed that short chain esters are potentially useful as drop-in fuels because of favorable properties such as high energy density, high hydrophobicity, and good compatibility with current engines, transport vessels, and storage density. For example, ethyl valerate, butyl butyrate, butyl valerate, and pentyl valerate are good fuel additives for gasoline while butyl butyrate and ethyl octanoate for jet fuel.

In nature, volatile esters are formulated by an alcohol acyltransferase (AAT, EC 2.3.1.84) that condenses an alcohol and an acyl-CoA in a thermodynamically favorable reaction, providing flavors and fragrances in ripening fruits and fermenting yeasts and having an ecological role in pollination. Inspired by nature, most of the metabolic engineering and synthetic biology strategies have deployed microbial conversion, such as the eukaryotic AATs originating from plants or yeasts for microbial biosynthesis of target esters. There is an abundance of acetyl-CoA in living cells, acetate esters being the most comment esters found in nature. By activating one-, two-, or three-carbon recursive elongation via the recursive fatty acid biosynthesis or Ehrlich pathways, it is possible to synthesis a large library of acetate esters containing unique alcohol moieties with linear, branched, and even and/or odd carbon chains. However, selective microbial biosynthesis of designer acetate esters at high efficiency has been an outstanding metabolic engineering problem. Moreover, the eukaryotic AATs lack robustness, efficiency, and compatibility as they commonly exhibit poor enzyme expression, solubility, and thermostability in microbes, thus limiting optimal microbial production of esters. In addition, limited knowledge on substrate profiles and specificities of AATs often requires laborious bioprospecting of AATs for individual target esters.

In copending U.S. application Ser. No. 17/453,305, filed Nov. 2, 2021, prokaryotic chloramphenicol acetyltransferase (CAT, EC 2.3.1.28) was repurposed to function as AAT. However, due to substrate promiscuity of these AAT/CAT enzymes, controllable microbial synthesis of designer esters with high selectivity remains a significant challenge.

Bioprospecting and protein engineering are promising strategies to find novel AATs with high specificity and activity towards a target ester. For instance, AAT of *Actinidia chinensis* (AATAc) was engineered to create an AATAc S99G variant that enhanced butyl octanoate production in *Escherichia coli* about 4.5-fold higher than the wildtype. Similarly, it has been reported in literature that a single F97W mutation in CAT of the mesophilic *Staphylococcus aureus* ($CAT_{Sa}$), identified by a model-guided protein design, achieved ~3.5-fold increase in isobutyl acetate (IBA) production in a thermophilic, cellulolytic bacterium *Clostridium thermocellum*. By combining both bioprospecting and model-guided protein engineering strategies, novel CATs have recently been discovered with improved efficiency, robustness, and compatibility. Even though research efforts in identifying beneficial AATs/CATs with high specificity and activities are promising, innumerous novel AATs/CATs are still underexplored. Also, remarkably, the substrate promiscuity of AATs enables microbial biosynthesis of acylate esters beyond acetate esters including propionate esters, lactate esters, butyrate esters, pentanoate esters, and hexanoate esters. Therefore, harnessing diversity of AATs, acyl-CoAs, and alcohols can result in the de novo microbial biosynthesis of a vast library of esters from renewable feedstocks for useful applications.

To access the specificities and activities of AATs/CATs directly, the enzymes need to be purified and characterized. Two colorimetric assays have been developed to determine AAT/CAT activities including the 5,5'-dithiobis-(2-nitrobenzoic acid) (DTNB) assay and the α-ketoglutarate dehydrogenase (α-KGDH)-coupled assay. These assays are designed to quantify free CoAs released from the AAT/CAT esterification of alcohols and acyl-CoAs by measuring either the 412 nm absorbance of yellowish 5-thio-2-nitrobenzoic acid (TNB) for the DTNB assay or the 340 nm absorbance of nicotinamide adenine dinucleotide (NADH) for (α-KGDH)-coupled assay. The key advantage of direct AAT/CAT measurement is that the assays can be performed in a high-throughput manner; however, some disadvantages for screening a large space of AATs/CATs include requirement of expensive acyl-CoA reagents and enzyme purification. Alternatively, direct measurement of esters for rapid, high-throughput screening of AAT/CAT specificities and activities in vivo can be attractive before determining the catalytic efficiencies in depth for promising enzyme candidates. Here, esters produced by microorganisms can be extracted with a solvent (e.g., n-hexane or n-hexadecane) and measured in a separate step. While the conventional gas chromatography coupled with mass spectrometer (GC/MS) is accurate in identifying and quantifying esters, it is low-throughput and expensive. Fortunately, the colorimetric assay, based on the hydroxylamine/iron chemistry, can rapidly quantify esters in high-throughput manner by first generating the ferric hydroxamate via the two steps of chemical reactions and then measuring its absorbance at 520 nm.

Moreover, for the past two decades, controlling selectivity of designer esters has been an outstanding metabolic engineering problem, mainly due to the complexity of the engineered pathways that require simultaneous expression of multiple heterologous enzymes causing deficient supply of precursor metabolites (i.e., alcohols and acyl-CoAs) for ester condensation. While the metabolic pathways directed towards biosynthesis of acetyl-CoA, butyryl-CoA, ethanol, and butanol are well known and can be tuned by manipulating gene replication (i.e., plasmid copy numbers) and transcription (e.g., RBSs, promoters) in many native and engineered ethanol/butanol producers, extension of these pathways for ester biosynthesis has been problematic due to poor AAT expression and specificity.

There is a need to develop microbial biosynthesis of designer butyryl-coenzyme A (CoA) derived esters with high selectivity, a method of doing so using a modular design of the butyryl-CoA-derived ester biosynthesis pathways for rapid construction and testing to produce higher yields of esters than ever before. Also, there is a need for a high-throughput microbial screen platform to identify AATs/CATs for designer ester biosynthesis, especially one that is simple, rapid, and efficient.

SUMMARY

In a first aspect, methods of microbial screening for identifying alcohol acyltransferases (AATs) for ester biosynthesis are provided herein. The methods involve preselected plasmids that are introduced into a respective host strain to form engineered microbes upon which in situ fermentation is performed followed by a colorimetric assay for quantification of production of the target esters. The which in situ fermentation includes providing a first microplate having a culture media in a plurality of wells thereof, which is a composition from which each of the engineered microbes can produce a target ester, for example a sugar solution, inoculating each well of the plurality of wells with one of the engineered microbes, adding an overlay of a solvent to each well, and then incubating the inoculated microplate for a preselected incubation period.

The colorimetric assay includes transferring a quantity of the overlay from each well after the in situ fermentation to one each of the well of the second microplate, treating each well to form an iron-hydroxamic acid complex aqueous phase, centrifuging the second microplate before measuring the absorbance of the iron-hydroxamic acid complex aqueous phase at a wavelength of 520 nm, and comparing the absorbance values to a standard curve for the target ester. The treatment can include mixing hydroxylamine stock solution to produce hydroxamic acid followed by addition of ferric ions to form the iron hydroxamic acid complex.

The methods may include measuring the optical density of each well at a wavelength of 600 nm after incubating but before the colorimetric assay as a measurement of growth of cells expressing the preselected plasmids.

The method can include computer model-guided engineering of any aspect of DNA sequences needed herein.

The preselected plasmids can be engineered plasmids comprising an AAT and/or or all or a portion of an ester pathway. In one embodiment, the host strain is Escherichia coli. The AAT can be selected from the group consisting of a modified chloramphenicol acetyltransferase comprising a tyrosine residue 20 having a phenylalanine (Y20F) mutation, a modified chloramphenicol acetyltransferase comprising a phenylalanine residue 97 having a single amino acid mutation (F97-mutation) and/or an alanine residue 138 having a single amino acid mutation (A138-mutation), an alcohol acetyl transferase factor 1 of Saccharomyces cerevisiae (ATF1$_{Sc}$) comprising a proline residue 348 having a single amino acid mutation (P348-mutation), a strawberry alcohol acyltransferase of Fragaria ananassa (SAAT$_{Fa}$) and mutations thereof, and combinations thereof. The chloramphenicol acetyltransferase can be from one or more of the following: Acidothermus cellulolyticus, Acinetobacter baylyi, Aspergillus niger, Aspergillus pseudoterreus, Bacillus coagulans, Bacillus oceanisedininis, Bacillus pumilus, Bacillus subtilis, Caldicellulosiruptor bescii, Campylobacter coli, Clostridioides difficile, Clostridium acetobutylicum, Clostridium autoethanogenum, Clostridium beijerinckii, Clostridium butyricum, Clostridium carboxidivorans, Clostridium celluloyticum, Clostridium clariflavum, Clostridium kluyveri, Clostridium ljungdahlii, Clostridium perfringens, Clostridium propionicum, Cyanobacteria spirulina, Clostridium thermocellum, Clostridium tyrobutyricum, Corynebacterium glutamicum, Cupriavidus necator, Cyanobacteria spirulina, Escherichia coli, Geobacillus caldoxylosilyticus, Geobacillus galactosidasius, Geobacillus icigianus, Geobacillus jurassicus, Geobacillus kaustophilus, Geobacillus lituanicus, Geobacillus stearothermophilus, Geobacillus subterraneus, Geobacillus thermantarcticus, Geobacillus thermocatenulatus, Geobacillus thermodenitrificans, Geobacillus thermoglucosidasius, Geobacillus G. thermoleovorans, Geobacillus toebii, Geobacillus uzenensis, Geobacillus vulcani, Geobacillus LC300, Haemophilus influenzae, Klebsiella aerogenes, Klebsiella sp., Lactococus lactis, Lysinibacillus boronitolerans, Morganella morganmii, Proteus mirabilis, Pseudomonas aeruginosa, Pseudomonas putida, Pichia kudriavzevii, Pichia pastoris, Ralstonia eutropha, Rhodosporidium toruloides, Saccharomyces cerevisiae, Staphylococcus aureus, Staphylococcus intermedius, Streptococcus agalectiae, Streptomyces acrinycini, Thermoanaerobacterium thermosaccharolyticum, Thrmoactinomyces sp., Vibrio anguiloarum, Yarrowia lipolytica, Zymomonas mobilis.

The solvent is selected from the group consisting of n-dodecane, n-tridecane, n-tetradecane, n-pentadecane, n-heptadecane, and n-octadecane, and combinations thereof.

In a second aspect, methods of selectively synthesizing a butyryl-coenzyme A (CoA) derived ester via microbial biosynthesis are provided herein. The method includes selecting a target ester to be synthesized by microbial biosynthesis from the group consisting of butyl acetate, butyl butyrate, and ethyl butyrate, providing a first expression vector encoding a first plurality of enzymes that convert acetyl-CoA to butyryl-CoA, and providing a second expression vector encoding a second plurality of enzymes. The second plurality of enzymes includes (i) at least one enzyme that facilitates production of nicotinamide adenine dinucleotide and hydrogen (NADH), (ii) at least one alcohol acetyltransferase selected for production of the target ester, and (iii) at least one enzyme that selectively determines a pathway for either butanol or ethanol synthesis. Then, the method includes inserting the first expression vector and the second expression vector into a microbial host cell. The expression of the first and second expression vectors in the microbial host cell produce the target ester.

In some embodiments, the first plurality of enzymes comprises *Escherichia coli* atoB (atoB$_{Ec}$), *Clostridium acetobutylicum* Hbd (hbd$_{Ca}$), *Clostridium acetobutylicum* crt (crt$_{Ca}$), and *Treponema denticola* ter (ter$_{Td}$). In some embodiments, the second plurality of enzymes comprises *Zymomonas mobilis* pdc (pdc$_{Zm}$) and *Zymomonas mobilis* adhB (adhB$_{Zm}$) or *Clostridium acetobutylicum* adhE2 (adhE2$_{Ca}$) for alcohol synthesis; *Candida boidinii* fdh (fdh$_{Cb}$) for facilitating the NADH production; and an alcohol acetyltransferase such as *Saccharomyces cerevisiae* ATF1 (ATF1$_{Sc}$) when an acetate ester is the target ester or *Fragaria ananassa* (cultivated strawberry) SAAT (SAAT$_{Fa}$) when an acylate ester is the target ester.

In all aspects, the first expression vector and the second expression vector each comprise a predetermined copy number of genes encoding the respective first plurality of enzymes and second plurality of enzymes, and the method includes determining a predetermined copy number of genes that produces the highest concentration of the target ester in a culture comprising the microbial host cell. In one embodiment, the copy number of genes encoding the first plurality of enzymes is lower than the copy number of genes encoding the second plurality of enzymes, more specifically the first expression vector has a copy number in a range of 5 to 15 and the second expression vector has a copy number in a range of 80 to 120.

In some embodiments, the host cell is selected from the group consisting of EcJWA2, EcJWEB2, EcJWBB2, EcJWBA15, EcJWEB7, and EcJWBB8.

In all aspects of this method, the method can include improving the solubility of the alcohol acetyltransferase and/or alcohol dehydrogenase.

BRIEF DESCRIPTION OF THE DRAWINGS

FIG. 12 is a Table of strains and plasmids used in the method of synthesizing esters from butyryl-CoA.

FIG. 13 is a Table of those strains that had three plasmids, the third plasmid being a chaperone used in the method of synthesizing esters.

FIG. 14 is a reaction scheme of the ester synthesis pathways within the submodules of FIG. 11.

FIG. 16A is a bar graph and chart of the concentration of butyl acetate and ester selectivity according to the pathways set forth in FIG. 15A.

DETAILED DESCRIPTION

Figure 1:
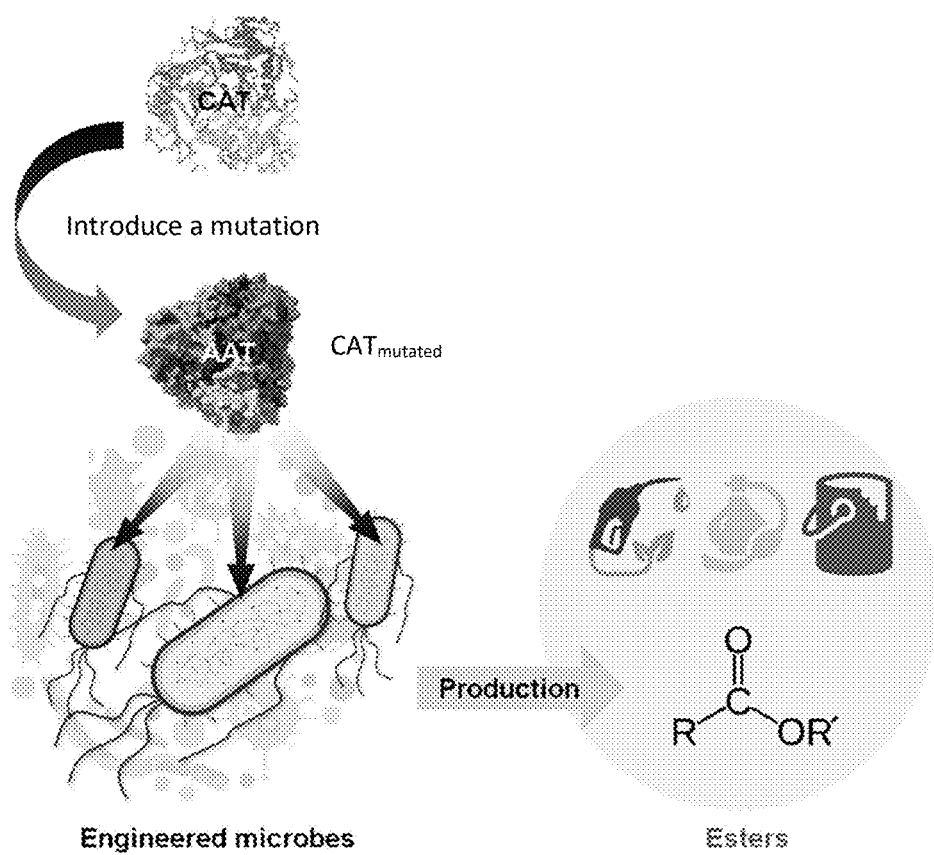
FIG. 1 (prior art) is schematic representation of the production of esters from an engineered microbe harboring a modified chloramphenicol acetyltransferase (CAT) having a Y20F mutation.

The following detailed description will illustrate the general principles of the invention, examples of which are additionally illustrated in the accompanying drawings. In the drawings, like reference numbers indicate identical or functionally similar elements.

Except in the working examples, or where otherwise explicitly indicated, all numbers in this description indicating amounts, parts, percentages, ratios, and proportions of material, physical properties of material, and conditions of reaction are to be understood as modified by the word "about." "About" as used herein means that a value is preferably +/−5% or more preferably +/−2%. Percentages for concentrations are typically % by wt. For pH values, "about" means+/−0.2.

In one aspect, a high-throughput microbial screening platform to probe specificities of AATs/CATs for designer ester biosynthesis is disclosed. This platform integrates microplate culturing with a modified colorimetric assay. This method provides useful information about AAT expression and activity, microbial health, and ester production. The high-throughput microbial screening platform not only probed the alcohol substrate specificity of both native and engineered AATs but also identified the beneficial mutations in engineered AATs for enhanced ester synthesis. As such, rapid profiling of the alcohol substrate preference of AATs for production of designer esters is now possible. This method is scalable and compatible with automated microplate handling systems to increase its screening capacity.

Figure 2:
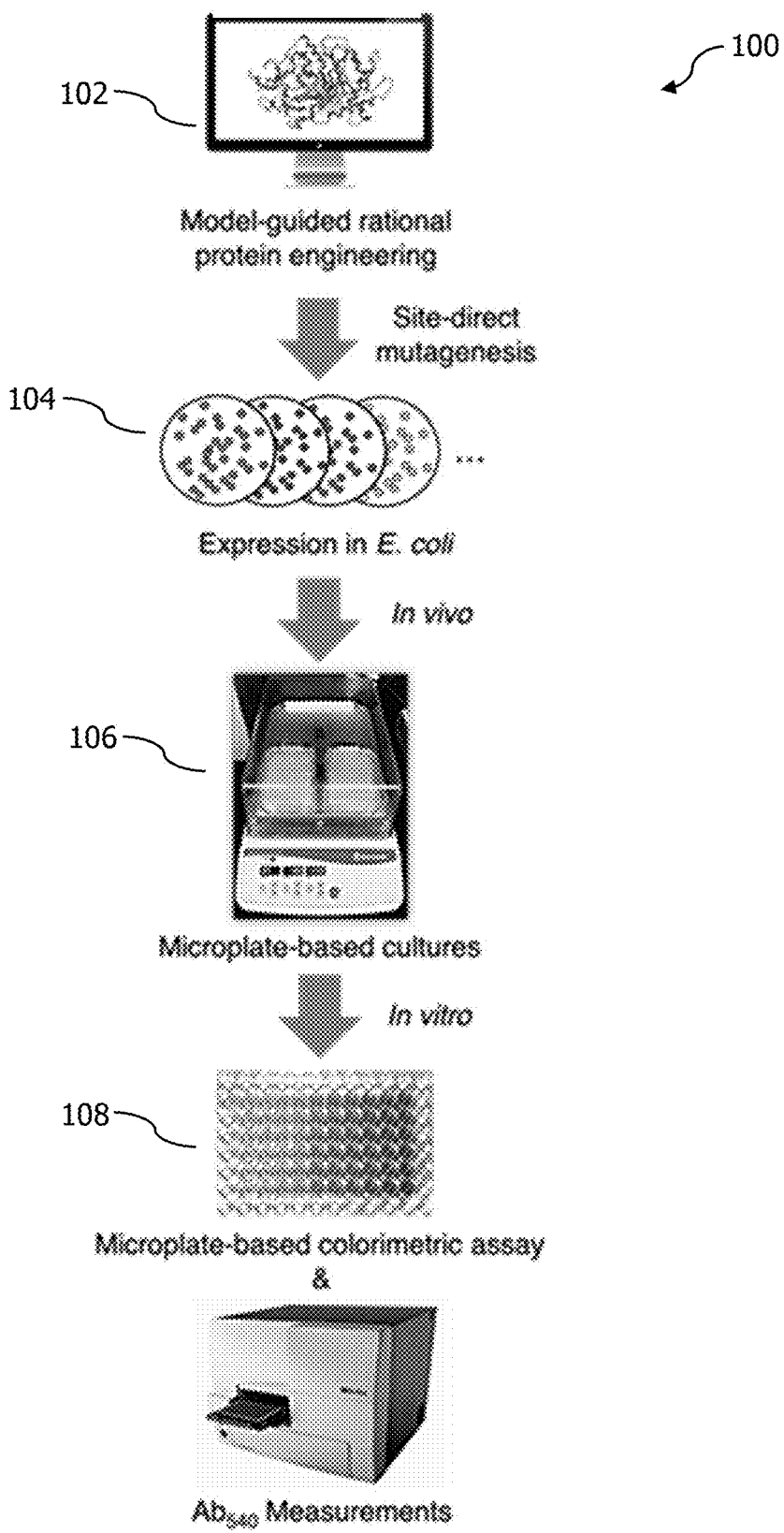
FIG. 2 is a schematic workflow of the high-throughput microbial screening method for screening beneficial AAT variants for improved selected target ester production.

Turning to FIG. 1, a schematic illustration is provided showing an alcohol acyltransferase or a mutated CAT that can function like an alcohol acyltransferase, which is then introduced into a microbe, such as a bacterium, yeast, or fungus to form an engineered microbe that can be fed sugars and/or volatile organic acids (acetate, butyrate) and optionally an alcohol to produce an ester. The alcohol may be produced by the system via acetyl-CoA or butyryl-CoA for straight chain esters or an Ehrlich pathway for branched esters. FIG. 2 is a flowchart of one example of a method 100 of microbial screening for identifying alcohol acyltransferases (AATs) for such ester biosynthesis. The method 100 begins by providing preselected plasmids 102, which may include computer model-guided rational protein engineering but is not limited thereto. Each of the preselected plasmids is introduced into a respective host strain to form engineered microbes 104. This can be accomplished by site-direct mutagenesis, or natural variants from genome mining. Next, in situ fermentation 106 is performed on the engineered microbes, which is optionally followed by measuring the optical density of each well at a wavelength of 600 nm as a measurement of growth of cells expressing the preselected plasmid. Lastly, a colorimetric assay 108 is performed for quantification of production of the target esters.

The in situ fermentation 106 includes providing a first microplate having a culture media in a plurality of wells thereof, inoculating each well of the plurality of wells with one of the engineered microbes to form an inoculated microplate, adding an overlay of a solvent, which can extract the target ester while not being toxic to the cells, to each well of the inoculated microplate before incubating, and incubating the inoculated microplate for a preselected incubation period. The culture media has a composition therein from which each of the engineered microbes can produce a target ester. Typically, the composition includes a sugar and may optionally include an alcohol and/or a buffer. The buffer can be a salt solution such as M9 buffer (NaCl, NaCl, $KH_2PO_4$, $Na_2HPO_4$, and/or $NH_4Cl$). The solvent overlay also minimizes medium evaporation, which causes water condensation, generates reproducible growth measurement, eliminates the ester extraction step (simplifies sample preparation), thereby lending compatibility with a high-throughput workflow, and reduces or eliminates product toxicity during fermentation (esters are known to be inhibitory to microbial health).

The solvent in the examples herein was n-hexadecane. Other suitable solvents like n-hexadecane are suitable herein, such as n-dodecane, n-tridecane, n-tetradecane, n-pentadecane, n-heptadecane, and n-octadecane. These solvents can extract short-chain esters, are not miscible with the fermentation broth, and do not inhibit cells.

The colorimetric assay 108 includes providing a second microplate to which, post-incubation, a quantity of the overlay from each well of the first microplate is transferred on a well-by-well basis, treating each well of the second microplate to form an iron-hydroxamic acid complex aqueous phase, centrifuging the second microplate after formation of the iron-hydroxamic acid complex aqueous phase, measuring the absorbance of the iron-hydroxamic acid complex aqueous phase at a wavelength of 520 nm, and comparing the absorbance values to a standard curve for the target ester.

Figure 4:
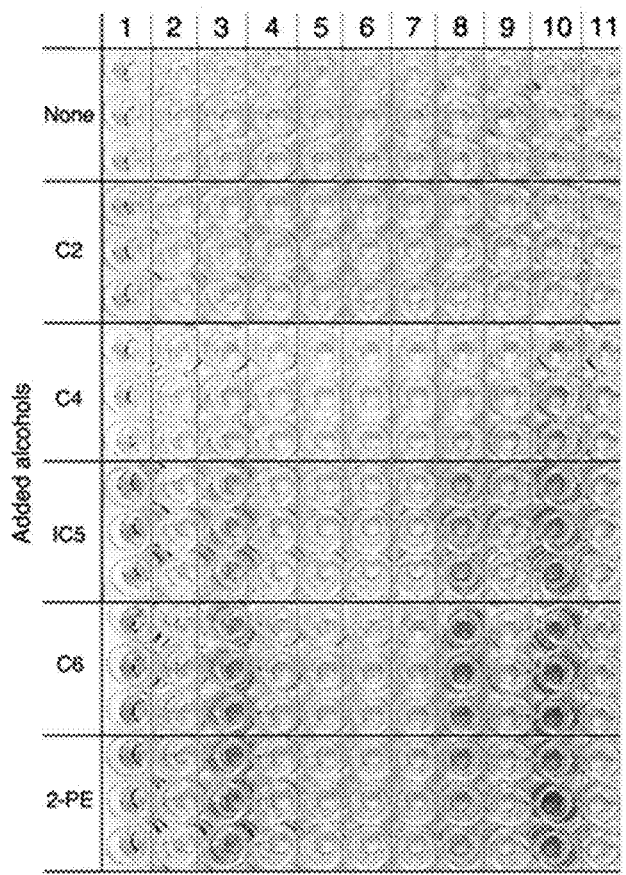
FIG. 4 is a photograph of a microplate colorimetric assay of n-hexadecane overlays from cultures of an *E. coli* strain carrying ATF1$_{Sc}$ variants (vertical rows 1 to 9), ATF1$_{Sc}$ wildtype (row 10), and SAAT$_{Fa}$ wildtype (row 11). From row 1 to 9, the ATF1$_{Sc}$ variants are P348W, P348R, P348M, P348H, P348K, P348N, P348I, P348S, and P348D.
Figure 5:
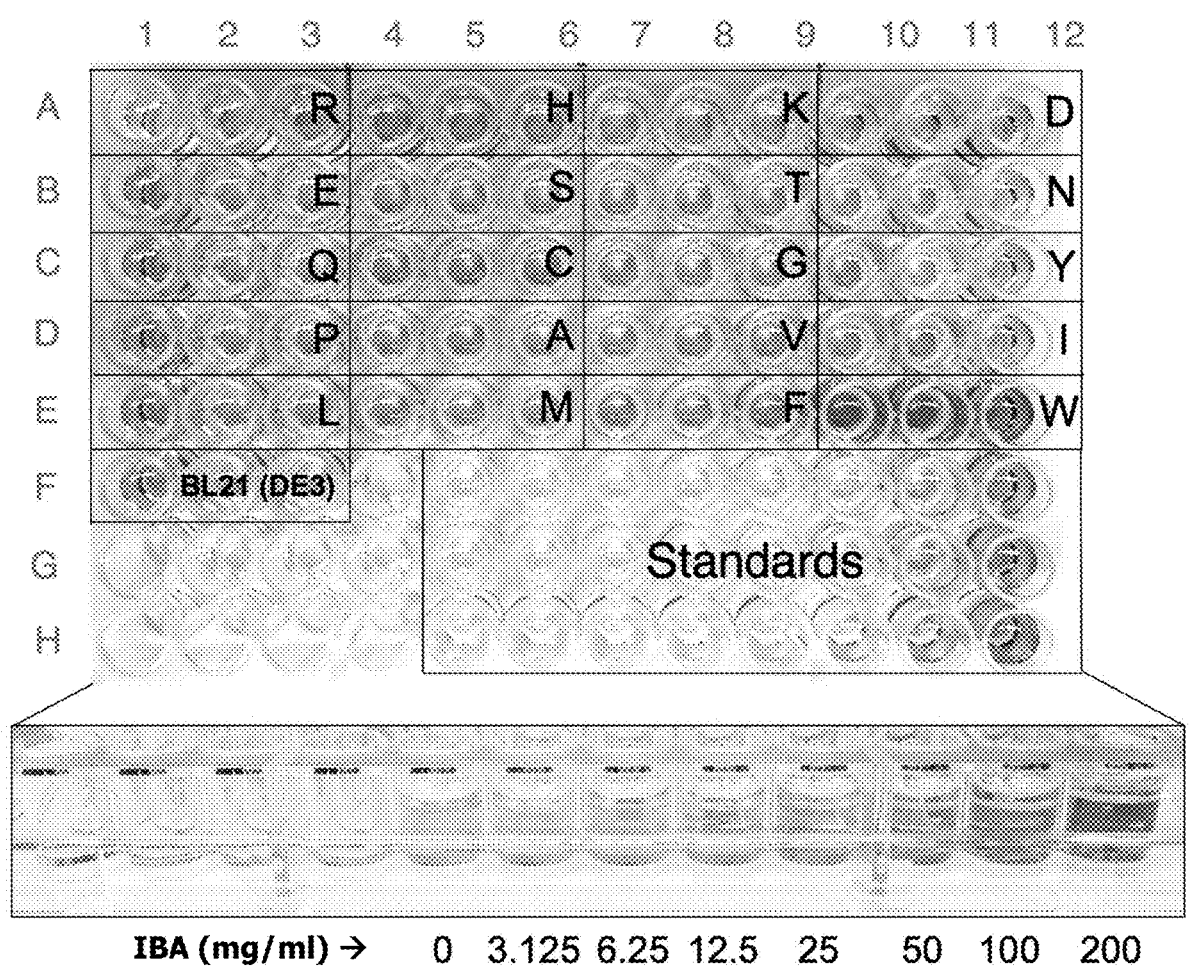
FIG. 5 is a photograph of a microplate colorimetric assay of n-hexadecane overlay samples and a series of isobutyl acetate (IBA) standards at different concentrations.

Treating each well of the second microplate includes mixing hydroxylamine stock solution to produce hydroxamic acid followed by addition of ferric ions to form the iron hydroxamic acid complex according to the reaction mechanism presented below. As shown in FIGS. 2, 4 and 5, the reactions of esters with hydroxylamine generate hydroxamic acids, a purple complex with ferric ion, thereby enabling colorimetric determinations of the ester concentration.

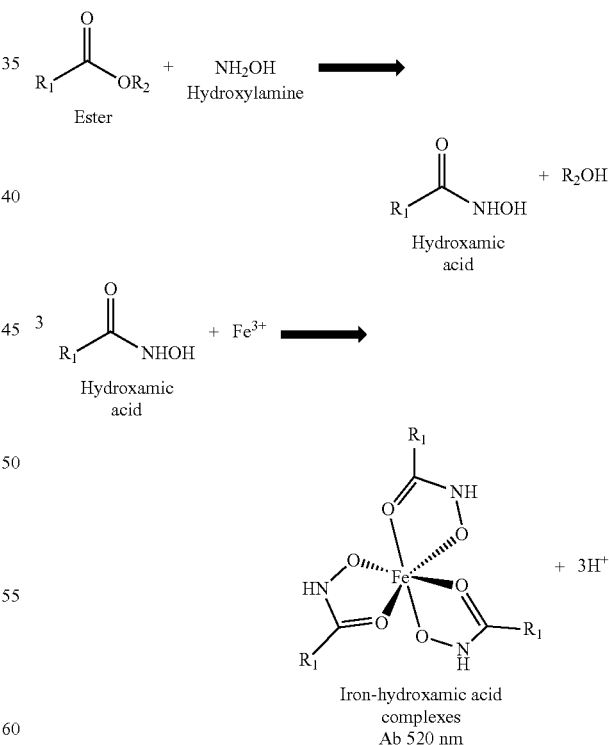

Figure 6:
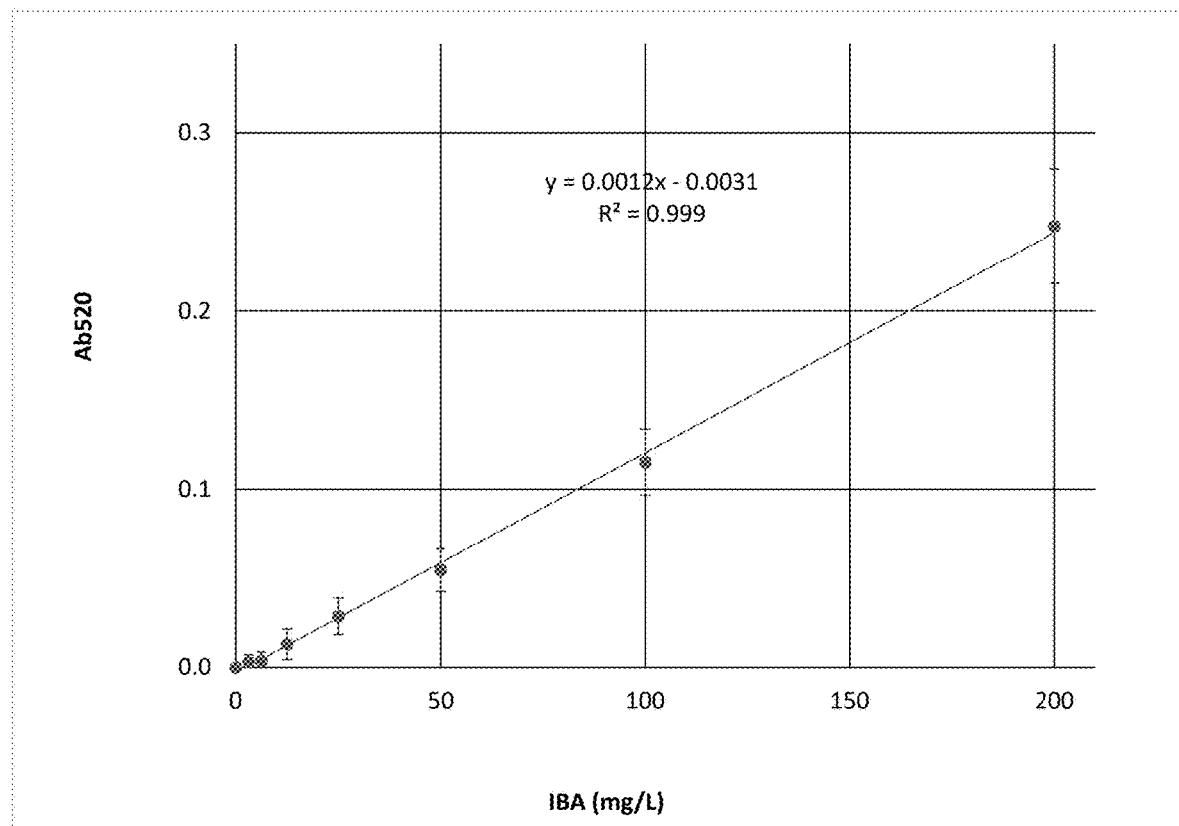
FIG. 6 is an isobutyl acetate standard colorimetric curve.
Figure 7:
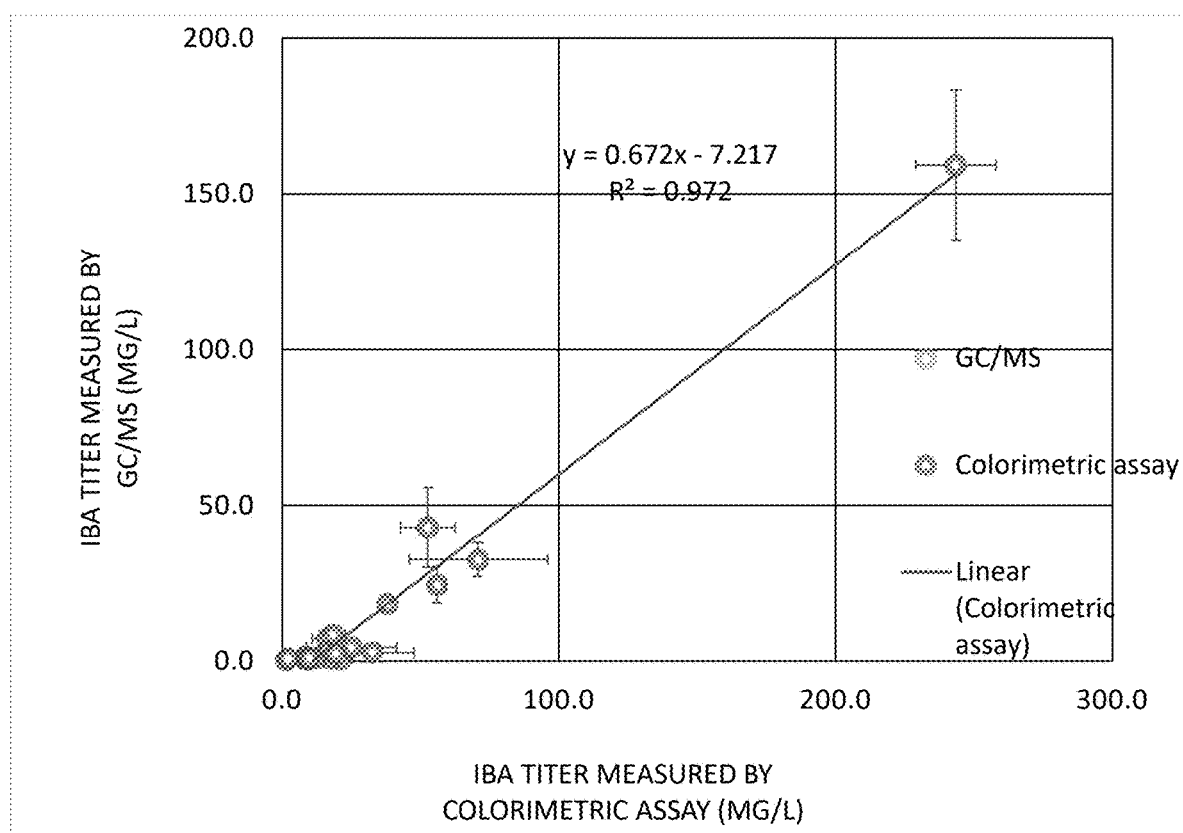
FIG. 7 is a comparison of the IBA titers measured by the high-throughput microbial screening against GC/MS methods.

Previously, this colorimetric assay was adapted for high-throughput screening of ethyl acetate (EA) production from C5, C6, and C12 carbon sources in *Kluyveromyces marxianus* where cell culture samples were first collected followed by ester extraction with hexane. The problem with this is that hexane is toxic to the microbes/cells; thus, it cannot be used for in situ fermentation and extraction as set forth herein. Hexadecane, however, is not toxic to the microbes/cells. Thus, a standard curve to estimate isobutyl acetate (IBA) production by the colorimetric assay was prepared. Using pure IBA in hexadecane, as shown in FIG. 6, an almost perfect linear correlation ($R^2=0.999$) was established between absorbance at 520 nm and IBA concentration within 0-200 mg/L. The results of trials were compared with this standard and with GC/MS results. As shown in FIG. 7, esters in hexadecane from the cell culture samples from the colorimetric assay disclosed herein were consistent with those measured by gas chromatography/mass spectroscopy (GC/MS). The method disclosed effectively eliminates the need to use GC/MS in AAT screening.

When the host strain produces ethanol endogenously, an inevitable by-product, the observed concentration of the target ester needs a correction factor to correct for the overestimation. To avoid overestimation of the concentration, we used $\Delta Ab_{520}$ wherein the $\Delta Ab_{520} = Ab_{520,\ AAT^+,\ ROH^+} - Ab_{520,\ AAT^+,\ ROH^-}$. This is the absorbance difference between culture samples with and without the target alcohol (ROH) availability. The target alcohol can be supplemented externally or produced by the cells. Another strategy, whereby correction is unnecessary, is to use a host strain void of an endogenous pathway causing the biosynthesis of unwanted alcohol byproduct(s) (e.g., ethanol).

The addition of centrifugation avoids the interference of an emulsified layer of an immiscible ethanol-hexadecane mixture that causes interference with the measured absorbance. Ethanol can be produced by the host strain and is also present in the ferric ion solution used in the colorimetric assay (see the reaction mechanism presented above). This problem did not occur in the previous colorimetric assays because the hexane used for ester extraction is miscible in ethanol. Centrifugation creates an immiscible hexadecane-ethanol mixture within the transparent organic phase that is separate from the purple aqueous phase.

The preselected plasmids are wildtype and/or engineered enzymes. In all aspects, the preselected plasmids can be engineered plasmids comprising an AAT. Some exemplary, non-limiting engineered plasmids include modified chloramphenicol acetyltransferase having a tyrosine residue 20 having a phenylalanine (Y20F) mutation, a modified chloramphenicol acetyltransferase comprising a phenylalanine residue 97 having a single amino acid mutation (F97-mutation) and/or an alanine residue 138 having a single amino acid mutation (A138-mutation), an alcohol acetyl transferase factor 1 of Saccharomyces cerevisiae (ATF1$_{Sc}$) comprising a proline residue 348 having a single amino acid mutation (P348-mutation), and a strawberry alcohol acyl-transferase of Fragaria ananassa (SAAT$_{Fa}$) and mutations thereof.

Microorganism strains harboring any of the AATs or modified proteins discussed herein can be yeast, fungi, or bacteria. Non-limiting examples of species that can harbor the ester pathways include species belonging to genera Bacillus, Pseudomonas, Erwinia, Caulobacter, Serratia, Arthrobacter, Micrococcus, Flavobacterium, Chromobacterium, Agrobacterium, Hyphomycrobium, Rhizobium, Bradyrhizobium, Sinorhizobium, Azorhizobium, Mesorhizobium and Allorhizobium, most likely useful for agricultural applications, Bacillus coagulans, Saccharomyces boulardii, Escherichia coli Nissle 1917, useful probiotics, and Acidothermus cellulolyticus, Acinetobacter baylyi, Aspergillus niger, Aspergillus pseudoterreus, Bacillus coagulans, Bacillus subtilis, Caldicellulosiruptor bescii, Clostridium aceto- butylicum, Clostridium autoethanogenum, Clostridium beijerinckii, Clostridium butyricum (Cb), Clostridium carboxidivorans, Clostridium celluloyticum, Clostridium clariflavum, Clostridium kluyveri, Clostridium ljungdahlii, Cupriavidus necator, Clostridium propionicum, Cyanobacteria spirulina, Clostridium thermocellum, Clostridium tyrobutyricum, Corynebacterium glutamicum, Cupriavidus necator, Cyanobacteria spirulina, Escherichia coli (Ec), Geobacillus caldoxylosilyticus, Geobacillus galactosidasius, Geobacillus icigianus, Geobacillus jurassicus, Geobacillus kaustophilus, Geobacillus lituanicus, Geobacillus stearothermophilus, Geobacillus subterraneus, Geobacillus thermantarcticus, Geobacillus thermocatenulatus, Geobacillus thermodenitrificans, Geobacillus thermoglucosidasius, Geobacillus G. thermoleovorans, Geobacillus toebii, Geobacillus uzenensis, Geobacillus vulcani, Geobacillus LC300, Haemophilus influenzae (Ha), Klebsiella sp. (Kl), Lactococus lactis, Lysinibacillus boronitolerans (Lys), Pseudomonas putida, Pichia kudriavzevii, Pichia pastoris, Ralstonia eutropha, Rhodosporidium toruloides, Saccharomyces cerevisiae, Staphylococcus aureus (Sa), Thermoanaerobacterium thermosaccharolyticum, Yarrowia lipolytica, Zymomonas mobilis, and combinations thereof. The strain referenced in the example in FIG. 2 is Escherichia coli.

These species can be useful for harnessing the pathways to convert sugars and/or volatile organic acids (acetate, butyrate) into esters. In agriculture, these species can harness the pathways to make esters beneficial for microbes and plants interaction that can potentially benefit plant growth.

With respect to the preselected inoculation period is dependent upon the host strain selected, such as those expressly identified in the preceding paragraph and on the size of the inoculation. The preselected inoculation period typically being at least 1 hour. In some embodiments, the inoculation period is at least 3 hours, more preferably at least 6 hours. In some embodiments, the inoculation period is at least 12 hours, more preferably at least 24 hours.

The above method provides the advantage of being able to measure both esters and cell growth, which helps not only screen relative AATs/CATs specificities and activities rapidly but also evaluate the effect of expressing these enzymes on microbial health. The high-throughput microbial screening method was validated by probing the alcohol substrate preferences of CAT$_{Sa}$ F97 variants, ATF1$_{Sc}$ P348 variants derived from ATF1$_{Sc}$ of Saccharomyces cerevisiae, and SAAT$_{Fa}$ of Fragaria ananassa. This method will be a useful tool to identify novel AATs that have important roles in nature and industrial biocatalysis for designer bioester production.

Figure 11:
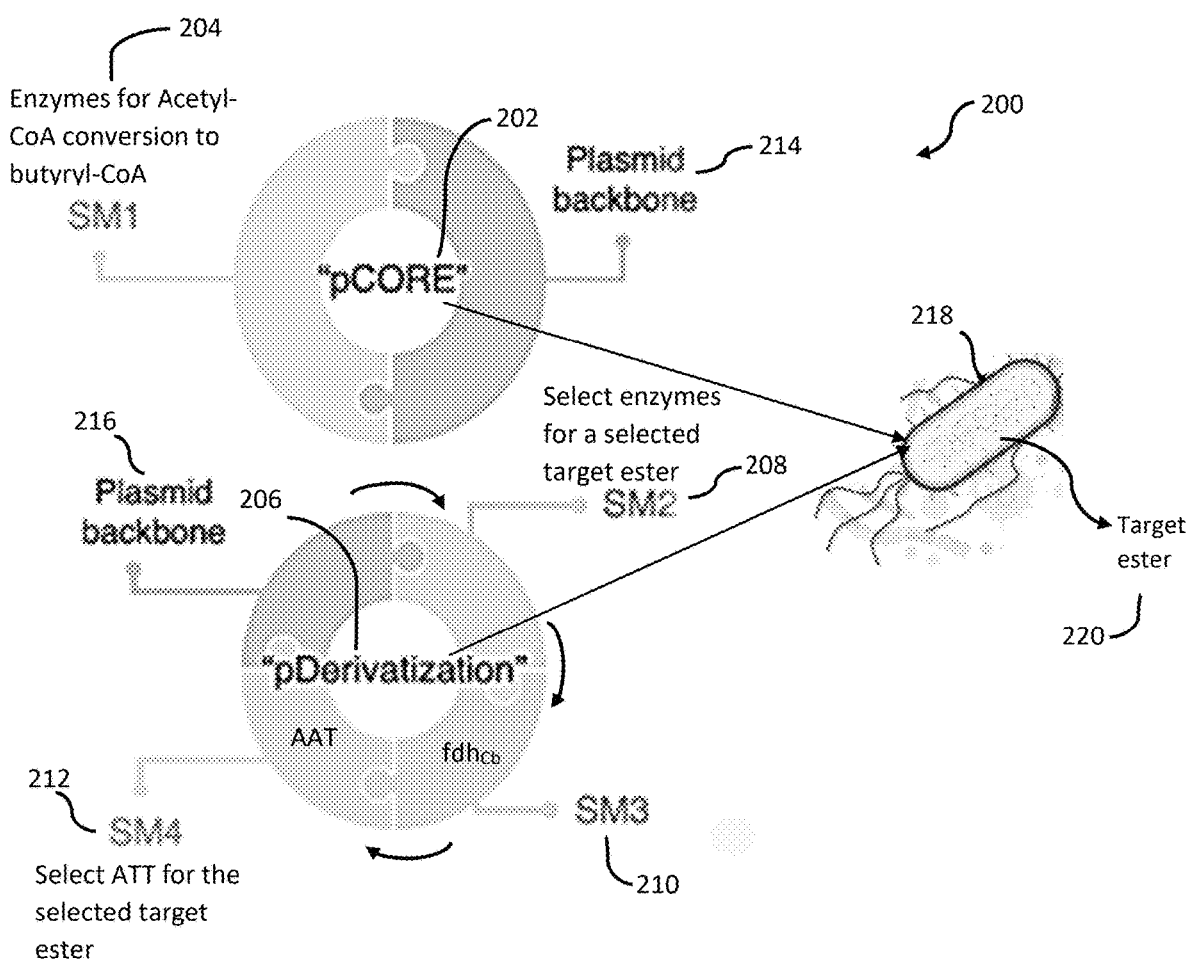
FIG. 11 is a schematic representation of a method of selectively synthesizing a butyryl-CoA derived ester via microbial biosynthesis.

Referring now to FIG. 11, in another aspect, a method 200 of selectively synthesizing a target ester 220, such as a butyryl-CoA derived ester, via microbial biosynthesis is disclosed. The method of high throughput assay disclosed above can be used first to identify suitable candidates for use in this biosynthesis method. The method includes selecting a target ester 220, such as butyl acetate, butyl butyrate, and ethyl butyrate, to be synthesized by microbial biosynthesis via a host cell 218. The host cell can be any of those disclosed herein with respect to the high throughput assay and those listed in FIG. 12, but is not limited thereto. The host cells listed in FIG. 12, except for EcJWBA15, were TCS083 ΔfadE (DE3), the exception by TCS095 (DE3). The method includes providing a first expression vector, represented as pCore 202 in FIG. 11, providing a second expression vector, represented as pDerviatization 204 in FIG. 11, that encodes a second plurality of enzymes, and inserting the first expression vector and the second expression vector into a host cell 218. The expression of the first and second expression vectors in the host cell produces the target ester.

The first expression vector 202 encodes a first plurality of enzymes 204 that convert acetyl-CoA to butyryl-CoA. The first plurality of enzymes comprises *Escherichia coli* acetyl-CoA acetyltransferase (atoB$_{Ec}$), *Clostridium acetobutylicum* 3-hydroxybutyryl-CoA dehydrogenase (hbd$_{Ca}$), *Clostridium acetobutylicum* 3-enoyl-CoA dehydratase (crt$_{Ca}$), and *Treponema denticola* trans-2-enoyl-CoA reductase (ter$_{Td}$).

The second expression vector's plurality of enzymes has at least one enzyme thereof that selectively determines a pathway for either butanol or ethanol synthesis, represented as submodule 2 (SM2) 208 in FIG. 11, at least one enzyme that facilitates production of nicotinamide adenine dinucleotide and hydrogen (NADH), represented as submodule 3 (SM3) 210, and at least one enzyme that is an alcohol acetyltransferase selected for synthesis of the target ester, represented as submodule 4 (SM4) 212 in FIG. 11. Various enzymes can be selected for each of submodule 2, 3, and 4 and myriad combinations thereof can be created.

FIG. 14 is a schematic of the reaction pathways 230 from the input of fermentable sugar(s) to the output of the target esters. With reference to FIG. 14, in one embodiment, the enzymes for SM2 208 comprise *Zymomonas mobilis* pyruvate decarboxylase (pdc$_{Zm}$) and *Zymomonas mobilis* alcohol dehydrogenase (adhB$_{Zm}$) for ethanol synthesis or *Clostridium acetobutylicum* aldehyde-alcohol dehydrogenase (adhE2$_{Ca}$) for butanol synthesis. The enzyme for SM3 210 comprises *Candida boidinii* formate dehydrogenase (fdh$_{Cb}$) for facilitating the NADH production. The enzyme for SM4 212 is an alcohol acetyltransferase. The alcohol acetyl transferase can be *Saccharomyces cerevisiae* alcohol acetyltransferase (ATF1$_{Sc}$) when an acetate ester is the target ester or *Fragaria ananassa* (cultivated strawberry) alcohol acetyltransferase (SAAT$_{Fa}$) when an acylate ester is the target ester. Myriad combinations of these enzymes based on the submodules in FIGS. 11 and 14 are provided in the table presented herein as FIG. 12.

Figure 15A:
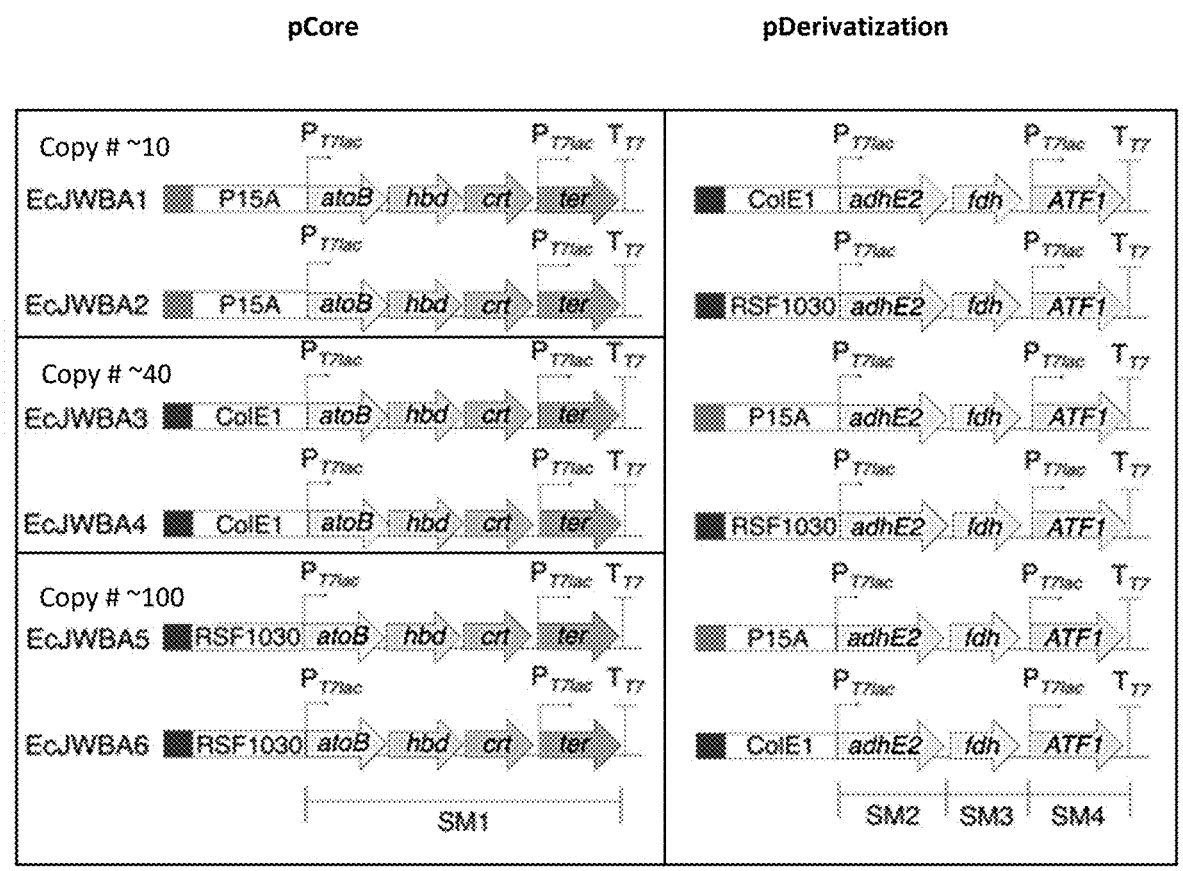
FIG. 15A is a chart of the pCore and pDerivatization combinations based on differing copy numbers for butyl acetate synthesis.
Figure 15B:
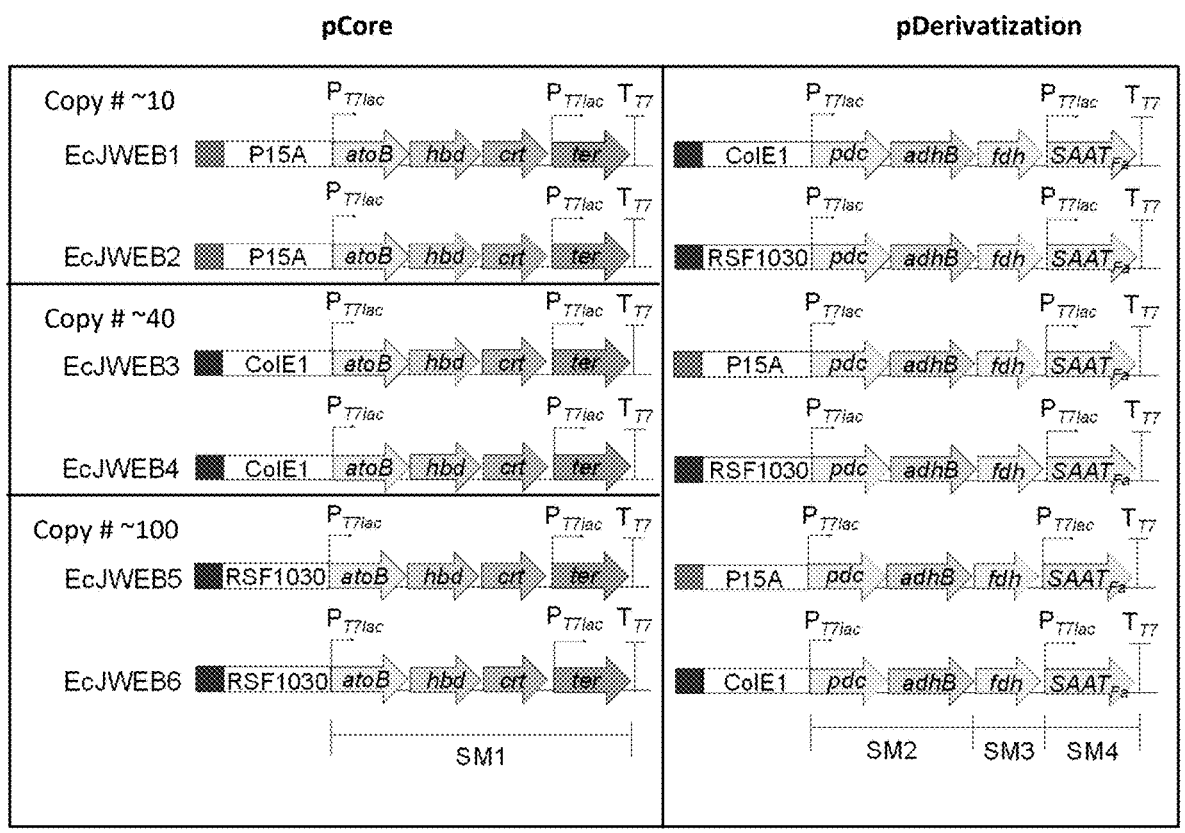
FIG. 15B is a chart of the pCore and pDerivatization combinations based on differing copy numbers for ethyl butyrate synthesis.
Figure 15C:
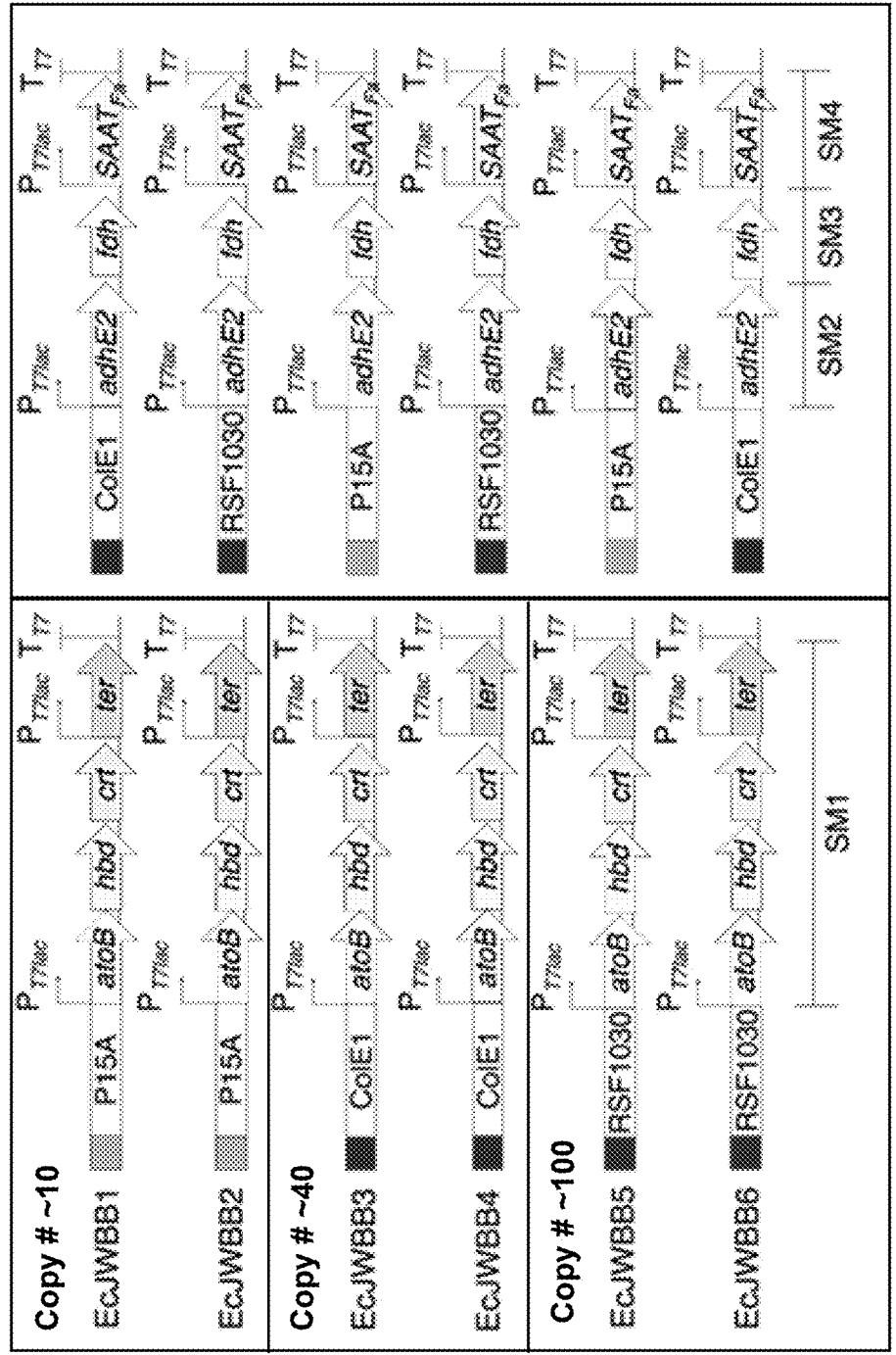
FIG. 15C is a chart of the pCore and pDerivatization combinations based on differing copy numbers for butyl butyrate synthesis.

One advantage provided by this method is the ease of creating various pCore 202 and pDerviatization 206 expression vectors using plasmid backbones 214 and 216 to build numerous sources thereof having different copy numbers to determine the number of genes encoding the enzymes to produce the highest concentration of target ester via the biosynthesis. Copy number refers to the origins of replication, which changes based on the particular nucleotide sequence on the plasmid at which replication is initiated. Low copy number as used herein means a value of 20 or less. A high copy number as used herein means a value at or greater than 100. Medium copy number as used herein means those values between a low copy number and a high copy number. With reference to FIGS. 15A-15C, in certain examples the first expression vector includes a plasmid that has a low copy number, a medium copy number, or a high copy number of the genes encoding the enzymes described herein, and the second expression vector includes a plasmid having a low copy number, a medium copy number, or a high copy number, thereby providing the possibility of three sources of each expression vector for a total of six different variations for substitution into the submodules herein. The method comprises making each of a low copy number core plasmid, a medium copy number core plasmid, and a high copy number core plasmid and each of a low copy number derivatization plasmid, a medium copy number derivatization plasmid, and a high copy number derivatization plasmid, and introducing one each of all possible combinations thereof into the strains. FIG. 15A is a chart of the combinations for butyl acetate. FIG. 15B is a chart of the combinations for ethyl butyrate. FIG. 15C is a chart of the combinations for butyl butyrate. The method includes identifying the combination of copy numbers with the highest concentration of the target ester.

While the engineered pathway module(s) can be introduced cells via plasmids, it can also be integrated into the chromosome of the host cell to achieve genetic stability.

Figure 16B:
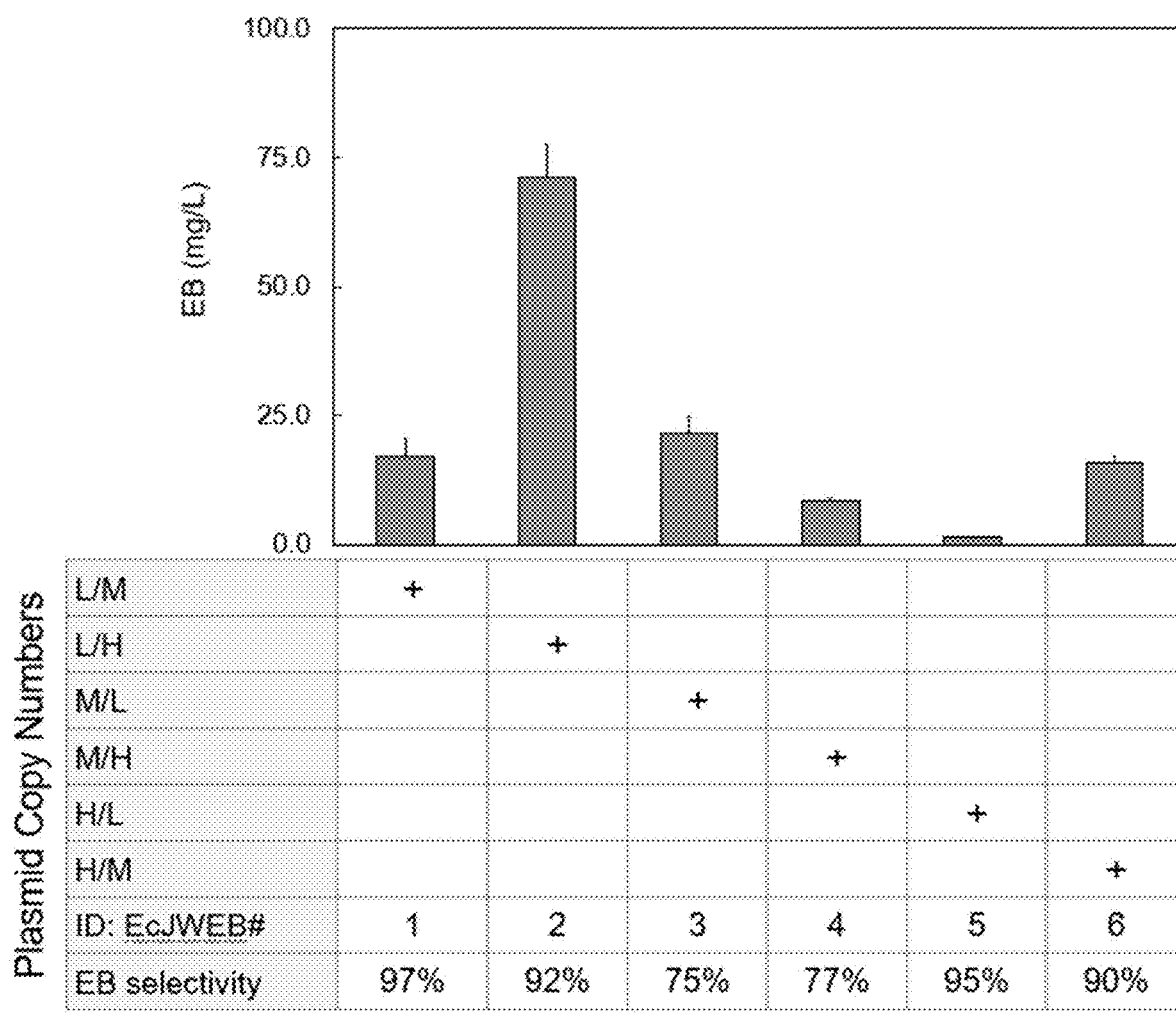
FIG. 16B is a bar graph and chart of the concentration of ethyl butyrate and ester selectivity according to the pathways set forth in FIG. 15B.
Figure 16C:
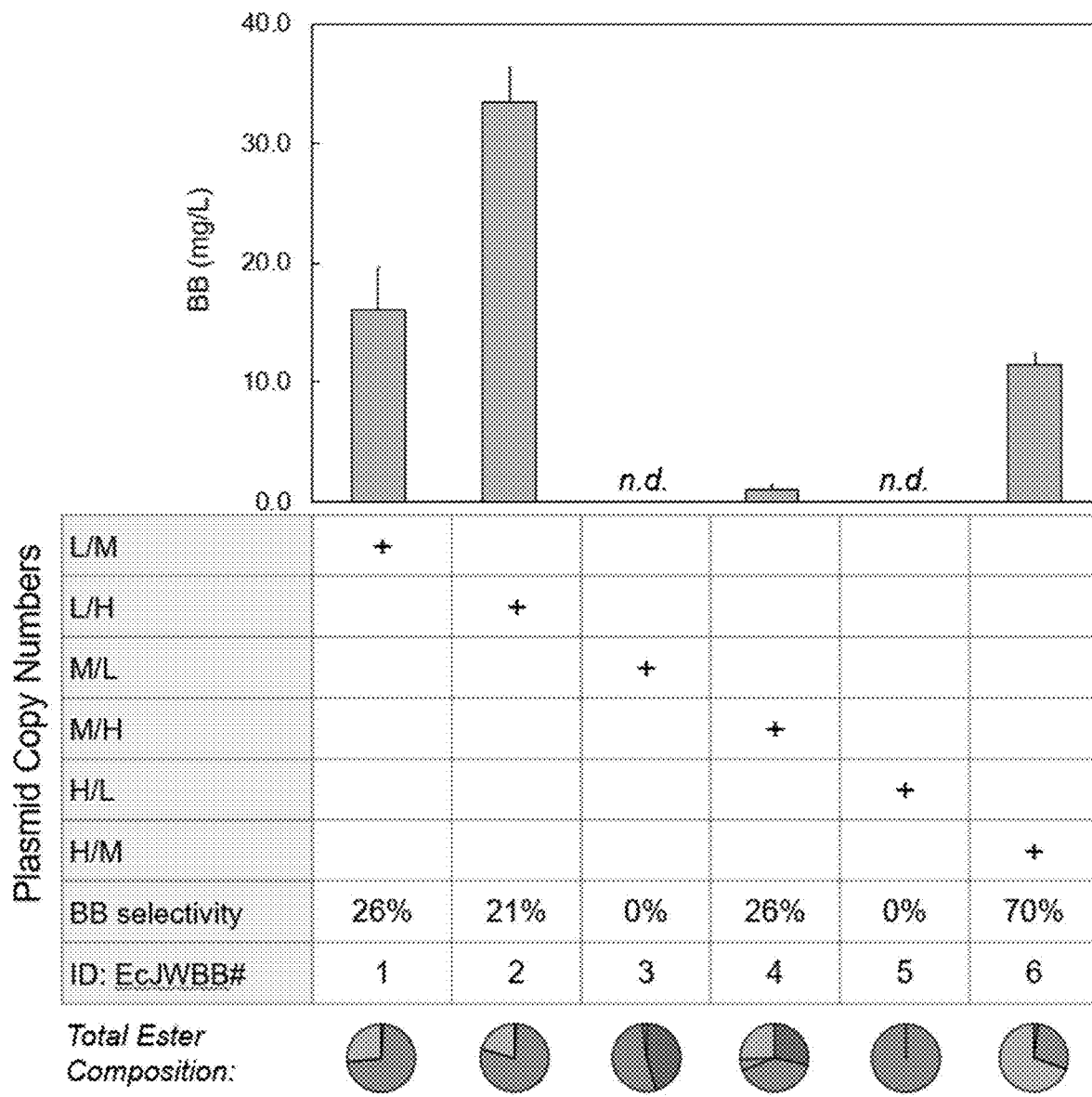
FIG. 16C is a bar graph and chart of the concentration of butyl butyrate and ester selectivity according to the pathways set forth in FIG. 15C.

Referring now to FIGS. 16A-16C, bar graphs of the results for butyl acetate, ethyl butyrate, and butyl butyrate are provided. Surprisingly, all three esters had their highest concentration when pCore had a low copy number and pDerivatization had a high copy number. In other words, the first expression vector and the second expression vector each comprise a predetermined copy number of genes encoding the respective first plurality of enzymes and second plurality of enzymes, and the copy number of genes encoding the first plurality of enzymes is lower than the copy number of genes encoding the second plurality of enzymes. We found that EcJWBA2 (FIG. 16A), EcJWEB2 (FIG. 16B), and EcJWBB2 (FIG. 16C) carrying the pCore with low copy number and the pDerivatization with high copy number achieved the highest ester production among the six initial strains characterized for each compound, indicating that higher alcohol production and/or AAT expression are required for efficient ester synthesis. FIG. 16A evidences that EcJWBA2 produced 34.2±6.6 mg/L of BA with the selectivity of 74.3%. FIG. 16B evidences that EcJWEB2 produced 71.0±6.6 mg/L of EB with the selectivity of 92.0%. FIG. 16C evidences that EcJWBB2 produced 33.5±2.9 mg/L of BB with the selectivity of 20.8%.

Using the method described above that uses the submodules, each ester production strain can be generated from an engineered modular (chassis) cell and an exchangeable ester production module in a plug-and-play fashion. Herein, the exchangeable ester production modules are compatible with the chassis cell for efficient biosynthesis of designer esters with controllable selectivity of the target ester. To build these modules, we arranged a set of 11 heterologous genes, derived from bacteria, yeasts, and plants, into the four submodules to facilitate rapid module construction via manipulation of gene replication, transcription, translation, post-translation, pathway enzymes, and even pathway induction conditions (which is discussed in detail in Working Examples 7-12). Furthermore, the highest production of esters (i.e., BA, EB, and BB) ever reported in *E. coli* with controllable selectivity was achieved using these methods.

In controlling the selectivity problem of butyryl-CoA-derived ester biosynthesis, ATF1$_{Sc}$ specific for acetate ester biosynthesis (e.g., BA) and SAAT$_{Fa}$ specific for butyrate ester biosynthesis (e.g., EB and BB) were used as seen in FIGS. 11 and 14. Additionally, the pathway gene replication and transcription for sufficient supply of precursor metabolites was determined. However, the ester titer and selectivity were still lower than desired since the problem of proper expression of pathway enzymes remained, which is difficult to solve. Based on the Protein-Sol, a web tool for predicting protein solubility from sequence, AATs are predicted to have the lowest solubility among the engineered pathway enzymes followed by AdhE2$_{Ca}$. The prediction is consistent with the SDS-PAGE analysis conducted by the Applicant and by others.

As such the solubility problem of the AATs and ideally AdhE2$_{Ca}$, when present in a selected pathway, must be solved. Herein, we used codons, fusion tags, co-expression of chaperones and combinations thereof to improve the solubility thereof. Remarkably, fusion tags improve ATF1$_{Sc}$ solubilization while chaperones enhance expression of $SAAT_{Fa}$, which is not trivial to predict or explain. In general, solubilization with fusion tags are enzyme specific; however, use of chaperones alone can be very unspecific, especially when multiple enzymes are expressed simultaneously.

The working examples 7-12, show the significance of modulating the translation and post-translation for multiple pathway enzymes, which cannot be effectively addressed by mere optimization of gene replication and transcription alone as commonly practiced in the fields of metabolic engineering and synthetic biology. In certain example embodiments, the genes of the first expression vector and/or the second expression vector are under the control of an inducible promoter. As those skilled in the art will appreciate, several inducible promoters are available to induce gene expression. These include, for example, any chemically inducible promoter or temperature inducible promoter that can be used to induce gene expression of the enzymes described herein. For example, the genes of the first expression vector and/or the second expression vector can be configured such that they are under the control of a lactose operon (lac operon), in which case the molecular reagent isopropyl-β-D-thiogalactopyranoside (IPTG) can be used to induce expression of the genes of the first expression vector and/or the second expression vector.

Figure 17A:
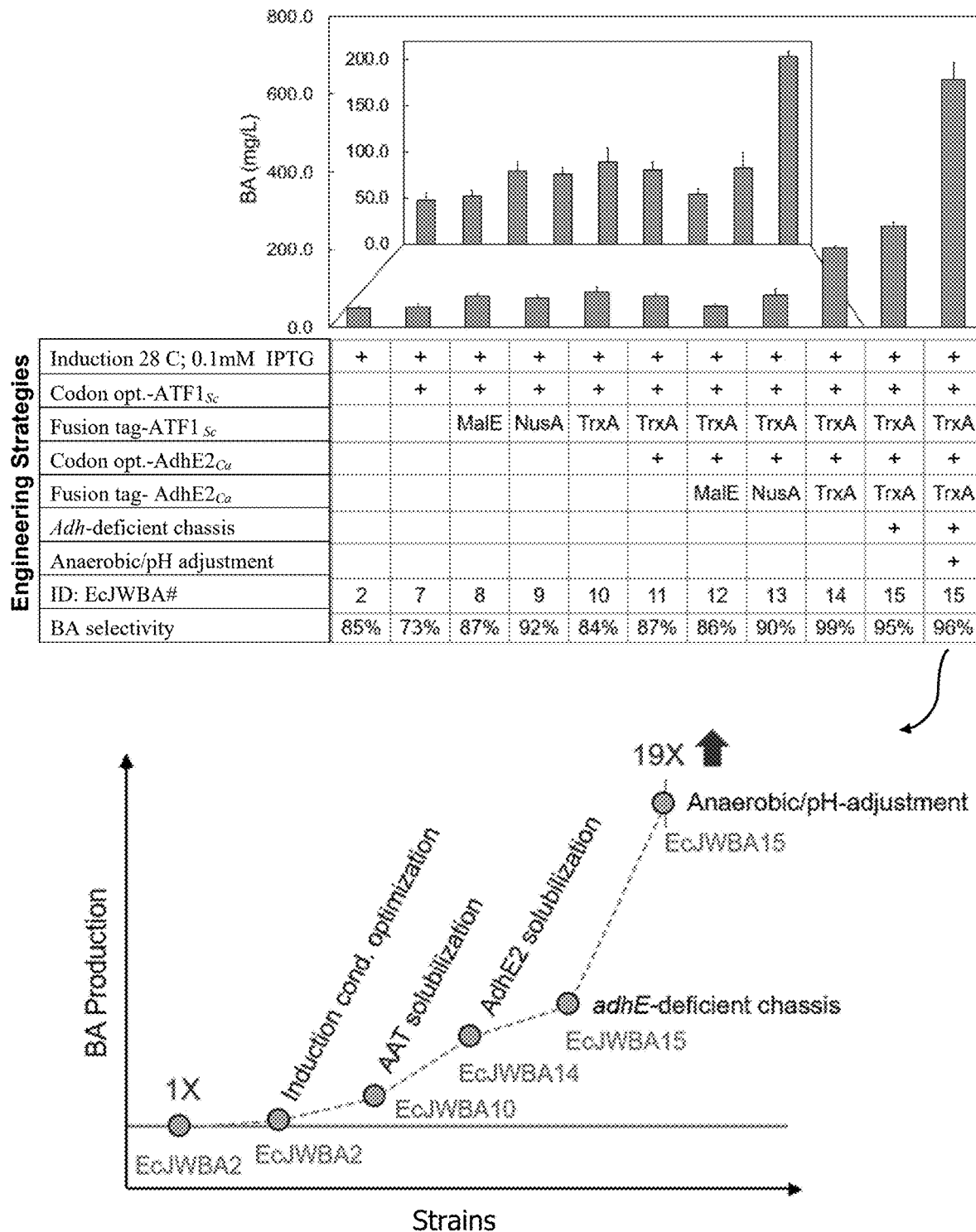
FIG. 17A is data in the form of a bar graph, chart and line graph for biosynthesis of butyl acetate from glucose in the strains identified in the chart.
Figure 17B:
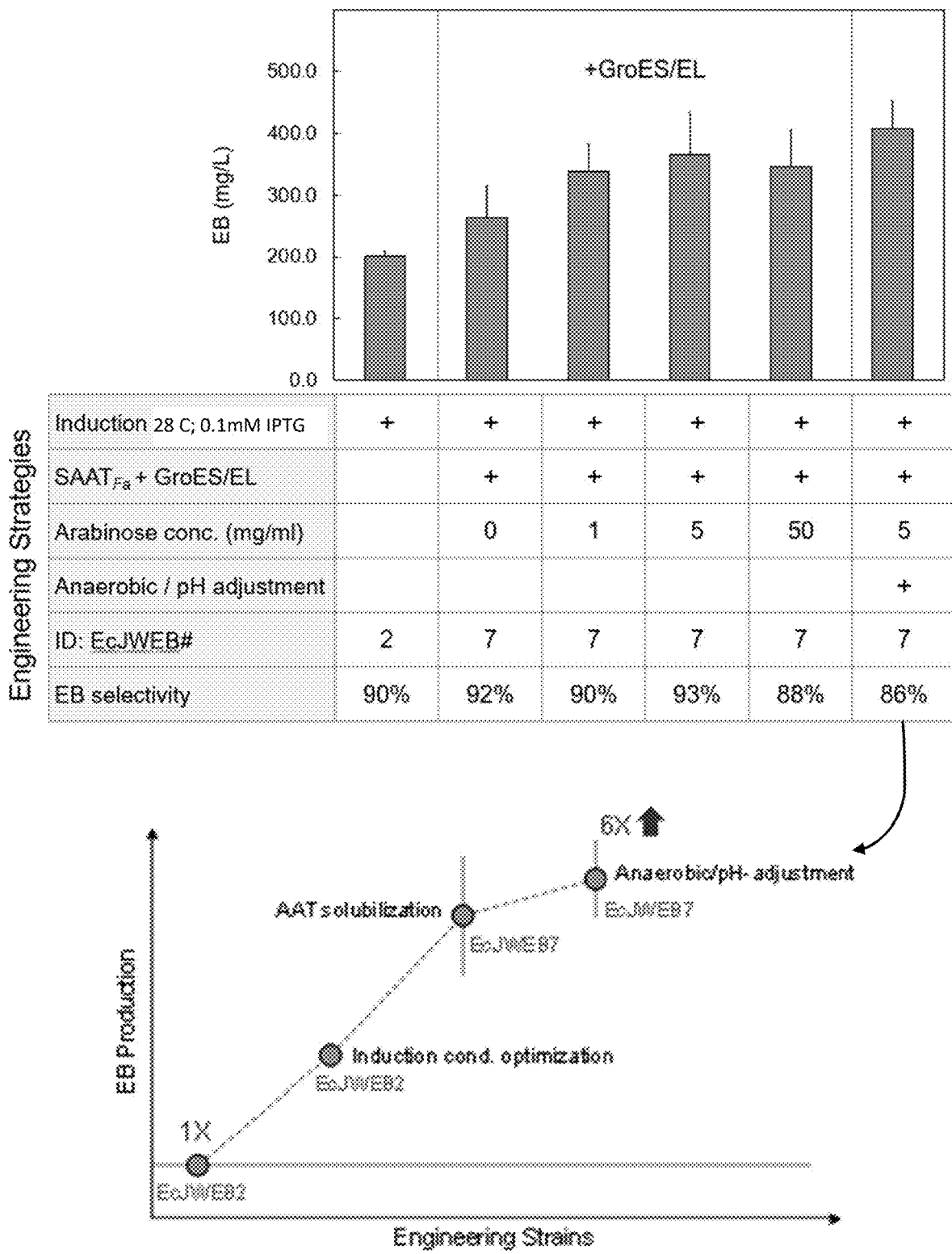
FIG. 17B is data in the form of a bar graph, chart and line graph for biosynthesis of ethyl butyrate from glucose in the strains identified in the chart.
Figure 17C:
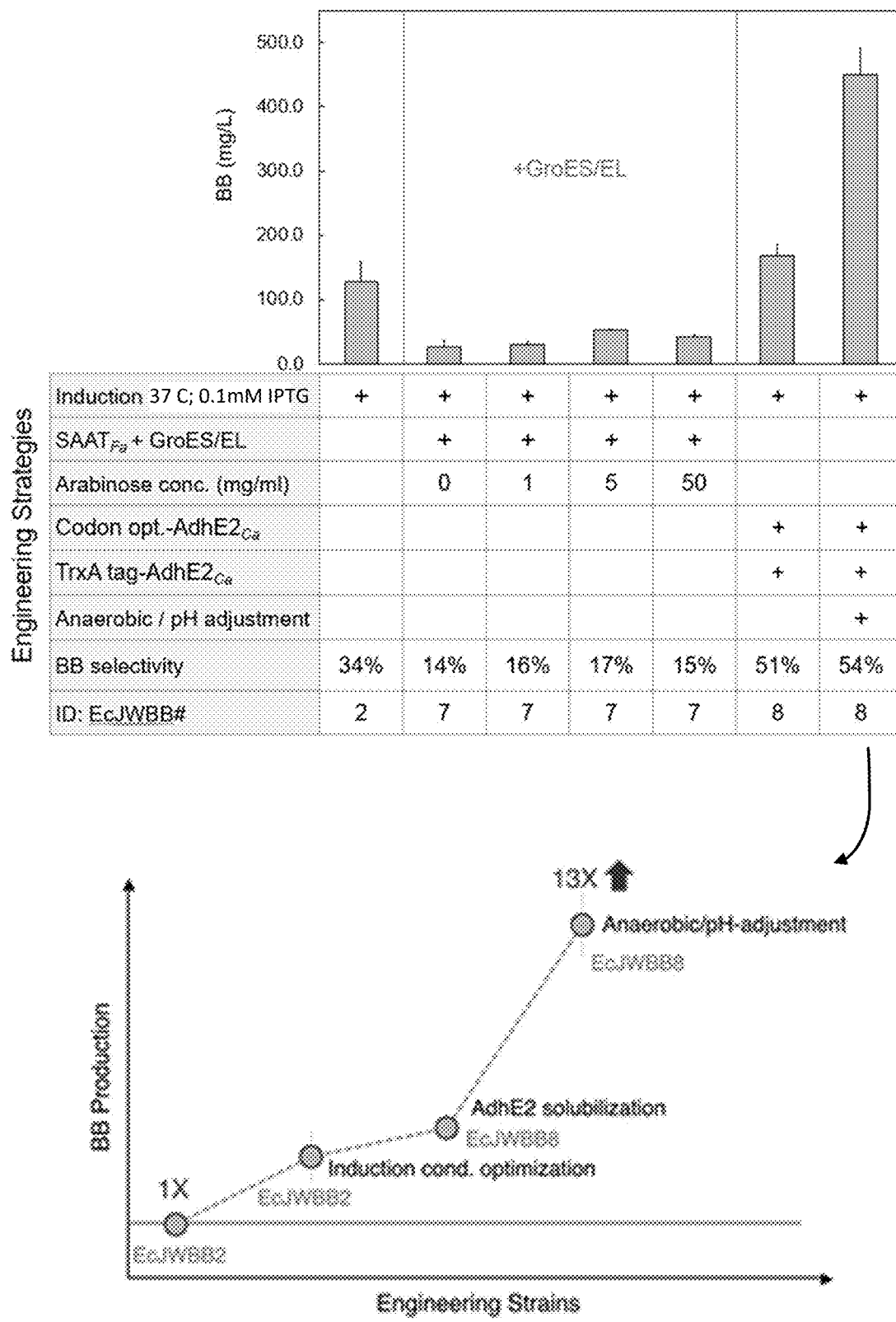
FIG. 17C is data in the form of a bar graph, chart and line graph for biosynthesis of butyl butyrate from glucose in the strains identified in the chart.

Referring now to FIGS. 17A-17C, the additive effects of induction conditions, improved solubility of the AAT and/or $AdhE2_{Ca}$, optionally an adhE-deficient chassis, and an anaerobic condition/pH adjustment is shown to greatly increase the concentration of the target ester. FIG. 17A shows the achievement of a 19-fold increase in BA production with 96% selectivity with induction conditions of 0.1 mM IPTG at 28° C., AAT and $AdhE2_{Ca}$ solubilization by codon configuration and fusion tag, an adhE-deficient chassis, and an anaerobic condition/pH adjustment. FIG. 17B shows the achievement of a 6-fold increase in EB production with 86% selectivity with induction conditions of 0.1 mM isopropyl β-D-1-thiogalactopyranoside (IPTG) at 28° C., AAT solubilization by coexpression of a chaperone Gro ES/EL, an arabinose concentration of 5 mg/ml, and an anaerobic condition/pH adjustment. FIG. 17C shows the achievement of a 13-fold increase in BB production with 54% selectivity, as compared to the initial strains, with induction conditions of 0.1 mM isopropyl β-D-1-thiogalactopyranoside (IPTG) at 37° C., $AdhE2_{Ca}$ solubilization by codon configuration and fusion tag, and an anaerobic condition/pH adjustment.

Unlike the microbial biosynthesis of BA and EB, tuning the BB selectivity is intrinsically challenging due to the following reasons: i) the butanol biosynthesis is limiting due to low solubility of $AdhE_{Ca}$ and ii) $AdhE_{Ca}$ is promiscuous and can reduce both acetyl-CoA and butyryl-CoA. While our strategy to enhance co-solubilization of $AdhE_{Ca}$ together with $SAAT_{Fa}$ helped improve BB production and selectivity, EB is always produced as a significant byproduct. Should high selectivity be desirable for specific applications, two engineering strategies can be further exploited to overcome this problem: i) improving specificity of $AdhE_{Ca}$ towards butyryl-CoA and ii) decoupling butanol and butyl butyrate production using a microbial co-culture system. Furthermore, without external supply of butanol, production of BA and BB directly from glucose was much lower likely due to metabolic burden required for expressing multiple pathway enzymes.

One distinct advantage of microbial production of esters is that they have low solubility in an aqueous phase and hence are very beneficial for fermentation. Even though the butyryl-CoA-derived esters are inhibitory to microbes, their toxicity is significantly alleviated by implementing in situ fermentation and extraction. Besides beneficial detoxification by extraction, we also found that maintaining anaerobic culture conditions at neutral pH control improves ester production. Anaerobic production of butyryl-CoA-derived esters from fermentable sugars are favorable because i) high product yields can be achieved due to higher reduction of esters than glucose and ii) scale-up for anaerobic processes is much simpler and more economical.

In conclusion, we developed a generalizable framework to engineer a modular microbial platform for anaerobic production of butyryl-CoA-derived designer esters. Using the principles of modular design, we engineered the de novo modular fermentative pathways of biosynthesis of BA, EB, and BB from fermentable sugars in E. coli with controllable selectivity. In addition to the conventional strategies of replication and transcription manipulation, implementing various protein solubilization strategies on aggregate-prone pathway enzymes to control enzyme (post)-translation is important to enhance ester production and selectivity. We envision the modular microbial ester synthesis method will accelerate the biosynthesis of diverse natural esters with various industrial applications.

Working Example 1

Strains and Primers: E. coli TOP10 was used for molecular cloning while BL21 (DE3) or EcDL002 was used as a host strain for ester production. The pETDuet-1 plasmids containing 20 F97 variants of $CAT_{Sa}$ were used to examine the role of the F97 residue on the alcohol substrate preference. F97 is present in the binding pocket of the CAT. The plasmid $pATF1_{Sc}$ was constructed by subcloning $ATF1_{Sc}$ gene from pDL004 into pET29 by the Gibson gene assembly method. The $ATF1_{Sc}$ variants were generated by the known technique of site-directed mutagenesis. The plasmid $pSAAT_{Fa}$ was constructed to harbor the codon optimized $SAAT_{Fa}$ gene for E. coli. All the constructed plasmids were verified by Sanger sequencing and introduced into the host strains by chemical transformation. The primers used in herein correspond to SEQ ID Nos. 1-28 and the codon optimized sequences of $SAAT_{Fa}$ for E. coli is SEQ ID No. 29. Mutations are defined using the standard one letter code for amino acids.

Culture media: A lysogeny broth (LB) medium comprising 10 g/L peptone, 5 g/L yeast extract, and 5 g/L NaCl was used for molecular cloning and seed cultures. An M9 hybrid medium with 20 g/L glucose was used for ester production. Either 50 μg/mL ampicillin (Amp) or 50 μg/mL kanamycin (Kan) was added to the media for selection where applicable.

Microplate-based microbial screening: Cell inoculum was prepared either from a bacterial glycerol stock or from a single colony on a LB agar plate. Specifically, 1% (v/v) of stock cells were grown overnight in 5 mL of LB at 37° C. and 200 rpm on a 75° angled platform in a New Brunswick Excella E25 (Eppendorf, CT, USA). Alternatively, single colonies from LB agar plates were inoculated in 100 μL of LB in 96-well microplates using sterile pipette tips. Each colony picked by a sterile pipette tip was subsequently mixed with the media in the target well and was grown overnight at 37° C. and 400 rpm in an incubating microplate shaker (cat #02-217-757, Fisher Scientific, PA, USA).

For the microplate-based screening assay, 5% (v/v) of overnight cultures were first inoculated in 100 μL of the M9 hybrid media containing 20 g/L of glucose, 0.1 mM of isopropyl β-D-1-thiogalactopyranoside (IPTG), and 2 g/L of alcohol (i.e., ethanol, n-butanol, isobutanol, isoamyl alcohol, hexanol, or 2-phenethyl alcohol) in 96-well microplates with hexadecane overlay in a 1:1 (v/v) ratio. The microplates were then sealed with a plastic adhesive sealing film, Scal-Plate® (cat #STR-SEAL-PLT, EXCEL Scientific, Inc., CA, USA), to avoid cross contamination and evaporation using a plate roller (cat #RLPLT01, Andwin Scientific, CA, USA). Finally, the microplates were incubated at 37° C. and 400 rpm for 24 hours (h) in an incubating microplate shaker.

The optical density (OD) of cell culture was measured at 600 nm using a spectrophotometer (GENESYS 30, Thermo Scientific, IL, USA) or BioTek Synergy HT microplate reader (BioTek Instruments, Inc., VT, USA). A correlation between the $OD_{600}$ and dry cell weight (DCW) (1 $OD_{600}$=0.476 g DCW/L) was determined by centrifugation of a known volume of the culture broth, sediment drying, and posterior weighing. The dry cell mass (DCW) was obtained by multiplication of the optical density of culture broth with a conversion factor, 0.48 g/L/OD. The organic layers were collected for ester measurement either by gas chromatography coupled with mass spectroscopy (GC/MS) or colorimetric assay.

Comparative gas chromatography coupled with mass spectroscopy (GC/MS): For comparison against the trial herein, microplates from the microbial screening of AATs were centrifuged at 4,800×g for 5 min and the hexadecane overlays were used for quantification of esters. The samples were prepared by diluting hexadecane extracts from the cultures with hexadecane containing internal standard (isoamyl alcohol) in a 1:1 (v/v) ratio. Then, 1 μL of samples were directly injected into a gas chromatograph (GC) HP 6890 equipped with the mass selective detector (MS) HP 5973. For the GC system, helium was used as the carrier gas at a flow rate of 0.5 mL/min and the analytes were separated on a Phenomenex ZB-5 capillary column (30 m×0.25 mm×0.25 μm). The oven temperature was programmed with an initial temperature of 50° C. with a 1° C./min ramp to 58° C. Next a 25° C./min ramp was deployed to 235° C., then a 50° C./min ramp was deployed to 300° C., and finally the temperature at 300° C. was held for 2 minutes to elute any residual non-desired analytes. The injection was performed using the splitless mode with an initial injector temperature of 280° C. For the MS system, a selected ion monitoring (SIM) mode was deployed to detect analytes. The SIM parameters for detecting esters were as follows: i) for ethyl acetate, ions 45.00, and 61.00 detected from 4.15 to 5.70 min, ii) for isoamyl alcohol (internal standard), ions 45.00, and 88.00 detected from 5.70 to 7.20 min, iii) for isobutyl acetate, ions 61.00, and 101.00 detected from 6.60 to 7.75 min, iv) for butyl acetate, ions 61.00, and 116.00 detected from 7.75 to 13.70 min, v) for 2-phenethyl acetate, ions 104.00, and 121.00 detected from 13.70 to 13.95 min, vi) for ethyl butyrate, ions 47.00, and 116.00 detected from 7.20 to 7.75 min, and vii) for butyl butyrate, ions 101.00, and 116.00 detected from 11.25 to 12.50 min.

Experimental colorimetric assay: The colorimetric assay for ester quantification was performed in a 96-well microplate. In each well, 40 μL of hexadecane overlay from the culture was mixed with 40 μL of hydroxylamine stock solution and incubated at room temperature for 10 minutes (min) to produce hydroxamic acid. Next, 120 μL of the ferric working solution (1/20-diluted stock ferric iron (III) solution in ethanol) was added to the reaction solution and incubated for 5 min to form an iron-hydroxamic acid complex. The absorbance was measured at 520 nm ($Ab_{520}$) using a BioTek Synergy HT microplate reader. Esters were quantified using a standard curve between the absorbances and known concentrations of a target ester.

Results: IBA production in microplates followed the same trend of its production observed in high cell density cultures with a strong positive linear correlation ($R^2$≥0.965) in IBA production between the microplate-based and high cell density culturing methods. Thus, the microplate-based culturing method could validate that the $CAT_{Sa}$ F97W variant achieved the highest IBA production among a set of 20 characterized variants.

Working Example 2

Figure 8:
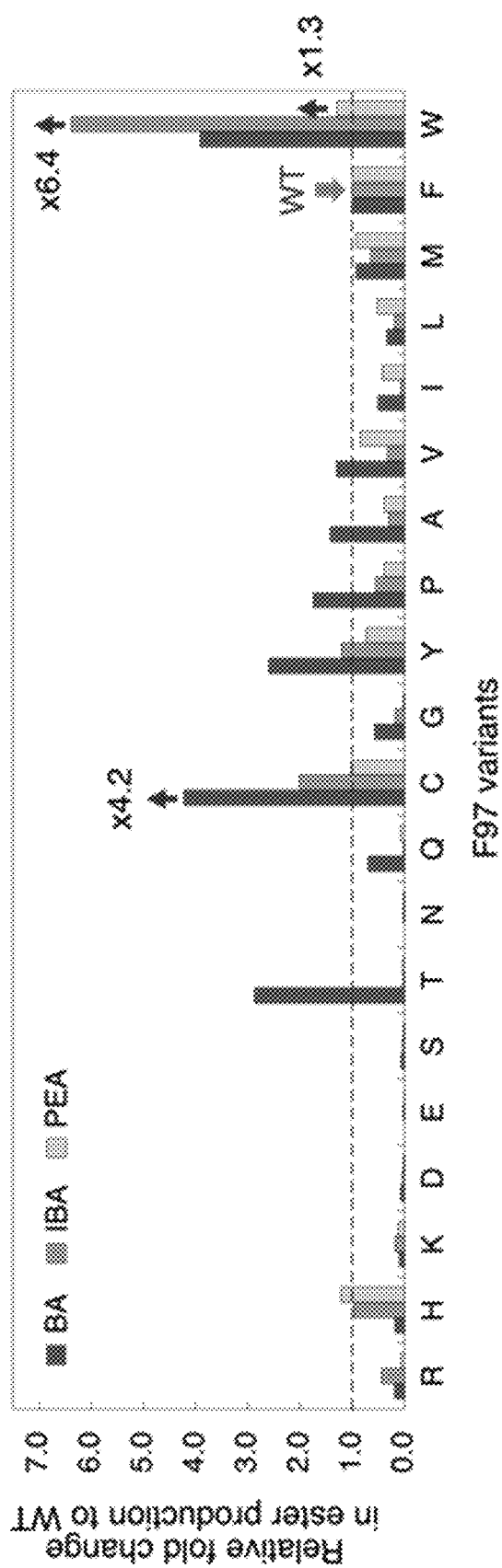
FIG. 8 is a bar graph of relative fold change in ester production of CAT$_{Sa}$ F97 variants with respect to the wildtype.

Our previous work discovered that the $CAT_{Sa}$ F97W mutant improved its catalytic efficiency towards isobutanol by about 2-fold. Using the microplate-based method disclosed herein, rapid profiling of the alcohol substrate preference of $CAT_{Sa}$ F97 variants was evaluated. We characterized the recombinant E. coli BL21 (DE3) strains carrying 20 $CAT_{Sa}$ F97 variants with exogenous supplementation of alcohols in the media including linear, short-chain alcohols (ethanol, butanol), a branched-chain alcohol (isobutanol), and an aromatic alcohol (2-phenethyl alcohol) in microplates with hexadecane overlay. Referring now to the graph provided as FIG. 8, the results show that mutations in the F97 residue changed the ester production profiles. FIG. 8 report the relative fold change in ester product as compared to the wildtype (WT) for n-butyl acetate (BA), isobutyl acetate (IBA), and 2-phenethyl acetate (PEA). Ethyl acetate is not included in FIG. 8 because each of the variants exhibited poor activity toward ethanol. Thus, the F97 residue plays an important role in determining the alcohol substrate preference of $CAT_{Sa}$.

Still referring to FIG. 8, among the four target acetate esters investigated, F97W produced PEA at the highest level of 194.6 mg/L followed by F97H (182.3 mg/L) and the wildtype F97 (149.4 mg/L). As compared to the wildtype, IBA production by F97W (91.2 mg/L) showed the highest improvement (~6.4-fold), which was relatively consistent with a prior in vitro study showing that F97W variant achieved ~2-fold increase in the catalytic efficiency towards isobutanol. Remarkably, F97T showed BA production (12.4 mg/L) with high specificity, demonstrating the feasibility of production of designer esters using selectively modified CATs. Different from F97W, F97C exhibited the highest BA production (18.3 mg/L).

Working Example 3: Rapid Search for the Engineered $ATF1_{Sc}$ Mutants for Enhanced n-Butyl Acetate Production and/or Selectivity Using the Disclosed Method A library of potential $ATF1_{Sc}$ candidates in silico were generated that might improve BA production, which involved creating a 3D structure of $ATF1_{Sc}$ using the homology model of 15-O-acetyltransferase (PDB: 3FP0) best predicted by SWISS-MODEL, and identifying a binding pocket of $ATF1_{Sc}$ for docking simulations of the BA co-substrates, including acetyl-CoA and butanol. Based on the homology model, the binding pocket of $ATF1_{Sc}$ consists of 24 residues including V32, Y36, H191, D195, G196, R197, T316, I347, P348, A349, D350, R352, N370, V371, I374, F376, Y399, I403, L407, K426, L448, S449, N450, V451, F471, and Q473, where H191 and D195 are the catalytic residues. By performing docking simulations, an acetyl-CoA-butanol-$ATF1_{Sc}$ complex was generated and the residues interacting with butanol including V32, Y36, D195, P348, V371, L447, S449, Q473, Q475, and S483 were identified. Lastly, a residue scan against these 10 residues was performed to select the top nine promising candidates including P348W, P348R, P348M, P348H, P348K, P348N, P348I, P348S, and P348D with low Δaffinity values for experimental characterization.

The high-throughput microbial screening method disclosed in working example 1 was implement for the top nine engineered ATF1$_{Sc}$ candidates. TCS083 ΔfadE (DE3) was selected as a host strain. Since BA is being evaluated, a standard colorimetric curve was prepared. Like the colorimetric assay developed for IBA, the standard curve for BA measurement showed a strong linear correlation ($R^2$=1.000) between the 520 nm absorbance and the standard BA concentrations in the range of 0-200 mg/L. Unfortunately, as shown in FIG. 3, no positive improvement in BA production was evidence by any of the variants for ATF1$_{Sc}$ P348 variants.

Since the P348 residue of ATF1$_{Sc}$ is located on the opposite side of the catalytic residues (H191 and D195) and interacts with an alcohol substrate, it is believed that the P348 residue may have an important role in determining the alcohol substrate preference of ATF1$_{Sc}$ like the F97 residue of CAT$_{Sa}$. To evaluate whether the mutations of the ATF1$_{Sc}$ P348 affected the alcohol substrate preference, we characterized the recombinant *E. coli* strains carrying the ATF1$_{Sc}$ P348 variants using our established high-throughput microbial screening platform with exogenous supplementation of various alcohols including linear, short-to-medium chain alcohols (ethanol, hexanol), a branched-chain alcohol (isoamyl alcohol), and an aromatic alcohol (2-phenethyl alcohol). The screening results of FIGS. 3 and 4 show that the mutations of the P348 residue changed the ester production profiles while the ATF1$_{Sc}$ P348 variants exhibited similar protein expression levels. Specifically, both P348K and P348N almost lost their activities towards butanol, isoamyl alcohol, hexanol, and 2-phenethyl alcohol but remained active towards ethanol. Unlike P348K and P348N, P348M maintained its activity towards 2-phenethyl alcohol while its activities towards ethanol, butanol, isoamyl alcohol, and hexanol were reduced. These results suggest that the P348 residue plays an important role in determining the alcohol substrate preferences of ATF1$_{Sc}$.

Figure 3:
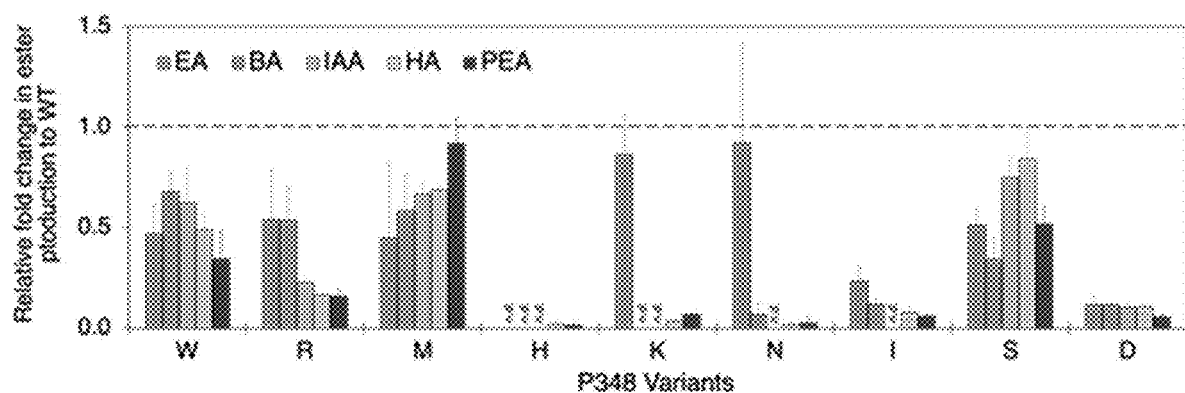
FIG. 3 is a bar graph of relative fold change in ester production for determining alcohol substrate preference of an AAT, such as ATF1$_{Sc}$ P348 variants as compared to its wildtype (WT).

Still referring to FIG. 3, since P348K and P348N showed dramatic change in their alcohol substrate preference, we compared the 3D structure of ethanol-bound P348K or P348N against its wildtype. Interestingly, the results showed that both P348K and P348N form a hydrogen bond with ethanol residue. This interaction might help the binding of ethanol into the binding pocket of ATF1$_{Sc}$ while blocking the binding of the bigger alcohol substrates due to the steric hindrance. The results showed that ATF1$_{Sc}$ wildtype preferred bulky alcohol substrates such as IAA, HA, and PEA.

Working Example 4

Figure 9:
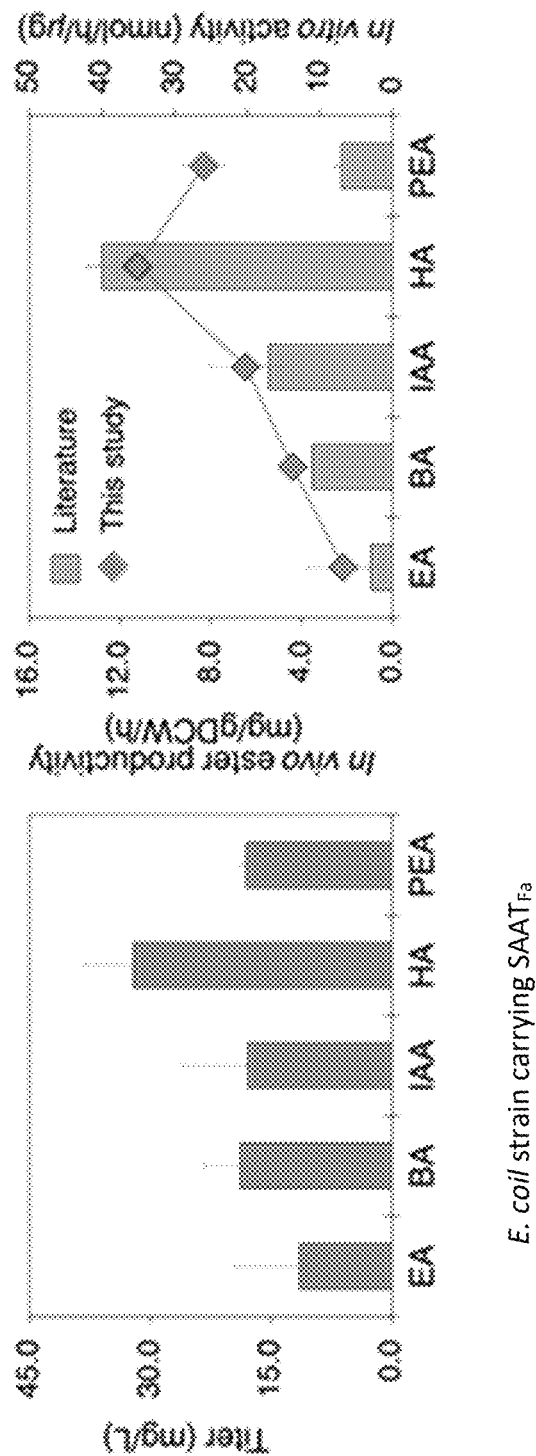
FIG. 9 is a bar graph of ester production by the *E. coli* strain carrying SAAT$_{Fa}$ alone and then as a comparison against in vitro activity thereof from literature.

The activities of SAAT$_{Fa}$ against different alcohol substrates was characterized using the procedure of working example 1 and the method disclosed herein. A recombinant *E. coli* strain carrying the SAAT$_{Fa}$ was made and characterized using the high-throughput microbial screening method with exogenous supplementation of various alcohols including linear, short-to-medium chain alcohols (ethanol, butanol, hexanol), a branched-chain alcohol (isoamyl alcohol), and an aromatic alcohol (2-phenethyl alcohol). Referring to FIG. 9, the results show that the recombinant *E. coli* strains carrying the SAAT$_{Fa}$ produced 11.4±8.1 mg/L of ethyl acetate (EA), 18.8±4.6 mg/L of butyl acetate (BA), 17.9±8.2 mg/L of isoamyl acetate (IAA), 32.1±6.2 mg/L of hexyl acetate (HA), and 18.1±0.8 mg/L of PEA (2-phenethyl acetate). The in vivo activity (specific ester productivity, mg/gDCW/h) for each ester produced was calculated and compared to its respective in vitro activity from the literature. Interestingly, except for 2-phenethyl alcohol, the alcohol substrate preference of SAAT$_{Fa}$ showed a strong linear correlation ($R^2$=0.996) between the in vivo and in vitro activity.

For 2-phenethyl alcohol, we believe that its high toxicity led to the gap between the in vivo and in vitro experimental results. This demonstrates that the high-throughput microbial screening method disclosed herein enables not only probing the alcohol substrate preference of an AAT, but also examining the effect of the alcohol substrate toxicity on ester productivity which in vitro characterization cannot offer.

Working Example 5: Detectable Concentration Range Limits

Figure 10:
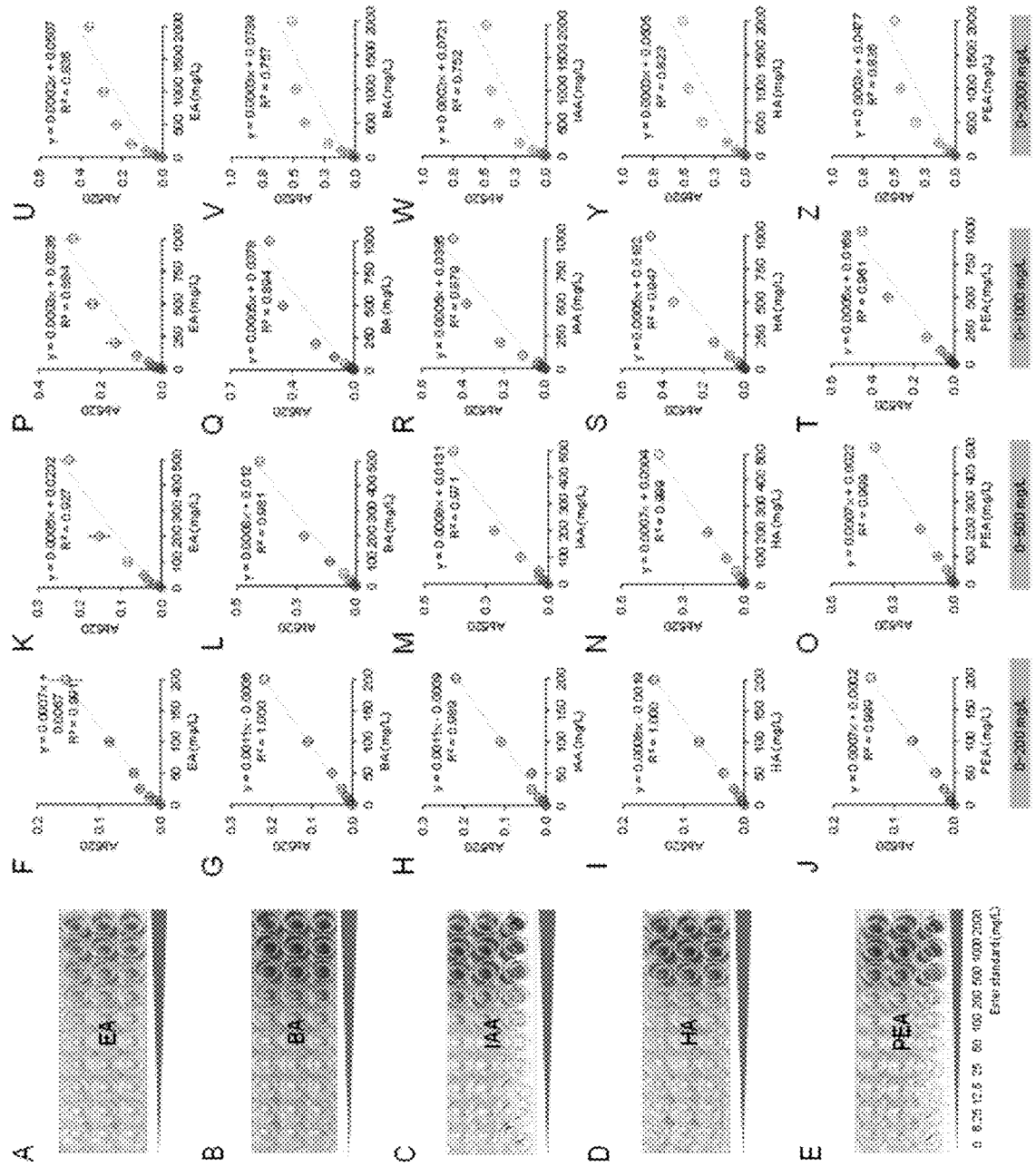
FIG. 10 is a compilation of standard colorimetric curves for various esters at varying (increasing) concentration ranges.

Referring to FIG. 10, the detectable concentration range of various esters including ethyl acetate (EA), butyl acetate (BA), isoamyl acetate (IAA), hexyl acetate (HA), and 1-phenethyl acetate (PEA) were examined by generating their standard curves at different concentrations (letter F-Z in the figure). The different concentrations being 0-200 mg/L, 0-500 mg/L, 0-1000 mg/L, and 0-2000 mg/L. The colorimetric assay results show that the standard curve for ester measurement had a strong linear correlation ($R^2$≥0.989) between the 520 nm absorbance and the standard concentrations in the range of 0~200 mg/L. However, as the concentration range increased, the correlation decreased. The correlation was significantly reduced ($R^2$≥0.752) when the standard concentrations were tested in the range of 0~2000 mg/L.

Still referring to FIG. 10, the esters showed different detectable concentration ranges ($R^2$≥0.95) based on their molecular structures. Among the ester standards examined, PEA (aromatic ester) showed the broadest detectable concentration range of 0~2000 mg/L, followed by BA, IAA, and HA (linear/branched medium-chain ester) with a range of 0~1000 mg/L. EA (linear short-chain ester) showed the narrowest detectable concentration range of 0~500 mg/L. This suggests that the longer or aromatic esters have a broader detectable concentration range in the colorimetric assay than shorter or aliphatic esters. Thus, it is recommended to use the ester standard curves with the standard concentrations in the range of 0~200 mg/L to measure the accurate ester concentrations in the samples using the colorimetric assay.

Working Example 6

Strains and Primers: *E. coli* TOP10 was used for molecular cloning. Referring now to FIG. 12, TCS083 ΔfadE was used as a host strain, except for EcJWBA15 for which TCS095 (DE3) was used. A set of duet vectors including pACYCDuet-1, pETDuet-1, and pRSFDuet-1 were used as plasmid backbones for constructing a library of BA, EB, and BB production modules. The codon-optimized *S. cerevisiae* ATF1 (ATF1$_{Sc}^{opt}$), cultivated strawberry (*F. ananassa*) SAAT (SAAT$_{Fa}^{opt}$), *Candida boidinii* fdh (fdh$_{Cb}^{opt}$), and *C. acetobutylicum* adhE2 (adhE2$_{Ca}^{opt}$). The list of codon optimized gene sequences are SEQ ID NOS: 30-33.

Culture conditions: For molecular cloning and seed cultures, lysogeny broth (LB) was used. For ester production, $TBD_{50}$ medium, terrific broth (TB) with 50 g/L glucose was used (without supplementation with glycerol). For all cultures, 30 µg/mL chloramphenicol (Cm), 50 µg/mL kanamycin (Kan), and/or 100 µg/mL ampicillin (Amp) were added to the medium where applicable.

For seed cultures, 1% (v/v) of stock cells were grown overnight in 5 mL of LB medium with appropriate antibiotics. For ester production in capped conical tubes, seed cultures were prepared as described in seed cultures. About 1% (v/v) of seed cultures were inoculated in 500 mL baffled flasks containing 50 ml of $TBD_{50}$ medium with appropriate antibiotics. The cells were aerobically grown in shaking incubators at 28° C. or 37° C., 200 rpm and induced at an $O.D._{600}$ of 0.6~0.8 with various concentrations of IPTG (0.01 mM, 0.1 mM, ands 1.0 mM), arabinose (if applicable), and/or 5 ng/ml of tetracycline (if applicable). After 2 hours of induction, the cultures in the baffled flasks were distributed into 15 mL conical centrifuge tubes (Cat. #339650, Thermo Scientific, MA, USA) with a working volume of 5 mL. Then, each tube was overlaid with 1 mL hexadecane (20% (v/v)) for in situ ester recovery and capped to generate anaerobic conditions. Finally, the tubes were grown for another 18 hours on a 75° angled platform in shaking incubators at 28° C. or 37° C., 200 rpm. The remained cultures in the baffled flasks were induced for further 2 hours and then the cells were harvested for SDS-PAGE analysis.

Anaerobic/pH adjustment: For ester production in strict anaerobic bottles with pH-adjustment, the induced cultures were prepared as described in ester production in conical tubes with a working volume of 100 mL. To generate the anaerobic state, the induced cultures were transferred into anaerobic bottles. Then, each anaerobic bottle was overlaid with 20% (v/v) of hexadecane for in situ ester recovery and sealed with a rubber stopper inside the anaerobic chamber. The headspace of the anaerobic bottles was vacuumed and replaced by an anaerobic mix of 90% $N_2$, 5% $H_2$, and 5% $CO_2$ inside the anaerobic chamber. Finally, the anaerobic bottles were grown for another 90 hours in shaking incubators at 28° C. or 37° C., 200 rpm. The culture medium and hexadecane overlay samples were taken through the rubber stopper via a syringe and needle by maintaining the ratio of 5:1. The culture pH was adjusted to 7 using 10 M NaOH every 24 hours.

Protein expression and SDS-PAGE analysis. The cells were collected from the culture by centrifugation and resuspended in 1×PBS (Phosphate Buffered Saline) buffer (pH 7.4) at the final $OD_{600}$ of 10. Cell pellets were disrupted using the B-PER complete reagent (Cat. #89822, Thermo Scientific, MA, USA), according to the manufacturer's instruction. Total and soluble fractions were separated by centrifugation for 20 min at 4° C. The resulting samples were mixed with 6×SDS (sodium dodecyl sulfate) sample buffer, heated at 95° C. for 5 min, and analyzed by SDS-PAGE (SDS-polyacrylamide gel electrophoresis) using Novex™ 14% Tris-Glycine protein gels (Cat. #XP00145BOX, Thermo Scientific, MA, USA). Protein bands were visualized with Coomassie Brilliant Blue staining.

Optical density measurements and GC/MS were performed in accordance with working example 1. Metabolites and doped alcohols were quantified by using the Shimadzu high performance liquid chromatography (HPLC) system (Shimadzu Inc., MD, USA) equipped with the Aminex HPX-87H cation exchange column (BioRad Inc., CA, USA) heated at 50° C. A mobile phase of 10 mN $H_2SO_4$ was used at a flow rate of 0.6 mL/min. Detection was made with the reflective index detector (RID).

Working Example 7: Testing Induction Conditions with the Best Identified Ester Producers, EcJWBA2, EcJWEB2, and EcJWBB2

Two temperatures (28° C. and 37° C.) and three concentrations of the inducer (0.01, 0.1, and 1.0 mM) isopropyl β-D-1-thiogalactopyranoside (IPTG) were tested. The results show that the titer of BA, EB, and BB was improved by 1.4, 2.8, and 3.8-fold, respectively. Specifically, for BA production, EcJWBA2 produced 48.0±7.1 mg/L of BA with the selectivity of 83.1% when it was induced by 0.1 mM of IPTG at 28° C., which is the induction condition used in the trial represented in FIG. 17A. For EB production, EcJWEB2 produced 200.4±9.4 mg/L of EB with the selectivity of 89.6% when it was induced by 0.1 mM of IPTG at 28° C., which is the induction condition used in the trial represented in FIG. 17B. For BB production, EcJWBB2 produced 127.4±32.5 mg/L of BB with the selectivity of 34.0% when it was induced by 0.1 mM of IPTG at 37° C.° C., which is the induction condition used in the trial represented in FIG. 17C.

Working Example 8: Protein Solubilization Strategies

Figure 18:
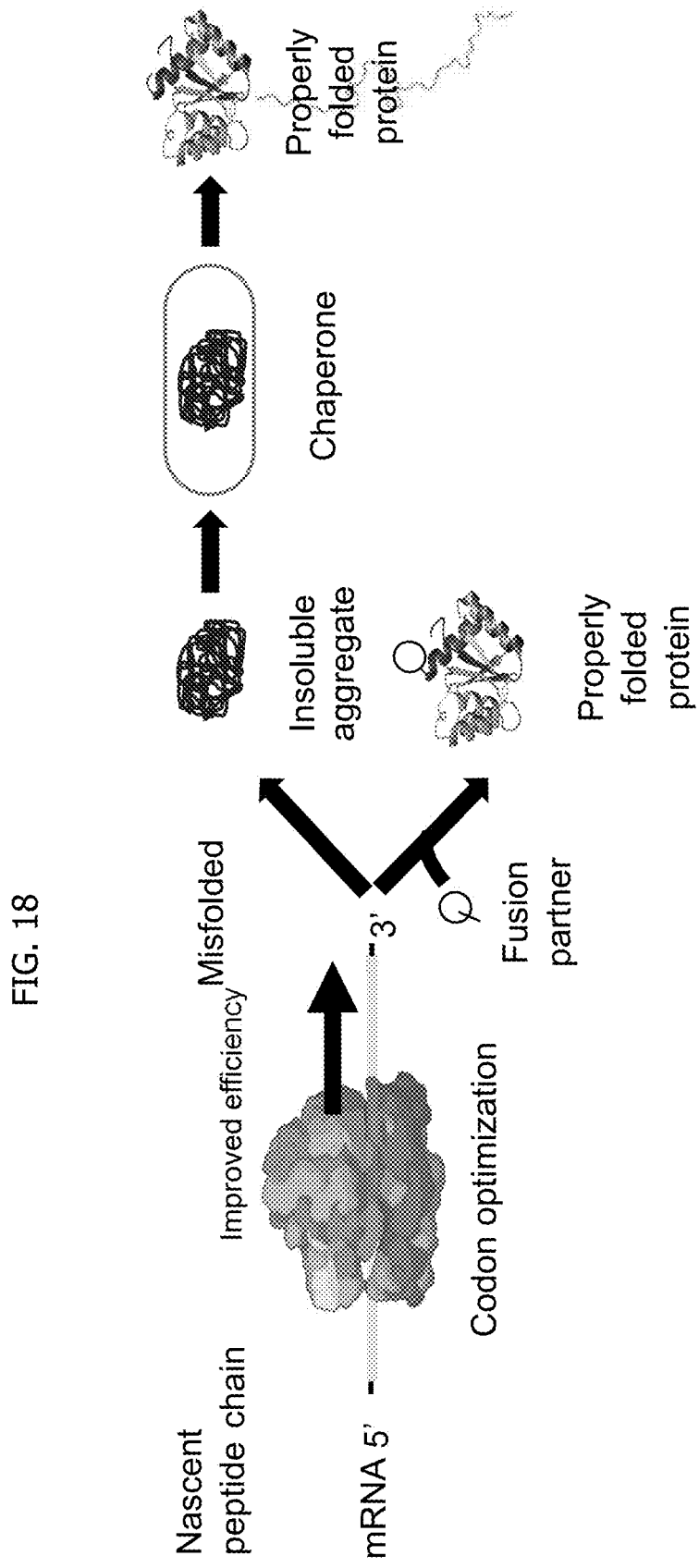
FIG. 18 is a schematic representation of protein solubilization strategies applied herein.

Since the protein bands of $ATF1_{Sc}$ and $SAAT_{Fa}$ are weaker than the other protein bands and these eukaryotic AATs are prone to poor expression in *E. coli*, Applicant believes that the AAT flux is one of the rate limiting steps and hence improving soluble expression of AATs would enhance the ester production. To examine the effect of AAT solubilization on ester production, we chose three strategies including i) codon optimization; ii) the use of fusion partners such as maltose binding protein without the N-terminus signal sequence, SEQ ID NO: 97 KIKTGARILALSAL-TTMMFSASALA (MBP), N-utilization substrate A (NusA), or thioredoxin 1 (TrxA); and iii) co-expression of molecular chaperones (DnaK/DnaJ/GrpE, GroES/GroEL, or Trigger factor (Tf)). A schematic representation of these effects on AATs is provided as FIG. 18, evidencing the end result of a properly folded protein.

To test whether AAT is a rate limiting step in isolation, the chassis cell was engineered to harbor only the acyl-CoA and AAT submodules and the alcohols were externally doped into the system. Plasmids were generated that harbor wild-type AATs, codon optimized AATs, fusion partner tagged AATs. For BA production, the plasmids carrying wildtype $ATF1_{Sc}$, codon optimized $ATF1_{Sc}$ ($ATF1_{Sc}^{opt}$), and N'-terminus MBP-, NusA-, or TrxA-tagged $ATF1_{Sc}$ (malE_$ATF1_{Sc}$, nusA_$ATF1_{Sc}$, or trxA_$ATF1_{Sc}$) were constructed and introduced into TCS083 ΔfadE (DE3), resulting in strains EcJWATF1, EcJWATF1$^{opt}$, EcJWATF1$^{MBP}$, EcJWATF1$^{NusA}$, EcJWATF1$^{TrxA}$, respectively (FIG. 12, second page). For EB and BB production, the plasmids carrying wildtype SAAT ($SAAT_{Fa}$), codon optimize $SAAT_{Fa}$ ($SAAT_{Fa}^{opt}$), and N'-terminus MBP-, NusA-, or TrxA-tagged $SAAT_{Fa}$ (malE_$SAAT_{Fa}$; nusA_$SAAT_{Fa}$; or trxA_S-$AAT_{Fa}$) were constructed and introduced into TCS083 ΔfadE (DE3) with the pACYCDuet-1 carrying the SM1 (butyryl-CoA pathway), resulting instrains EcJWSAAT, EcJWSAAT$^{opt}$, EcJWSAAT$^{MBP}$, EcJWSAAT$^{NusA}$, EcJWSAAT$^{TrxA}$, respectively (FIG. 12, second page). Then as shown in FIG. 13, to co-express chaperones with AATs, the chaperone plasmid set comprising of five different plasmids carrying various chaperones were introduced into EcJWATF1 and EcJWSAAT, resulting in EcJWATF1$^{Chp1}$~EcJWATF1$^{Chp5}$ and EcJWSAAT$^{Chp1}$~EcJWSAAT$^{Chp5}$.

The above engineered strains were placed in conical tubes with 2 g/L of alcohol doping including ethanol and butanol to evaluate the conversion of an alcohol (ethanol/butanol) into an ester (EA/BA) by ATF1$_{Sc}$ (FIG. 19) or EB/BB by SAAT$_{Fa}$ (FIG. 20), respectively. The cultures were induced by 0.1 mM of IPTG, 0.5 mg/ml of L-arabinose (if applicable) and/or 5 ng/ml of tetracycline (if applicable), and the protein expressions were confirmed by SDS-PAGE analysis. Still referring to FIGS. 19 and 20, the characterization results show that the protein solubilization strategies enhanced the conversion of an alcohol into an ester. Interestingly, different protein solubilization strategies worked effectively for different AATs. In particular, the codon optimization and use of a fusion partner (i.e., MBP, NusA, or TrxA) for ATF1$_{Sc}$ improved the BA conversion while co-expression of chaperones (i.e., GroES/EL, GroES/EL/Tf, or DnaK/DnaJ/GrpE/GroES/EL) with SAAT$_{Fa}$ enhanced the EB/BB conversion.

Figure 19:
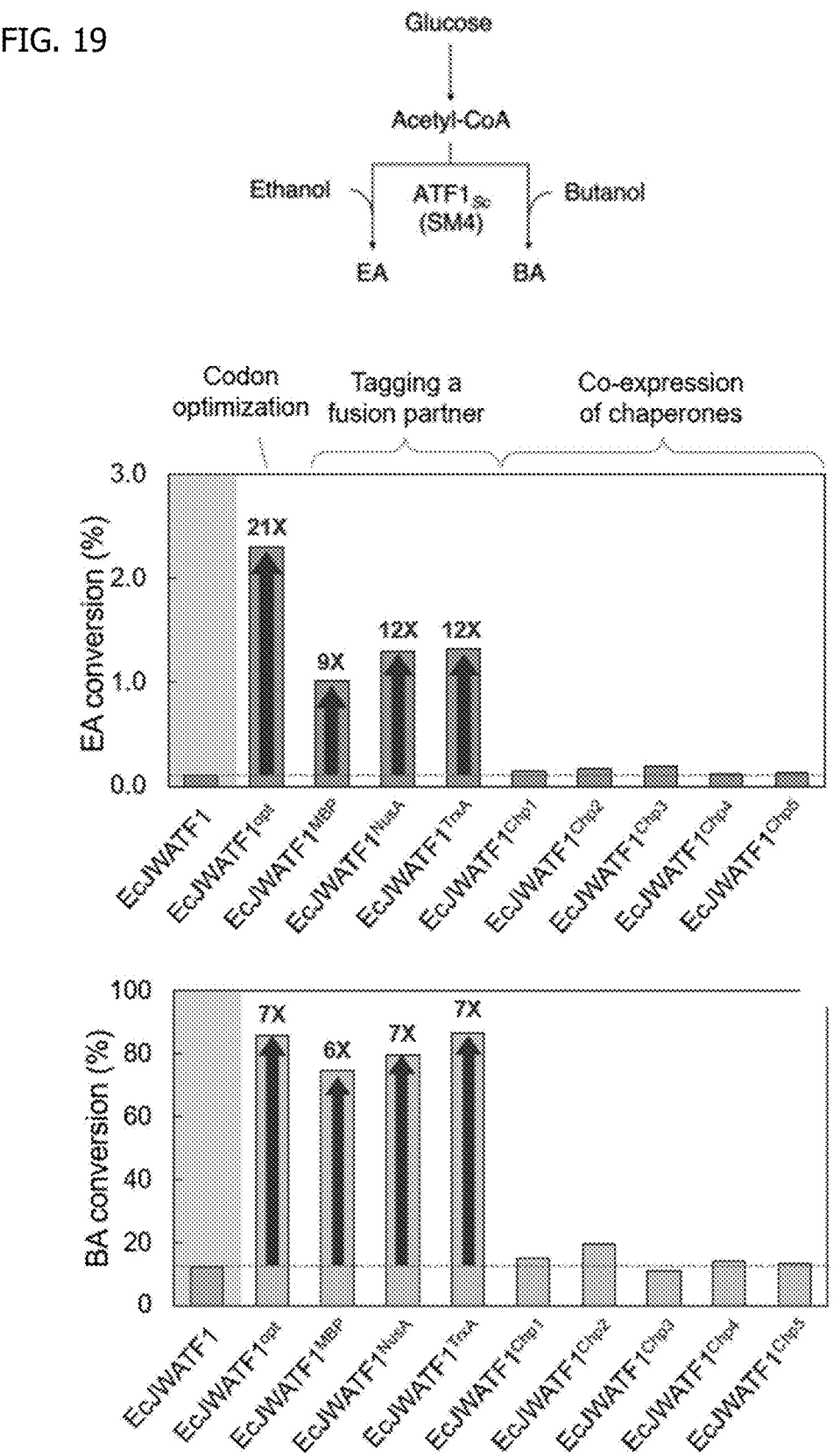
FIG. 19 is the pathway for ethyl acetate and butyl acetate production by ATF1$_{Sc}$ in *E. coli* and the ester conversion percentages for each strain relative to the solubilization strategy tested.

FIG. 19 shows that, for BA conversion, EcJWATF1$^{opt}$, EcJWATF1$^{MBP}$ EcJWATF1$^{NusA}$, EcJWATF1$^{TrxA}$ achieved 85.9%, 74.6%, 79.5%, and 86.6% of BA conversion, resulting in 7.1, 6.2, 6.6, and 7.2-fold improvement as compared to EcJWATF1 (12.0%), respectively. With 2 g/L butanol doping, the BA production could reach up to 2.26±0.22 g/L, and the selectivity of BA over other esters was as high as 98.1%.

Figure 20:
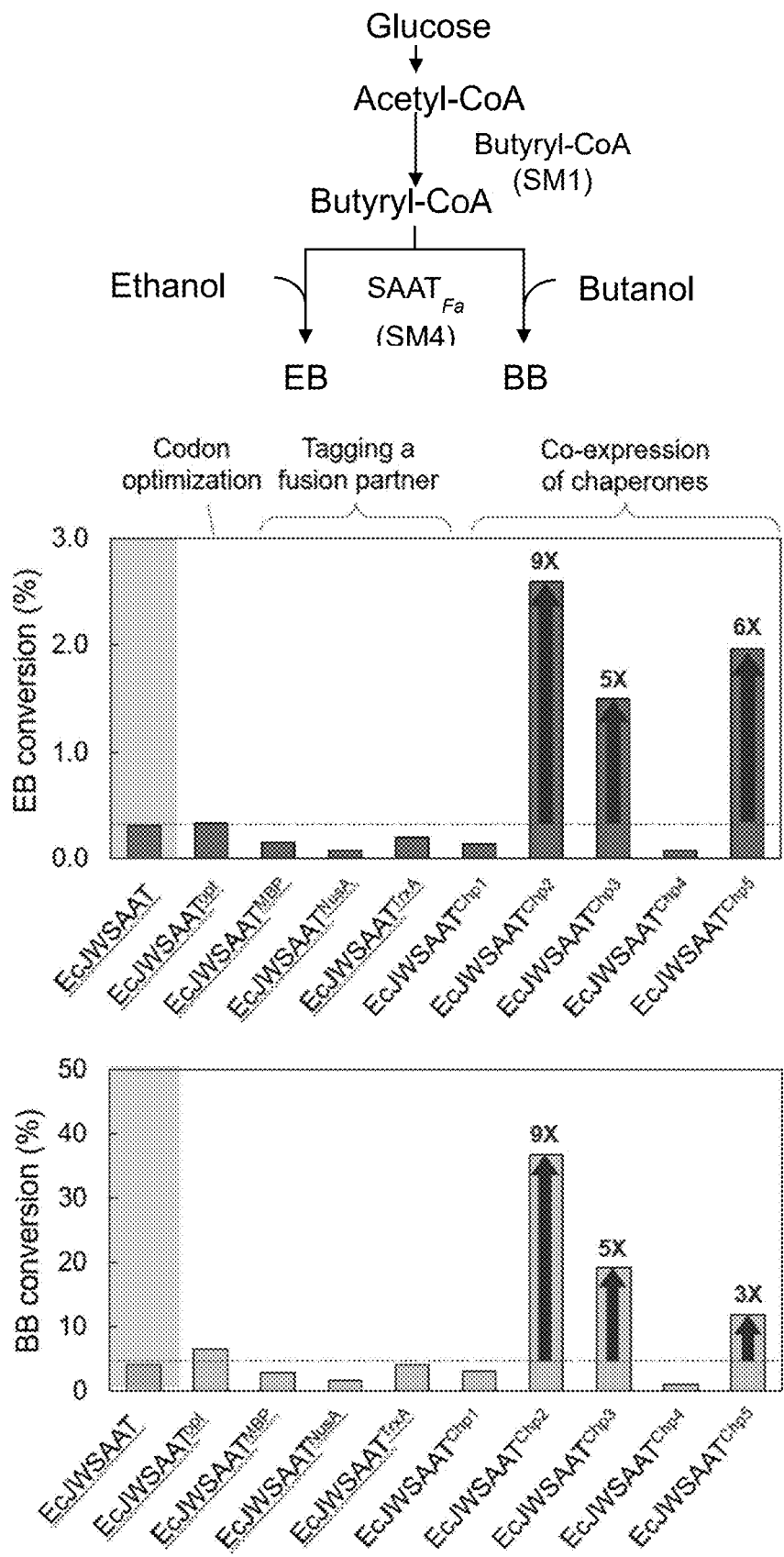
FIG. 20 is the pathway for ethyl butyrate and butyl butyrate production by SAAT$_{Fa}$ in *E. coli* and the ester conversion percentages for each strain relative to the solubilization strategy tested.

FIG. 20 shows that, for EB production, EB production was less prominent, only reaching up to 0.46±0.09 g/L with a selectivity of 86.3%. EcJWSAAT$^{Chp2}$, EcJWSAAT$^{Chp3}$, and EcJWSAAT$^{Chp5}$ achieved 2.6%, 1.5%, and 2.0% of EB conversion, leading to 8.5, 4.7, and 6.4-fold improvement as compared to EcJWSAAT (0.3%), respectively.

The metabolic burden in protein expressions and different catalytic efficiency between SAAT$_{Fa}$ and ATF1$_{Sc}$ likely contributed to the differences in strain performance. Still referring to FIG. 20, the BB production was reasonably high, reaching up to 1.71±0.26 g/L with a selectivity of 79.2%. EcJWSAAT$^{Chp2}$, EcJWSAAT$^{Chp3}$, and EcJWSAAT$^{Chp5}$ achieved 36.8%, 19.1%, and 11.9% of BB conversion, resulting in 9.0, 4.7, and 2.9-fold improvement as compared to EcJWSAAT (4.1%), respectively. Even though ATF1$_{Sc}$ and SAAT$_{Fa}$ have specificity towards longer-chain alcohols and acyl-CoAs, respectively, EA appeared as a minor byproduct. Referring again to FIG. 20, for the EA conversion, EcJWATF1$^{opt}$, EcJWATF1$^{MBP}$, EcJWATF1$^{NusA}$, EcJWATF1$^{TrxA}$ achieved 2.3%, 1.0%, 1.3%, and 1.3% of EA conversion, resulting in 20.5, 9.0, 11.7, and 11.8-fold improvement as compared to EcJWATF1 (0.1%), respectively. From the data, it can be concluded that AAT solubilization plays a critical role in controlling ester production and selectivity.

Working Example 9: AAT Solubilization and Ester Microbial Biosynthesis from Glucose Various BA, EB, and BB-producing strains were constructed and characterized using the techniques disclosed herein. For BA production, we first built four pRSFDuet-1 plasmids carrying SM2 (adhE2$_{Ca}$)-SM3 (fdh$^{opt}$)-SM4 (ATF1$_{Sc}^{opt}$, malE_ATF1$_{Sc}^{opt}$, nusA_ATF1$_{Sc}^{opt}$, or trxA_ATF1$_{Sc}^{opt}$), respectively, and then introduced them into the chassis cell TCS083 ΔfadE (DE3) with the pACYC-Duet-1 plasmid carrying the SM1 (butyryl-CoA pathway) to generate EcJWBA7~EcJWBA10, respectively (FIG. 12). For EB/BB production, we additionally introduced the plasmid carrying groES and groEL into EcJWEB2 and EcJWBB2, resulting in EcJWEB7 and EcJWBB7, respectively (FIG. 12). We characterized the engineered ester production strains in conical tubes for the endogenous ester production from glucose. For the expression of chaperones in EcJWEB2 and EcJWBB2, we also tested three different concentrations of L-arabinose as an inducer.

The characterization results show that the ATF1$_{Sc}$ solubilization indeed enhanced the endogenous BA production. Referring to FIG. 17A, EcJWBA7 to EcJWBA10 produced 51.7±7.1 mg/L, 79.3±9.8 mg/L, 76.1±6.2 mg/L, and 89.5±14.8 mg/L of BA, resulting in 1.1, 1.7, 1.6, and 1.9-fold improved BA production as compared to the EcJWBA2 (48.0±7.1 mg/L), respectively. Notably, because EcJWBA8 to 10 expressing ATF1$_{Sc}^{opt}$ with N'-terminus fusion partner such as MBP, NusA, and TrxA achieved higher BA production than that of EcJWBA7 expressing ATF1$_{Sc}^{opt}$ alone, we could confirm that there is a synergistic effect between codon optimization and the use of a fusion partner in BA production with ATF1$_{Sc}$. Also, chaperone expression negatively affected the endogenous BB production. Similarly, improvement in the endogenous EB production occurred too. Referring to FIG. 17B, when the cell cultures were induced by 0 mg/ml, 0.1 mg/ml, 0.5 mg/ml and 5.0 mg/ml of L-arabinose, respectively, EcJWEB7 produced 263.9±51.8 mg/L, 337.6±46.1 mg/L, 365.7±69.2 mg/L, and 346.2±59.8 mg/L of EB, resulting in 1.3, 1.7, 1.8, and 1.7-fold improved EB production as compared to EcJWEB2 (200.4±9.4 mg/L. Referring to FIG. 17C, when the cultures were induced by 0 mg/ml, 0.1 mg/ml, 0.5 mg/ml and 5.0 mg/ml of L-arabinose, respectively, EcJWBB7 produced 25.6±10.7 mg/L, 30.0±4.8 mg/L, 51.4±3.4 mg/L, and 42.1±4.1 mg/L of BB, achieving 0.2, 0.2, 0.4, and 0.3-fold decreased BB production as compared to EcJWBB2 (127.4±32.5 mg/L). Overall, the AAT solubilization plays an important role for the de novo microbial biosynthesis of designer esters.

Working Example 10: Co-Solubilization of AdhE2$_{Ca}$ and AAT

Due to the low residual butanol in our BA/BB production experiments, we hypothesized that the low availability of butanol, one of the intermediates for butyl esters synthesis, might have affected the endogenous production of BB and EB. The bi-functional aldehyde/alcohol dehydrogenase AdhE2$_{Ca}$ is known for its critical role in butanol production, and its low solubility can significantly reduce in vivo activities as compared to the in vitro activities. We tested whether the co-solubilization of AdhE2$_{Ca}$ and AAT improved the de novo microbial biosynthesis of BA/BB by alleviating the limitation of butanol.

For BA production, we first constructed four pRSFDuet-1 plasmids carrying SM2 (adhE2$_{Ca}^{opt}$, malE_adhE2$_{Ca}^{opt}$, nusA_adhE2$_{Ca}^{opt}$, or trxA_adhE2$_{Ca}^{opt}$)-SM3 (fdh$^{opt}$)-SM4 (trxA_ATF1$_{Sc}^{opt}$), respectively (FIG. 12) and introduced them into the chassis cell TCS083 ΔfadE (DE3) with the pACYCDuet-1 plasmid carrying the SM1 (butyryl-CoA pathway) to generate EcJWBA11~EcJWBA14, respectively (FIG. 12). Next, we characterized these strains in conical tubes for BA production. The expression of the pathway enzymes was confirmed by SDS-PAGE analysis. Referring to FIG. 17A, the results show EcJWBA11 to EcJWBA14 produced 80.3±9.0 mg/L, 54.2±4.9 mg/L, 82.8±15.5 mg/L, and 203.0±5.7 mg/L of BA, respectively. Remarkably, EcJWBA14 achieved 2.3-fold improved BA production (203.0±5.7 mg/L) as compared to EcJWBA10 (89.5±14.8 mg/L), indicating that solubilization of pathway enzymes using a fusion partner can be a simple, but useful in metabolic engineering.

Nest, the use of TrxA fusion partner with AdhE2$_{Ca}^{opt}$ was investigated with respect to improved BB production. We constructed the pRSFDuet-1 plasmid carrying SM2 (trxA_adhE2$_{Ca}^{opt}$)-SM3 (fdh$^{opt}$)-SM4 (SAAT$_{Fa}$) and introduced it into the chassis cell TCS083 ΔfadE (DE3) with the pACYCDuet-1 plasmid carrying the SM1 (butyryl-CoA pathway) to generate EcJWBB8 (FIG. 12). By characterizing EcJWBB8 in conical tubes, the results show that EcJWBB8 achieved 1.3-fold improved BB production (167.3±18.2 mg/L) as compared to EcJWBB2 (127.4±32.5 mg/L) (FIG. 17C). Notably, EcJWBB8 achieved about 1.5-fold improved BB selectivity (50.6%) as compared to EcJWBB2 (34.0%), resulting in about 1.7-fold improved butanol/ethanol ratio (g/g of butanol to ethanol) (from 0.04 to 0.07) and about 0.6-fold reduced EB production (from 246.2±72.6 mg/L to 156.3±22.4 mg/L). This result suggests that there is a substrate competition between ethanol and butanol in the enzymatic reaction of ATF1$_{Sc}$, which can be alleviated by either engineering AATs with alcohol substrate preference or tuning the selective alcohol production. Overall, the results highlight the combinational solubilization of multiple pathway enzymes (such as, AdhE and AAT enzymes) is feasible to alleviate the enzyme expression of a large, complex metabolic pathway.

Working Example 11: Anaerobic Conditions

Although BA and BB production were improved via co-solubilization of AdhE2$_{Ca}$ and AAT, residual butanol titer was still lower than desired. Given that the abundant alcohol production is important for ester synthesis due to the high KM value of AATs, butanol production needs to be further improved for higher production of butyl esters. Because strict anaerobic conditions are important for alcohol production, we characterized the final strains, EcJWBA14, EcJWEB7, and EcJWBB8, in anaerobic bottles with pH adjustment to evaluate their performance in production of C4-dereived esters. The culture pH was adjusted to around 7 with 10 M NaOH every 24 hours to maintain the optimum growth pH of E. coli.

With reference to FIGS. 17A-17C, the characterization results of EcJWBA14, EcJWEB7, EcJWBB8 showed 12.9, 5.8, and 13.4-fold improvement in titers, 4.8, 3.7, and 4.6-fold improvement in yields, and 6.5, 1.4, and 3.4-fold improvement in productivity as compared to the initial strains, EcJWBA2, EcJWEB2, and EcJWBB2, respectively. Specifically, EcJWBA14 produced 441.4±40.9 mg/L of BA (9.2% of maximum theoretical yield) with 91.7% of selectivity, EcJWEB7 produced 408.9±44.3 mg/L of EB (8.5% of maximum theoretical yield) with 85.5% of selectivity, and EcJWBB8 produced 449.6±43.0 mg/L of BB (10.0% of maximum theoretical yield) with 53.5% of selectivity. In comparison with the direct fermentative production of butyryl-CoA-derived esters by E. coli in previous studies, EcJWBA14 achieved 882.8, 1839.0, and 3937.0-fold improved titer, productivity, and yield (TRY) in BA production, EcJWEB7 achieved 3.1, 3.1, and 11.0-fold improved TRY in EB production, and EcJWBB8 achieved 12.2, 12.2, and 44.1-fold improved TRY in BB production.

Working Example 12: Endogenous AdhE-Deficient Chassis

The modular cell TCS083 ΔfadE (DE3) is designed to be auxotrophic and required to metabolically couple with a butyryl-CoA-derived ester module. The promiscuity of endogenous alcohol dehydrogenases might interfere with the butyryl-CoA-derived ester modules, competing for ester biosynthesis because the endogenous bifunctional aldehyde/alcohol dehydrogenase adhE favors the formation of ethanol over butanol. To remove the endogenous adhE, TCS083 ΔfadE (DE3) was replaced with TCS095 (DE3), an adhE-deficient chassis cell, and generated EcJWBA15 (FIG. 12). With reference to FIG. 17A, the characterization results of EcJWBA15 in conical tubes showed that EcJWBA15 achieved higher BA production than EcJWBA14 by 1.28-fold with a titer of 259.5±11.6 mg/L and a selectivity of 94.8%. Still referring to FIG. 17A, in addition, by characterizing EcJWBA15 in anaerobic bottles with a pH of 7, 636.3±44.8 mg/L of BA (23.0% of maximum theoretical yield) with a high selectivity (95.7%) was produced.

TABLE 1

| Enzyme | Accession Number (UniProt) |
| --- | --- |
| AtoB$_{Ec}$ | P76461 |
| Hbd$_{Ca}$ | P52041 |
| Crt$_{Ca}$ | P52046 |
| Ter$_{Td}$ | Q73Q47 |
| AdhE2$_{Ca}$ | Q9ANR5 |
| Pdc$_{Zm}$ | P06672 |
| AdhB$_{Zm}$ | P0DJA2 |
| Fdh$_{Cb}^{opt}$ | O13437 |
| ATF1$_{Sc}$ | P40353 |
| SAAT$_{Fa}$ | Q9FVF1 |
| MBP | P0AEX9 |
| NusA | P0AFF6 |
| TrxA | P0AA25 |
| Tf | P0A850 |
| DnaK | P0A6Y8 |
| DnaJ | P08622 |
| GrpE | P09372 |
| GroES | P0A6F9 |
| GroEL | P0A6F5 |

As used herein, "amino acid" or "amino acid residue" or "residue" refers to any naturally occurring amino acid, any non-naturally occurring amino acid, any modified including derivatized amino acid, or any amino acid mimetic known in the art. The amino acid may be referred by both their common three-letter abbreviation and single letter abbreviation. In certain example embodiments, the modified proteins can be about 80%, 85%, 90%, 95%, 98% or more sequence identity to any one of SEQ ID NOS in copending U.S. application Ser. No. 17/453,305 or SEQ ID NOS: 1-97 herein. That is, the modified protein, although having an amino acid sequence at least partially or fully identical to those previously referenced, retains a mutated amino acid substitution. In certain example embodiments, the modified CAT protein is a functional fragment of any one of SEQ ID NOS: in the '305 copending application, the sequence of the fragment corresponding to one or more regions of the otherwise full-length amino acid sequences while retaining any of the particular modifications described herein. In certain example embodiments, the functional fragment including the Y20F substitution has 80%, 85%, 90%, 95%, 98% or more sequence identity to one or more regions of the full-length sequence set forth as any one of SEQ ID NOS: in the '305 copending application.

In certain example embodiments, one or more of the amino acids forming all or a part of the modified CAT proteins or functional fragments thereof can be stereoisomers. That is, any one or more of the amino acids of the modified CAT protein or functional fragments thereof can be a D- or L-amino acid. And in certain example embodiments, the modified CAT proteins or functional fragments thereof can also include one or more modified amino acids. The modified amino acid may be a derivatized amino acid or a modified and unusual amino acid. Examples of modified and unusual amino acids include but are not limited to, 2-Aminoadipic acid (Aad), 3-Aminoadipic acid (Baad), β-Aminopropionic acid (Bala, β-alanine), 2-Aminobutyric acid (Abu, piperidinic acid), 4-Aminobutyric acid (4Abu), 6-Aminocaproic acid (Acp), 2-Aminoheptanoic acid (Ahe), 2-Aminoisobutyric acid (Aib), 3-Aminoisobutyric acid (Baib), 2-Aminopimelic acid (Apm), 2,4-Diaminobutyric acid (Dbu), Desmosine (Des), 2,2'-Diaminopimelic acid (Dpm), 2,3-Diaminopropionic acid (Dpr), N-Ethylglycine (EtGly), N-Ethylasparagine (EtAsn), Hydroxylysine (Hyl), allo-Hydroxylysine (Ahyl), 3-Hydroxyproline (3Hyp), 4-Hydroxyproline (4Hyp), Isodesmosine (Ide), allo-Isoleucine (Alle), N-Methylglycine (MeGly, sarcosine), N-Methylisoleucine (MeIle), 6-N-Methyllysine (MeLys), N-Methylvaline (MeVal), Norvaline (Nva), Norleucine (Nle), and Ornithine (Orn). Other examples of modified and unusual amino acids are described generally in Synthetic Peptides: A User's Guide, Second Edition, April 2002, Edited Gregory A. Grant, Oxford University Press; Hruby V J, Al-obeidi F and Kazmierski W: *Biochem J* 268:249-262, 1990; and Toniolo C: *Int J Peptide Protein Res* 35:287-300, 1990; the teachings of all of which are expressly incorporated herein by reference. In certain example embodiments, the modified CAT protein or functional fragments thereof can be detectably labeled with a known label, such as a fluorescent or radioactive label.

In one aspect, the modified CATs can be CATaa Y20F, CATaa Y20F F97W, CATsa Y20F A138T, CATsa Y20F F97W A138T, CATec3 Y20F, or CATec3 F97W Y20F.

The feeding of any substance to a selected microorganism can include a mixture of sugars, a mixture of alcohols, a mixture of cellulosic materials, a mixture of carboxylic acids, and blends of any such mixtures to produce a plurality of esters. The mixtures, especially of the alcohols and/or carboxylic acids are preselected and have a preselected concentration for each alcohol or carboxylic acid to produce a preselected ester profile.

It should be noted that the embodiments are not limited in their application or use to the details of construction and arrangement of parts and steps illustrated in the drawings and description. Features of the illustrative embodiments and variants may be implemented or incorporated in other embodiments, variants, and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention. Having described the invention in detail and by reference to preferred embodiments thereof, it will be apparent that modifications and variations are possible without departing from the scope of the invention which is defined in the appended claims.

| | Primers | Primer sequence (5' to 3') |
|---|---|---|
| | | Primers for constructing the pATF1$_{Sc}$ by Gibson assembly |
| SEQ ID NO: 1 | ATF1$_{Sc}$_fwd | ATAATTTGTTTAACTTTAAGAAGGAGATATAGATATGAATGAAATGATGAGAAAAT |
| SEQ ID NO: 2 | ATF1$_{Sc}$_rev | TTTGTTAGCAGCCGGATCTCAGTGGTGGTGGTGGTGGTGGATAGGGCCTAAAAGGAGAG |
| SEQ ID NO: 3 | BB_ATF1$_{Sc}$_fwd | ATCCACCACCACCACC |
| SEQ ID NO: 4 | BB_ATF1$_{Sc}$_rev | ATCTATATCCTCCTTCTTAAAGTTAAACAAAATTATTTCTAG |
| | | Primers for constructing the pATF1$_{Sc}$ variants by site-directed mutagenesis using the QuickChange™ site-directed mutagenesis kit |
| SEQ ID NO: 5 | P348W_fwd | ATTTTTATCTGGGCAGATTGCCGCTCACAACTA |
| SEQ ID NO: 6 | P348W_rev | GGCAATCTGCCCAGATAAAAATATCCGTAAGCC |
| SEQ ID NO: 7 | P348R_fwd | ATTTTTATCCGTGCAGATTGCCGCTCACAACTA |
| SEQ ID NO: 8 | P348R_rev | GGCAATCTGCACGGATAAAAATATCCGTAAGCC |
| SEQ ID NO: 9 | P348M_fwd | ATTTTTATCATGGCAGATTGCCGCTCACAACTA |
| SEQ ID NO: 10 | P348M_rev | GGCAATCTGCCATGATAAAAATATCCGTAAGCC |
| SEQ ID NO: 11 | P348H_fwd | ATTTTTATCCATGCAGATTGCCGCTCACAACTA |
| SEQ ID NO: 12 | P348H_rev | GGCAATCTGCATGGATAAAAATATCCGTAAGCC |
| SEQ ID NO: 13 | P348K_fwd | ATTTTTATCAAGGCAGATTGCCGCTCACAACTA |
| SEQ ID NO: 14 | P348K_rev | GGCAATCTGCTTTGATAAAAATATCCGTAAGCC |
| SEQ ID NO: 15 | P348N_fwd | ATTTTTATCAATGCAGATTGCCGCTCACAACTA |
| SEQ ID NO: 16 | P348N_rev | GGCAATCTGCATTGATAAAAATATCCGTAAGCC |
| SEQ ID NO: 17 | P348I_fwd | ATTTTTATCATTGCAGATTGCCGCTCACAACTA |
| SEQ ID NO: 18 | P348I_rev | GGCAATCTGCAATGATAAAAATATCCGTAAGCC |
| SEQ ID NO: 19 | P348S_fwd | ATTTTTATCACAGCAGATTGCCGCTCACAACTA |
| SEQ ID NO: 20 | P348S_rev | GGCAATCTGCTGTGATAAAAATATCCGTAAGCC |
| SEQ ID NO: 21 | P348D_fwd | ATTTTTATCGATGCAGATTGCCGCTCACAACTA |
| SEQ ID NO: 22 | P348D_rev | GGCAATCTGCATCGATAAAAATATCCGTAAGCC |
| SEQ ID NO: 23 | P348C_fwd | ATTTTTATCTGCGCAGATTGCCGCTCACAACTA |
| SEQ ID NO: 24 | P348C_rev | GGCAATCTGCGCAGATAAAAATATCCGTAAGCC |
| SEQ ID NO: 25 | P348A_fwd | ATTTTTATCGCTGCAGATTGCCGCTCACAACTA |
| SEQ ID NO: 26 | P348A_rev | GGCAATCTGCAGCGATAAAAATATCCGTAAGCC |
| SEQ ID NO: 27 | P348Q_fwd | ATTTTTATCCAGGCAGATTGCCGCTCACAACTA |
| SEQ ID NO: 28 | P348Q_rev | GGCAATCTGCCTGGATAAAAATATCCGTAAGCC |

| | GENE | SEQUENCE |
|---|---|---|
| SEQ ID NO: 29 | SAAT$_{Fa}$ | ATGGAAAAAATCGAAGTCTCAATTAACTCCAAGCATACCATCAAACCCTCTACCTCTAGTAGCCCGCTACAACCCTATAA
ACTGACCTTACTGGATCAGCTGACGCTGGCGGACTTACTTCAAGCTCTGTCGGACTCTGTTTTTTACCGATCACCGATCACGATTTTA
ATCTGCCCAGACGCTGGCGACTTACTTCAAGCTCTGTCGGAGACTCTGTCCGATCTCACGCTGTATTATCCCTGAGCGGACGTGT
TAAAAACAATTTGTATATTGAAATTGAGTGCCGCAAAATTGTACCGAAGCGCGTGTGCGTATTAGAGGCCGTGTAAATTGCGATATGACCGA
TTTTCTGCGTCTGCGAGACTAAAATTGAGTGCCGCAAAATTGTACCCGATTAAACCTTTCAGTATGGAAGCAATTAGCGAT
GAACGTTACCCGTTGCTGGGCGTCCAGATTGTTTCCTTAAATCTTGGGCGCATGACTGCCGATCGGAGTGTCAGTCATAAAT
TGATAGATGGTGCACGGCAGATTGTGCGCTTCGTGCTTGATGCACGCAGATGAAGAAAATACGTTGACCAATTGGAGGC
CCTGTGTTTGCGGGGAAAAAGTGCCCAAAACCGTCTCGCTTGCCGTTCATGCCGCTGACAGGCTTCTTATGGAAGCACCTGATGCTGC
AGCAAAATCGAGGACGTCCATTGACAAGTGGGACTACAATCGCACCCGTCTGTCAATTACGCGGTAACCTGTCTGGTGGGCCGAAGCAGTAACCTGCTATCCGCAT
GAACATGGAAAACCGTTTAGATAACGGACTGTAACTGTGATCTGGTTAACTGCTGAACGGATCCGTCAAGCAGTGTGAACGGCAATGGCAACATGCAATGGCGAC
CACCCCGGAGATTTCTGACCTTAAATCGTGATCTGTAACTGCTGAACGGATCCGTCAAGCAGTGTGAACGGCAATGGCAATGGCGAC |

-continued

```
TATTTCGAGACCTTTAAAGGTAAAGAAGGCTATGCCGGATGTGCAATACTTGGATTTCCAGCGAACAATGTCGTCC
ATGGAACCGGCTCCGGACATTTATCTGTTTCATCCTGGACTAACTTTTTTAACCCGTTGGATTTCCGCTGGGCGCAC
CTCCTGGATTGGAGTTGCAGTTAAATTGAGAGTGCGTCCTGCCAAATTTATATATCTGTGCCCACACAGTGCGGTTCG
GGTATCGAGGCCTTGGGTCAACTTGGAGGAAGAAAAAATGGCCATGCTCGACAGGATCGCATTTCGCATTTTCTAGCGCTGGC
GTCACCTAAAACCCTGATC
```

SEQ ID NO: 30 ATF1$_{Sc}$$^{opt}$

```
ATGAACGAAATCGACGAAATCAGGCGCCAGTTCAGCAGGAGTGTCTGAAAGAAATGATTCAAAATGGTCATGCGCG
TAGAATGGGTTCAGTGGAGGATTTGTACTGTGCGCTGGCCGTTGCGCTGGAGGCTTGACGCTGATCAGTTGACGCTGTACCGTGCCGAAAC
GTCAGATTACTACCTCGTGATCAGTTGCCTGGCGCTGTACGGGTACGTAATCTGTTAAAAAACCGACTCTTCTGCACGACTAC
TTACCGACGCGTTGGCCGAACCAGAACATCCTATTATAGAAGCAGTGAATATTACAGCCGTCCACCCGTGCACGACTAC
ATATCGGTCTTACAGGAATTAAAGCTGTGCGGGCTATACGGCAGCTGATTTGTTTGCCGAAGCAGCTCAGCCGGTTATGAAGACAGATT
CTGAAGAATTCAAAAAGATCAAAATAGCACCGGCCCATCTGGCCGCTTGTTCCATTCATTCTTTAAACTACCACCCTGACAATCCATATTCG
GCCCCACAGGCCCATCTGGCGCTGTCTCCATTCATTCTTTGCCGAAGAGCACTGAGAACTCATATTTGTGAGCA
ATCATTGCATGTCAGATGGCCCTATCTTTGCCGATCGTGACGAACTGCCGAGCCGATCGAAAAGTGATT
AAGAAGCTAGATTACATnCAAATACGAAGAAGACTACCAGCTGCTGCTAAACTGCCGAGCCGATCGAAAAAGTGATT
GATTTCGTCCGCGTATCTTTTTATTCCAAAGACAGAACGAACACACCACCAGGAAAACTACCTTTCATGGCCATCAAAAGG
GTATGTATGCCATGATGATGCGGAAAAGACCGACGACGTCGTACCGAAATCATTAATATTAGCCGACTGAATTTCAA
GCATAAAAGCAAACATCAAATCGAACATCCAGGGCAACAATGTACCATTACTCCTTTCTCCATGTTTGTTGGACTGCCGTCTCAG
TTGCCTGATGACGAGCAAATAGCGGACGAAATGCGCTGTGCGAATGTGGCAGTCTGGCTTCATTGACTTCACTCCGGATCGC
GAATTTGACATGAATGAATAACAAGAAAATTTTTGGCCACTGACCATTCAGCAATGnGGTCTGTTCAATCAACTTGAAGAACTCATGTGT
GACCGGGCTAHGGTAAACGTCGTGGCGTAGCTTTGTGGCCAATTCCGTCGCGTCGACAAAAAACGTCGTAGTTCGACAGGAGTCCCTGGAAGAGCTTTGTAGCA
AAATATTCTATTTGCGACTTAGCTTTCGTGCCAATCGATCTTGCGATTACGCAAAAAGCTGTTCAATCAACTTGAAGAACTCAT
ATGTTAAAGGTATGAATATCGTCGACCTAAACCTGTGGGTCCG
TATATAAGCTTTTGTTACTACTGGTCCCG
```

SEQ ID NO: 31 SAAT$_{Fa}$$^{opt}$

```
ATGGAAAAATCTCAATTAACTCAAGCATACCATCAAGCCCTATGTCCCAGCTCTGTGACGCCACACGAGGTCTACACCAACCTGTGTTTTTACCGATCACGATCGATTTTAATCTGC
GACCTTACTGGATCAGCTGAGCGTACGGCCACGTCAAGCTCCTGTCGGAGACTCTCACGCTGTATTATCCCGTGTCTCACCGCGACGTGTTAAAAACA
CGCAGAGCCTGGAGCTGGAGCTACGTCAAGCTCTGTGACGCCACTGAGGTCTCACCGCGACGTGTTAAAAACA
ATTTGTATATTGATGATCTGTGAAACGCGAGAGGAAGGCGTGCAATCCGATCGATCCCGATCTATCCCGAGCGGACGTGTTAAAAACA
GCCCAAAATTGAGTGCCTGAACGAATTGCGTCATCAGCTTAAAGCCAAGCTCCTGACCACCATTAGCGTATGAACGTACCCCGTT
GCTGGGCGTCCAGTTAGTGTTTGATTCGGGCGCATCCGATCGTGTTTCGTGCCGATCCGAGTCAGTCAGTTCATAAATTGATAGATGGTGCAGAC
GGCAGATTGCTTGTCCACCGCACTGACCTTGCCAGGAGAATACTGTGACCAAATGAGGCCCCGGTGGTTTGCCCGGGAAAA
AGTCGCCACCCGCCGTCTGTTTCGCGTGAAGATTCAAGAAGACAACGGAAGGCAAAATCAGGAGCGCGTCCCAAA
ACCGTCTCCGCGTTCATGCGCGTGACAGGCGATCATCGCGCGCAGCGAAGCGGCAGCTGCTCCGCGCAAGTGGGAAGCGTCCCAAA
ATCGACCCGTCTGTTCTGGTGCGCCAGGCGATCCGTCAAGCAGTCGATCGCCATAACCACCCGGAGATTTCTGACCTTAAACTGTTGA
TCTGGTTAACTTGCTGGCATCCGAGATGCGTCCAGCGACATCATCCGATCGTAGTCGATTCGCATAACCACGCCTTAAACTGTTGA
CGAGATGTGTAATACTTGGATTTTCGCAAACATCATCGATTTCTGAATCTGAGTCGTGAAATGTTGCTGCAGTATACGCGCGGCGTCCGT
ACTAACTTTTTATAATCGTCGTGCCACAGTGCGGTTCCGGATTTCGGTGTCAACTTGGTCACACTTGGAGGAAGAAAATTGAGAGTGCGTCCT
GCAAATTTATATAATCGTGCCACAGGATCCCCATTTCTAGCGCTGCTGCGTCACCTAAAACCCTGATC
ATGCTGAACAGGATCCCCATTTCTAGCGCTGCTGCGTCACCTAAAACCCTGATC
```

SEQ ID NO: 32 adhE2$_{Ca}$$^{opt}$

```
ATGAAAGTGACCAATCAAAAAGAGCTGAAACAAGAACTGAACGAACTTCGTGAAGCGCAAAAAAATTCGCAACCTACAC
GCAGGAGCAGGTGGATAAATTTTCAAGCAGTGCGATTGCGGCGCAGAAGACGCGATTAACCTGGCGAAGCTGGCG
GTGGAAGAACCCGGATTGGGTCGTATTATTGATGGAAGGACACAAGATCATCAAGAACCATTTTGCCGCGGAATACATTATAACAAGTA
CAAAAACGAAAAGACGTGTGGTTATTATGACCAATCCACGTCAACGGCGCATCGCAAGGTGGCAGAACCGATCGTATCG
TCGCTGCGATCGTTCCGACGACAATTGCAGTTGGAAAAAGTTTAAAAGTTTGATTAGCCCTGAAAACTCGTAACGCCAT
CTTCTTTTTCCCCGAAGACATCATTGGCGCTGGATGATCGGCGACCATTGCGCCCGGCGTGCCGTGAAGGCGGGA
GGCCCCGAAGAACATCATTGGCGTGACGATCGGCAATTGAGCTCAGCCAAGACCTCAGCCAAGGCGGATATA
TTCTGGCGACAGGCGGTGTCCGAGCATGGTGTAAAGCGCCTACTTGTCTGTCTGGCGAAACCAGCCATTGTTGTTGGAGCCGGCAAC
```

-continued

ACTCCGGCAATTATTGATGAGAGCGCCGATATCGATATGGCGGTTAGTAGCATCATCCTGTCTAAAACCTACGACAATGGT
GTGATCTGCCGAGCGAACAAAGTATTCTCGTCATGAACTCTATCTATGAAAAGGTGAAAGAGAGTTTGTGAAGCGTGG
TAGCTATATCCTGAACCAGAACAAACAAATGTCCAAATGAACAATGTTAAGAATGAGCTATCAATGCCGATATCGT
TGGTAAAGTGCCTATATTCGGAGTTGTTTCCACGAAAAATCGTCGCCGTATTAGCAATGTATAAAGATTTTAATTGGTGAGGTTCA
GAGCGTGAAAAATCGGAGTTGTTTTCCACGAAAAATCGTCGCCGTATTAGCAATGTATAAAGATTTTAATTGGTGAGGTTCA
AGCCCTGAAAAAGGCCAGCGCTTAATTGAATTAGGCGGCTCTGGTCATACCTGTCATGCTGTACATCGATAGCCAGAACAA
TAAAGATAAAGTTAAAGAATTTGGCCTGCACGTTTATCAATATGCCTTCAAGCCAGGGCGCCTC
GGGTGATCTTTATAATTTTGCAATCGCGCCGAGCTTCACTCTGGGTTGTGGGACGTGGGTGCCAATAGCGTCTCACAGAA
TGTCGAACCGAAGCATAACTGAACATCAACAGTCGCCACTGAAGGAACTGTGAAACATGCTGGHCAAAGTGCCGCAAA
AATCTATTTCAAGTATGGTTGCCTGCAATCAGTCCGCACTGAAGGAACTGAAACATGAACAAAACGTGCGTTTATTGTTACC
GATAAGGACCCTGTTTAAACTGGGCTATGTGGACAAAATTACTAAGTTCTGATGAAATTGATATTAATACTCGATCTTCA
CCGATATATTAAAGTGACCCTACGATGATGCGGCCAAAGTTATGCATCTGTTGTATGAGTATCCGAAGCCGAGATTGAGA
TCAGTATTGGGGTGGTTCTCCGATGATGCGGCCAAAGTTATGCATCTGTTGTATGAGTATCCGAAGCCGAGATTGAGA
ACTGGCTATCAATTTATGGACATCCGAAAGCGGATCTGCAACTTCCCAAAGirAGGTACGAAAGCCATTAGCGTAGCCAT
TCCTACCACCCGGGTTACCGGAGTAGCATGCAATTATCGATACGGAACATGATCGAATGCACAATGATGAGAACGTCGTAAACTTACAGCGGC
GACCAGCTATGAATTTAACACCAAACATGCCAATTATCGATACGGAACATGATGCAAACCTAATGCCAATTATACCGATGAGCTGGCCT
GACTGGGATTGATGCCCTTGGTTCACGCGATTGAAGCATACGTGAGTGTGATGCCCAACCAATGATATCGAAGCTCGAGAAAAAAT
GCGCGTATCAAATGATCTTCAAATATCTGCCGGTGCCTACAAAAACGGCACCAATGATATCGAAGCTCGAGAAAAAAT
GGGCGATCCCTCAAACATCGCAGGGATGCATTCGCCGACGCATTCTGGGCGTGTGCCACTCTATGCCACACAAACTGG
GTGCGATGCCACCATGTGCACACGCATTGCCAATACAAAAGCCCGAATGCTAAGCTATCTCTAAGTTAAATGTCCGACCGACTGCC
CAACCAAACAAACCGCGTTTCCCGATACCGAGAAAGTGACCGCCTGATTGAAGCTATCTCTAAGTTAAATGTCCGACCGACTGCC
TGAAAGGCACCTCTGATACCGAGAAAGTGACCGCCTGATTGAAGCTATCTCTAAGTTAAATGTCCGAATCTCTGAATC
AGAACATCTCGGCAGCTCGGGATCAATACCACTATCCGTGATCTCCGAACTCAAAGACATTTACATAAAGAGTTTC
AATGCACAACCGCCAACCCAACCTATCCGTGATCTCCGAACTCAAAGACATTTACATAAAGAGTTTC

SEQ ID NO: 33 fdh_Cb^opt

ATGAAAATTGTCTGGTTTTGTATGATGCGGAAAGCATGCGGCGACGAAGCATGAACAGGTCATGAACTTATTACCGAGCGATAAGAAGGCAAACC
ACAAACTGGGCATTGCTAACTGCTGAAAGCATGCGGCGACGAACTTATTACCGAGCGATAAGAAGGCAAACC
TCCGAATTAGACAGATATTCCGGATGCGACATTATTATCCGTTTCACCCGGCATACATTACCAAAGAAC
GTTTAGATAAAGCTAAAAACTGAAAACCTCCGTGTTAGAGGTAACAGGTAGCAACGTCGTCTCAGTGCGGAACACGTGGTAAT
ACCAGACGGACAAAAAAATCTCCGTGTTAGAGGTAACAGGTAGCAACGTCGTCTCAGTGCGGAACACGTGGTAAT
GACCATGCTAGTTTTGGTCCGTAACTTTGTTCCGGCACATGAACAACCAATTATCAATCATGACTGGGAGGTCGCGGCTAT
CGCGAAGATGCCTACGATATTGAGGGCAAAACCATTGCGACTATTGAGGACGCTTACCAAGGACCGCTGAACCAAAAGAGGCTGAAGAAAA
AACGCCTTTCTTCCGTTTAACCCGAAGATATTGAGGAATATTGAAGGAACTCGTTGCACAGGCAGATATTGTTACCGTGAATGCGCCCCTGCA
CGGGGGAATTGCGATTTGCGTGTCGATTTGCGTCGACTTAACAAAGAACTACTGAGTAAATTAAAAGGCGCCCTGGCTCGTGAATACAGCTC
GTGGTGCGATTTGCGATTTGAAGATGTGCCGCAGCACTGGACTGAGAGGCGTGGATATGCCTGATGATCATCCTAAAGATCATCCTGGCGAGGGCAATGCCTACGA
GTGGTGCGATTTGCGATTTGAAGATGTGCCGCAGCACTGGACTGAGAGGCGTGGATATGCCTGATGATCATCCTAAAGATCATCCTGGCGAGGGCAATGCCTACGA
GTGGTCCCACGGACCACCTAAAGATCATCCTGGCGACCCTTGACGCCACAACCTTGACGCCACAAACTCGCTACGCGGAAGGTACTAAGAACATTCTGGAGTCGTTT
CCCCATTACCTCCGGCACCAACCTTGACGCCACAAACTCGCTACGCGGAAGGTACTAAGAACATTCTGGAGTCGTTT
TTACGGGCAAGTTTGATTACCGGACCCGGAGGATATAATTCTTCTGAACGGTGAATAACGTGACCAAGGCTATGGTAAAC
ACGATAAAAAAA

The copy number of duet vectors are as follows: pACYCDuet-1, ~10; ~40; pRSFDuet-1, 100[4].

| Plasmid | Primers (5'→3') | Cloning strategies |
|---|---|---|
| Submodule1 (SM1): Butyryl-CoA synthesis | | |
| pACYCDuet-1 $P_{T7lac}$::atoB$_{Ec}$::hbd$_{Ca}$::crt$_{Ca}$-P$_{T7lac}$::ter$_{Td}$ pETDuet-1 $P_{T7lac}$::atoB$_{Ec}$::hbd$_{Ca}$::crt$_{Ca}$-P$_{T7lac}$::ter$_{Td}$ pRSFDuet-1 $P_{T7lac}$::atoB$_{Ec}$::hbd$_{Ca}$::crt$_{Ca}$-P$_{T7lac}$::ter$_{Td}$ | CrCoA_F: CAGCAGCCATCACCATCATCACCACAGC CAGGATCCGATGAAAAATTGTGTCATCG TCAG (SEQ ID NO: 34) CrCoA_R: CTATCTATTTTTGAAGCCTTCAATTT (SEQ ID NO: 35) MCS1_MCS2 linker_F: GCTTTCATAGAGAAAAGAAAAATTGAAG GCTTCAAAAATAGATAGGAATTCGAGCT CGGC (SEQ ID NO: 36) MCS1_MCS2 linker_R: ATTGTTCCTAACCATTGGTTTTACAATC ATCATATGTATATCTCCTTCTTATACTT AACT (SEQ ID NO: 37) ter$_{Td}$_F: AGTTAAGTATAAGAAGGAGATATACATA TGATGATTGTAAAACCAATGGTTAGG (SEQ ID NO: 38) ter$_{Td}$_R: TCAAATTTCGCAGCAGCGGTTTCTTTAC CAGACTCGAGTTAAATCCTGTCGAACCT TTCT (SEQ ID NO: 39) BB_Duet_F: CGGATCCTGGCTGTGG (SEQ ID NO: 40) BB_Duet_R: CTCGAGTCTGGTAAAGAAACC (SEQ ID NO: 41) | Biosynthesis pathway of Butyryl-CoA in pDL2[5] was subcloned into the plasmids with various copy numbers by Gibson Assembly method[6]. Specifically, atoB$_{Ec}$-hbd$_{Ca}$-crt$_{Ca}$ and Ter$_{Td}$ were subcloned into the MCS1 and MCS2 of the duet vectors, respectively. |
| Submodule2/3/4 (SM2-SM3-SM4) for BA synthesis: Butanol + NADH + ATF1 | | |
| pACYCDuet-1 $P_{T7lac}$::adhE2$_{Ca}$::fdh$_{Cb}^{opt}$-$P_{T7lac}$::ATF1$_{Sc}$ pETDuet-1 $P_{T7lac}$::adhE2$_{Ca}$::fdh$_{Cb}^{opt}$-$P_{T7lac}$::ATF1$_{Sc}$ pRSFDuet-1 $P_{T7lac}$::adhE2$_{Ca}$::fdh$_{Cb}^{opt}$-$P_{T7lac}$::ATF1$_{Sc}$ | adhE2$_{Ca}$_F: GCCATCACCATCATCACCACAGCCAGGA TCCGATGAAAGTTACAAATCAAAAAGAA CTAA (SEQ ID NO: 42) adhE2$_{Ca}$_R: TATATCTCCTTTTAAAATGATTTTATAT AGATATCCTTAAGTTCAC (SEQ ID NO: 43) fdh$_{Cb}^{opt}$_F: AGGATATCTATATAAAATCATTTTAAAA GGAGATATAATGAAAATTGTGCTGGTTT TGTA (SEQ ID NO: 44) fdh$_{Cb}^{opt}$_R: TTGTCGACCTGCAGGCGCGCCGAGCTCG AATTCTTATTTTTTATCGTGTTTACCAT ACGC (SEQ ID NO: 45) MCS1_MCS2 linker_BA_F: TAAGAATTCGAGCTCGGC (SEQ ID NO: 46) MCS1_MCS2 linker_BA_R: GATTTCATTCATCATATGTATATCTCCT TCTTATACTTAACT (SEQ ID NO: 47) ATF1$_{Sc}$_F: ATATTAGTTAAGTATAAGAAGGAGATAT ACATATGATGAATGAAATCGATGAGAAA AATC (SEQ ID NO: 48) ATF1$_{Sc}$_R: CGTTCAAATTTCGCAGCAGCGGTTTCTT TACCAGACTCGAGCTAAGGGCCTAAAAG GAGA (SEQ ID NO: 49) BB_Duet_F: CGGATCCTGGCTGTGG (SEQ ID NO: 40) BB_Duet_R: CTCGAGTCTGGTAAAGAAACC (SEQ ID NO: 41) | Five PCR fragments including i) adhE2$_{Ca}$ from gDNA of C. acetobutylicum, ii) fdh$_{Cb}^{opt}$ from pET29 $P_{T7lac}$::fdh$_{Cb}^{opt}$, iii) MCS1_MCS2 linker from pACYCDuet-1, iv) ATF1$_{Sc}$ from, and v) plasmid backbone with various copy numbers were assembled by Gibson Assembly method[6]. Specifically, adhE2ca-fdhcb and ATF1$_{SC}$ were subcloned into the MCS1 and MCS2 of the duet vectors, respectively. |

The copy number of duet vectors are as follows: pACYCDuet-1, ~10; ~40; pRSFDuet-1, 100[4].

| Plasmid | Primers (5'→3') | Cloning strategies |
|---|---|---|
| pRSFDuet-1 $P_{T7lac}$::adhE2$_{Ca}$::fdh$_{Cb}$$^{opt}$- $P_{T7lac}$::ATF1$_{Sc}$$^{opt}$ | ATF1$_{Sc}$$^{opt}$_F: ATGAACGAAATCGACGAAAAAAATCAG (SEQ ID NO: 50) ATF1$_{Sc}$$^{opt}$_R: CGGACCCAGTAACAAAGCTTTATA (SEQ ID NO: 51) BB_BA_ATF1$_{Sc}$$^{opt}$_F: GAGCTTTGTAGCATATATAAAGCTTTGT TACTGGGTCCGCTCGAGTCTGGTAAAGA AAC (SEQ ID NO: 52) BB_BA_ATF1$_{Sc}$$^{opt}$_R: GCGCCTGATTTTTTTCGTCGATTTCGTT CATCATATGTATATCTCCTTCTTATACT TAAC (SEQ ID NO: 53) | ATF1$_{Sc}$ in pRSFDuet-1 $P_{T7}$::tadhE2$_{Ca}$::fdh$_{Cb}$$^{opt}$- $P_{T7}$::ATF1$_{Sc}$ was replaced with ATF1$_{Sc}$$^{opt}$ from pET29 $P_{T7}$::ATF1$_{Sc}$$^{opt}$ by Gibson Assembly method[6]. |
| pRSFDuet-1 $P_{T7lac}$::adhE2$_{Ca}$::fdh$_{Cb}$$^{opt}$- $P_{T7lac}$::malE_ATF1$_{Sc}$$^{opt}$ | malE_ATF1$_{Sc}$$^{opt}$_F: ATATTAGTTAAGTATAAGAAGGAGATAT ACATATGATGAAAATCGAAGAAGGTAAA CTGG (SEQ ID NO: 54) malE_ATF1$_{Sc}$$^{opt}$_R: CCTGCTGAACTGGCGCCTGATTTTTTTC GTCGATTTCGTTCTTGGTGATACGAGTC TGC (SEQ ID NO: 55) BB_BA_FP_ATF1$_{Sc}$$^{opt}$_F: AACGAAATCGACGAAAAAAATCAG (SEQ ID NO: 56) BB_BA_FP_ATF1$_{Sc}$$^{opt}$_R: CATATGTATATCTCCTTCTTATACTTAA CTAATATACT (SEQ ID NO: 57) | The start codon of ATF1$_{Sc}$$^{opt}$ in pRSFDuet-1 $P_{T7}$::tadhE2$_{Ca}$::fdh$_{Cb}$$^{opt}$- $P_{T7}$::ATF1$_{Sc}$$^{opt}$ was replaced with the malE from gDNA of E. coli MG1655 by Gibson Assembly method[6]. |
| pRSFDuet-1 $P_{T7lac}$::adhE2$_{Ca}$::fdh$_{Cb}$$^{opt}$- $P_{T7lac}$::nusA_ATF1$_{Sc}$$^{opt}$ | nusA_ATF1$_{Sc}$$^{opt}$_F: ATATTAGTTAAGTATAAGAAGGAGATAT ACATATGATGAACAAAGAAATTTGGCT GTAG (SEQ ID NO: 58) nusA_ATF1$_{Sc}$$^{op}$_R: CACTCCTGCTGAACTGGCGCCTGATTTT TTTCGTCGATTTCGTTCGCTTCGTCACC GAAC (SEQ ID NO: 59) BB_BA_FP_ATF1$_{Sc}$$^{op}$_F: AACGAAATCGACGAAAAAAATCAG (SEQ ID NO: 56) BB_BA_FP_ATF1$_{Sc}$$^{op}$_R: CATATGTATATCTCCTTCTTATACTTAA CTAATATACT (SEQ ID NO: 57) | The start codon of ATF1$_{Sc}$$^{op}$ in pRSFDuet-1 $P_{T7}$::adhE2$_{Ca}$::fdh$_{Cb}$$^{opt}$- $P_{T7}$::ATF1$_{Sc}$$^{opt}$ was replaced with the nusA from gDNA of E. coli MG1655 by Gibson Assembly |
| pRSFDuet-1 $P_{T7lac}$::adhE2$_{Ca}$::fdh$_{Cb}$$^{opt}$- $P_{T7lac}$::trxA_ATF1$_{Sc}$$^{opt}$ | trxA_ATF1$_{Sc}$$^{opt}$_F: TATTAGTTAAGTATAAGAAGGAGATATA CATATGATGAGCGATAAAATTATTCACC TGAC (SEQ ID NO: 60) trxA_ATF1$_{Sc}$$^{opt}$_R: CTGCTGAACTGGCGCCTGATTTTTTTCG TCGATTTCGTTCGCCAGGTTAGCGTC (SEQ ID NO: 61) BB_BA_ FP_ATF1$_{Sc}$$^{opt}$_F: AACGAAATCGACGAAAAAAATCAG (SEQ ID NO: 56) BB_BA_FP_ATF1$_{Sc}$$^{opt}$_R: CATATGTATATCTCCTTCTTATACTTAA CTAATATACT (SEQ ID NO: 57) | The start codon of ATF1$_{Sc}$$^{opt}$ in pRSFDuet-1 $P_{T7}$::adhE2$_{Ca}$::fdh$_{Cb}$$^{opt}$- $P_{T7}$::trxA_ATF1$_{Sc}$ was replaced with the trxA from gDNA of E. coli MG1655 by Gibson Assembly method[6]. |
| pRSFDuet-1 $P_{T7lac}$::adhE2$_{Ca}$::fdh$_{Cb}$$^{opt}$- $P_{T7lac}$::trxA_ATF1$_{Sc}$$^{opt}$ | adhE2$_{Ca}$$^{opt}$_F: ATGAAAGTGACCAATCAAAAAGAGC (SEQ ID NO: 62) adhE2$_{Ca}$$^{opt}$_R: TTAGAAACTCTTTATGTAAATGTCTTTG AGTTCG (SEQ ID NO: 63) BB_BA_adhE2$_{Ca}$$^{opt}$_F: CAAAGACATTTACATAAAGAGTTTCTAA AAGGAGATATAATGAAATTGTGCTGGT TTTG (SEQ ID NO: 64) BB_BA_adhE2$_{Ca}$$^{opt}$_R: GTTCAGTTTCTGTTTCAGCTCTTTTTGA TTGGTCACTTTCATCGGATCCTGGCTGT GG (SEQ ID NO: 65) | adhE2$_{Ca}$ in pRSFDuet-1 Prz:tadhE2ca::fdh$_{Cb}$$^{opt}$- $P_{T7}$::trxA_ATF1$_{Sc}$ was replaced with adhE2$_{Ca}$$^{opt}$ from pET29 $P_{T7}$::adhE2$_{Ca}$$^{opt}$ by Gibson Assembly method[6]. |

The copy number of duet vectors are as follows: pACYCDuet-1, ~10; ~40; pRSFDuet-1, 100[4].

| Plasmid | Primers (5'→3') | Cloning strategies |
|---|---|---|
| pRSFDuet-1 $P_{T7lac}$::malE_adhE2$_{Ca}^{opt}$::fdh$_{cb}^{opt}$- $P_{T7lac}$::trxA_ATF1$_{Sc}^{opt}$ | malE_adhE2$_{Ca}^{opt}$_F: GCAGCCATCACCATCATCACCACAGCCA GGATCCGATGAAAATCGAAGAAGGTAAA CTGG (SEQ ID NO: 66) malE_adhE2$_{Ca}^{opt}$_R: CGTTCAGTTTCTGTTTCAGCTCTTTTTG ATTGGTCACTTTCTTGGTGATACGAGTC TGC (SEQ ID NO: 67) BB_BA_FP_adhE2$_{Ca}^{opt}$_F: CGGATCCTGGCTGTGG (SEQ ID NO: 40) BB_BA_FP_adhE2$_{Ca}^{opt}$_R: AAAGTGACCAATCAAAAAGAGCTG (SEQ ID NO: 68) | The start codon of adhE2$_{Ca}^{opt}$ in pRSFDuet-1 $P_{T7lac}$::adhE2$_{Ca}^{opt}$::fdhC b$^{opt}$. $P_{T7iac}$::trxA_ATF1sc$^{opt}$ was replaced with the malE from gDNA off. co//MG1655 by Gibson Assembly method[6]. |
| pRSFDuet-1 $P_{T7lac}$::nusA_adhE2$_{Ca}^{opt}$::fdh$_{cb}^{opt}$- $P_{T7lac}$::trxA_ATF1$_{Sc}^{opt}$ | nusA_adhE2$_{Ca}^{opt}$_F: GCAGCCATCACCATCATCACCACAGCCA GGATCCGATGAACAAAGAAATTTTGGCT GTAG (SEQ ID NO: 69) nusA_adhE2$_{Ca}^{opt}$_R: CGTTCAGTTTCTGTTTCAGCTCTTTTTG ATTGGTCACTTTCGCTTCGTCACCGAAC (SEQ ID NO: 70) BB_BA_FP_adhE2$_{Ca}^{opt}$_F: CGGATCCTGGCTGTGG (SEQ ID NO: 40) BB_BA_FP_adhE2$_{Ca}^{opt}$_R: AAAGTGACCAATCAAAAAGAGCTG (SEQ ID NO: 68) | The start codon of adhE2$_{Ca}^{opt}$ in pRSFDuet-1 $P_{T7lac}$::adhE2ca$^{opt}$::fdhc b$^{opt}$. $P_{T7iac}$::trxA_ATF1sc$^{opt}$ was replaced with the nusA from gDNA off. co//MG1655 by Gibson Assembly method[6]. |
| pRSFDuet-1 R$_{T7lac}$::trxA_adhE2$_{Ca}^{opt}$::fdh$_{cb}^{opt}$- $P_{T7lac}$::trxA_ATF1$_{Sc}^{opt}$ | trxA_adhE2$_{Ca}^{opt}$_F: CAGCCATCACCATCATCACCACAGCAG GATCCGATGAGCGATAAAATTATTCACC TGAC (SEQ ID NO: 71) trxA_adhE2$_{Ca}^{opt}$_R: CGTTCAGTTTCTGTTTCAGCTCTTTTTG ATTGGTCACTTTCGCCAGGTTAGCGTC (SEQ ID NO: 72) BB_BA_FP_adhE2$_{Ca}^{opt}$_F: CGGATCCTGGCTGTGG (SEQ ID NO: 40) BB_BA_FP_adhE2$_{Ca}^{opt}$_R: AAAGTGACCAATCAAAAAGAGCTG (SEQ ID NO: 68) | The start codon of adhE2$_{Ca}^{opt}$ in pRSFDuet-1 $P_{T7lac}$::adhE2ca$^{opt}$::fdhc b$^{opt}$. $P_{T7iac}$::trxA_ATF1sc$^{opt}$ was replaced with the trxA from gDNA off. co//MG1655 by Gibson Assembly method[6]. |

Submodule2/3/4 (SM2-SM3-SM4) for EB synthesis: Ethanol + NADH + SAAT

| Plasmid | Primers (5'→3') | Cloning strategies |
|---|---|---|
| pACYCDuet-1 $P_{T7lac}$::pdc$_{Zm}$::adhB$_{Zm}$::fdh$_{Cb}^{opt}$-$P_{T7lac}$::SAAT$_{Fa}$ | EtOH_F: GGCAGCAGCCATCACCATCATCACCACAG CCAGGATCCGATGAGTTATACTGTCGGTA CC (SEQ ID NO: 73) EtOH_R: CGCATCATACAAAACCAGCACAATTTTCA TTATATCTCCTTTTAGAAAGCGCTCAGGA AG (SEQ ID NO: 74) fdh$_{Cb}^{opt}$_F: ATGAAAATTGTGCTGGTTTTGTAATGAAA ATTGTGCTGGTTTTGTA (SEQ ID NO: 75) fdh$_{Cb}^{opt}$_R: TTGTCGACCTGCAGGCGCGCCGAGCTCGA ATTCTTATTTTTTATCGTGTTTACCATAC GC (SEQ ID NO: 45) MCS1_MCS2 linker_F: AAAATAAGAATTCGAGCTCGGC (SEQ ID NO: 98) MCS1_MCS2 linker_R: GGAATTTATACTGACCTCAATTTTCTCCA TCATATGTATATCTCCTTCTTATACTTAA CT (SEQ ID NO: 76) SAAT$_{Fa}$_F: AGTTAAGTATAAGAAGGAGATATACATAT GATGGGAGAAATTGAGGTCAGTATA (SEQ ID NO: 77) | Five PCR fragments including i) pdc$_{Zm}$- adhB$_{Zm}$ from pCT224[5], ii) fdh$_{Cb}^{opt}$ from pET29 $P_{T7lac}$::fdh$_{Cb}^{opt}$, iii) MCS1_MCS2 linker from pACYCDuet-1, iv) SAAT$_{Fa}$ from pDL1[5], and v) plasmid backbone with various copy numbers were assembled by Gibson Assembly method[6]. Specifically, pdc$_{Zm}$- adhB$_{Zm}$-fdh$_{Cb}$ and SAAT$_{Fa}$ were subcloned into the MCS1 and MCS2 of the duet vectors, respectively. |

| | | |
|---|---|---|
| The copy number of duet vectors are as follows: pACYCDuet-1, ~10; ~40; pRSFDuet-1, 100[4]. | | |
| Plasmid | Primers (5'→3') | Cloning strategies |
| | SAAT$_{Fa}$_R: AAATTTCGCAGCAGCGGTTTCTTTACCAGACTCGAGTTAAATTAAGGTCTTTGGAGATGC (SEQ ID NO: 78) BB_Duet_F: CGGATCCTGGCTGTGG (SEQ ID NO: 40) BB_Duet_R: CTCGAGTCTGGTAAAGAAACC (SEQ ID NO: 41) | |
| Submodule2/3/4 (SM2-SM3-SM4) for BB synthesis: Butanol + NADH + SAAT | | |
| pACYCDuet-1 P$_{T7lac}$::adhE2$_{Ca}$::fdh$_{Cb}$$^{opt}$-P$_{T7lac}$::SAAT$_{Fa}$ pETDuet-1 P$_{T7lac}$::adhE2$_{Ca}$::fdh$_{Cb}$$^{opt}$-P$_{T7lac}$::SAAT$_{Fa}$ pRSFDuet-1 P$_{T7lac}$::adhE2$_{Ca}$::fdh$_{Cb}$$^{opt}$-P$_{T7lac}$::SAAT$_{Fa}$ | adhE2$_{Ca}$_F: GCCATCACCATCATCACCACAGCCAGGATCCGATGAAAGTTACAAATCAAAAAGAACTAA (SEQ ID NO: 42) adhE2$_{Ca}$_R: TATATCTCCTTTTAAAATGATTTTATATAGATATCCTTAAGTTCAC (SEQ ID NO: 43) BB_Duet_F: CGGATCCTGGCTGTGG (SEQ ID NO: 40) BB_BB_R: AGGATATCTATATAAAATCATTTTAAAAGGAGATATAATGAAAATTGTGCTGGTTTTGTA (SEQ ID NO: 44) | pdc$_{Zm}$-adhB$_{Zm}$ in EB production modules were replaced with adhE2$_{Ca}$ from gDNA of C. acetobutylicum by Gibson Assembly method[6]. production modules |
| pRSFDuet-1 P$_{T7lac}$::trxA_adhE2$_{Ca}$$^{opt}$::fdh$_{Cb}$$^{opt}$-P$_{T7lac}$::SAAT$_{Fa}$ | SAAT$_{Fa}$_F: AGTTAAGTATAAGAAGGAGATATACATATGATGGAGAAAATTGAGGTCAGTATA (SEQ ID NO: 77) SAAT$_{Fa}$_R: AAATTTCGCAGCAGCGGTTTCTTTACCAGACTCGAGTTAAATTAAGGTCTTTGGAGATGC (SEQ ID NO: 78) BB_trxA_adhE2$_{Ca}$$^{opt}$_F: ATGTATATCTCCTTCTTATACTTAACTAATATACTAAGATGG (SEQ ID NO: 79) BB_Duet_R: CTCGAGTCTGGTAAAGAAACC (SEQ ID NO: 41) | trxA_ATF1$_{Sc}$$^{opt}$ in pRSFDuet-1 P$_{T7lac}$::trxA_adhE2$_{Ca}$$^{opt}$::fdh$_{Cb}$$^{opt}$-P$_{T7lac}$::trxA_ATF1$_{Sc}$$^{opt}$ was replaced with the SAAT$_{Fa}$ from pET29 P$_{T7lac}$::SAAT$_{Fa}$ by Gibson Assembly method[6]. |
| Wildtype AATs | | |
| pET29 P$_{T7lac}$::ATF1$_{Sc}$ | ATF1$_{Sc}$_F: ATAATTTTGTTTAACTTTAAGAAGGAGATATAGATATGAATGAAATCGATGAGAAAAAT (SEQ ID NO: 1) ATF1$_{Sc}$_R: TTTGTTAGCAGCCGGATCTCAGTGGTGGTGGTGGTGGTGGATAGGGCCTAAAAGGAGAG (SEQ ID NO: 2) BB_pET29_F: ATCCACCACCACCACC (SEQ ID NO: 3) BB_pET29_R: ATCTATATCTCCTTCTTAAAGTTAAACAAAATTATTTCTAG (SEQ ID NO: 4) | ATF1$_{Sc}$ in pDL004[7] was subcloned into pET29 by Gibson Assembly method[6]. |
| pET29 P$_{T7lac}$::SAAT$_{Fa}$ | SAAT$_{Fa}$_F: TAGAAATAATTTTGTTTAACTTTAAGAAGGAGATATAGATATGGAGAAAATTGAGGTCAG (SEQ ID NO: 80) SAAT$_{Fa}$_R: GTTAGCAGCCGGATCTCAGTGGTGGTGGTGGTGGTGGATAATTAAGGTCTTTGGAGATGC (SEQ ID NO: 81) BB_pET29_F: ATCCACCACCACCACC (SEQ ID NO: 3) BB_pET29_R: ATCTATATCTCCTTCTTAAAGTTAAACAAAATTATTTCTAG (SEQ ID NO: 4) | SAAT$_{Fa}$ in pDL001[7] was subcloned into pET29 by Gibson Assembly method[6]. |

-continued

The copy number of duet vectors are as follows: pACYCDuet-1, ~10; ~40; pRSFDuet-1, 100[4].

| Plasmid | Primers (5'→3') | Cloning strategies |
|---|---|---|
| Codon optimized genes by the U.S. Department of Energy (DOE) Joint Genome Institute (JGI) | | |
| pET29 $P_{T7lac}$::ATF1$_{Sc}^{opt}$<br>pET29 $P_{T7lac}$::SAAT$_{Fa}^{opt}$<br>pET29 $P_{T7lac}$::fdh$_{Cb}^{opt}$<br>pET29 $P_{T7lac}$::adhE2$_{Ca}^{opt}$ | univ_F:<br>CCTCTAGAAATAATTTTGTTTAACTTTAA GAAGGAGA (SEQ ID NO: 82)<br>univ_R:<br>CGGATCTCAGTGGTGGTGGT (SEQ ID NO: 83) | The plasmids were constructed by JGI. The synthesized genes were amplified and cloned into pET29 plasmid using the EcoRV restriction site. The genes were codon optimized to E. coli. |
| AATs with fusion partners | | |
| pET29 $P_{T7lac}$::malE_ATF1$_{Sc}$ | malE_ATF1$_{Sc}$_F:<br>TTTGTTTAACTTTAAGAAGGAGATATAGA TATGAAAATCGAAGAAGGTAAACTGGTAA TC (SEQ ID NO: 84)<br>malE_ATF1$_{Sc}$_R:<br>CTTGTTGCACGGGGGCCTGATTTTTCTCA TCGATTTCATTCTTGGTGATACGAGTCTG CG (SEQ ID NO: 85)<br>BB_pET29 ATF1$_{Sc}$_F:<br>AATGAAATCGATGAGAAAAATCAGGC (SEQ ID NO: 86)<br>BB_pET29 ATF1$_{Sc}$_R:<br>ATCTATATCTCCTTCTTAAAGTTAAACAA AATTATTTCTAG (SEQ ID NO: 4) | The start codon of ATF1$_{Sc}$ in pET29 $P_{T7}$::ATF1$_{Sc}$ was replaced with malE from gDNA of E. coli MG1655 by Gibson Assembly method[6]. |
| pET29 $P_{T7lac}$::nusA_ATF1$_{Sc}$ | nusA_ATF1$_{Sc}$_F:<br>ATTTTGTTTAACTTTAAGAAGGAGATATA GATATGAACAAAGAAATTTTGGCTGTAGT TG (SEQ ID NO: 87)<br>nusA_ATF1$_{Sc}$_R:<br>ATTLTTGTTGCACGGGGGCCTGATTTTTC TCATCGATTTCATTCGCTTCGTCACCGAA CC (SEQ ID NO: 88)<br>BB_pET29 ATF1$_{Sc}$_F:<br>AATGAAATCGATGAGAAAAATCAGGC (SEQ ID NO: 86)<br>BB_pET29 ATF1$_{Sc}$_R:<br>ATCTATATCTCCTTCTTAAAGTTAAACAA AATTATTTCTAG (SEQ ID NO: 4) | The start codon of ATF1$_{Sc}$ in pET29 $P_{T7}$::ATF1$_{Sc}$ was replaced with nudA from gDNA of E. coli MG1655 by Gibson Assembly method[6]. |
| pET29 $P_{T7lac}$::trxA_ATF1$_{Sc}$ | trxA_ATF1$_{Sc}$_F:<br>ATTTTGTTTAACTTTAAGAAGGAGATATA GATATGAGCGATAAAATTATTCACCTGAC TG (SEQ ID NO: 89)<br>trxA_ATF1$_{Sc}$_R:<br>CATTCTTGTTGCACGGGGGCCTGATTTTT CTCATCGATTTCATTCGCCAGGTTAGCGT CG (SEQ ID NO: 90)<br>BB_pET29 ATF1$_{Sc}$_F:<br>AATGAAATCGATGAGAAAAATCAGGC (SEQ ID NO: 86)<br>BB_pET29 ATF1$_{Sc}$_R:<br>ATCTATATCTCCTTCTTAAAGTTAAACAA AATTATTTCTAG (SEQ ID NO: 4) | The start codon of ATF1$_{Sc}$ in pET29 $P_{T7}$::ATF1$_{Sc}$ was replaced with trxA from gDNA of E. coli MG1655 by Gibson Assembly method[6]. |
| pET29 PT$_{7lac}$::malE_SAAT$_{Fa}$ | malE_ATF1$_{Sc}$_F:<br>TTTGTTTAACTTTAAGAAGGAGATATAGA TATGAAAATCGAAGAAGGTAAACTGGTAA TC (SEQ ID NO: 84)<br>malE_ATF1$_{Sc}$_R:<br>TGATGGTGTGTTTGGAATTTATACTGACC TCAATTTTCTCCTTGGTGATACGAGTCTG CG (SEQ ID NO: 91)<br>BB_pET29 SAAT$_{Fa}$_F:<br>GAGAAAATTGAGGTCAGTATAAATTCCAA AC (SEQ ID NO: 92)<br>BB_pET29 SAAT$_{Fa}$_R:<br>ATCTATATCTCCTTCTTAAAGTTAAACAA AATTATTTCTAG (SEQ ID NO: 4) | The start codon of ATF1$_{Sc}$ in pET29 $P_{T7}$::ATF1$_{Sc}$ was replaced with malE from gDNA of E. coli MG1655 by Gibson Assembly method[6]. |

The copy number of duet vectors are as follows: pACYCDuet-1, ~10; ~40; pRSFDuet-1, 100[4].

| Plasmid | Primers (5'→3') | Cloning strategies |
|---|---|---|
| pET29 $P_{T7lac}$::nusA_SAAT$_{Fa}$ | nusA_ATF1$_{Sc}$_F: ATTTTGTTTAACTTTAAGAAGGAGATATAGATATGAACAAAGAAATTTTGGCTGTAGTTG (SEQ ID NO: 87)<br>nusA_ATF1$_{Sc}$_R: GTTTGATGGTGTGTTTGGAATTTATACTGACCTCAATTTTCTCCGCTTCGTCACCGAACC (SEQ ID NO: 93)<br>BB_pET29 SAAT$_{Fa}$_F: GAGAAAATTGAGGTCAGTATAAATTCCAAAC (SEQ ID NO: 92)<br>BB_pET29 SAAT$_{Fa}$_R: ATCTATATCTCCTTCTTAAAGTTAAACAAAATTATTTCTAG (SEQ ID NO: 4) | The start codon of SAAT$_{Fa}$ in pET29 $P_{T7}$::SAAT$_{Fa}$ was replaced with nusA from gDNA of E. coli MG1655 by Gibson Assembly method[6]. |
| pET29 PT$_{7lac}$::trxA_SAAT$_{Fa}$ | trxA_ATF1$_{Sc}$_F: ATTTTGTTTAACTTTAAGAAGGAGATATAGATATGAGCGATAAAATTATTCACCTGACTG (SEQ ID NO: 89)<br>trxA_ATF1$_{Sc}$_R: GGTTTGATGGTGTGTTTGGAATTTATACTGACCTCAATTTTCTCCGCCAGGTTAGCGTCG (SEQ ID NO: 94)<br>BB_pET29 SAAT$_{Fa}$_F: GAGAAAATTGAGGTCAGTATAAATTCCAAAC (SEQ ID NO: 92)<br>BB_pET29 SAAT$p_a$_R: ATCTATATCTCCTTCTTAAAGTTAAACAAAATTATTTCTAG (SEQ ID NO: 4) | The start codon of SAAT$_{Fa}$ in pET29 $P_{T7}$::SAAT$_{Fa}$ was replaced with trxA from gDNA of E. coli MG1655 by Gibson Assembly method[6]. |

Co-expression of chaperones

| Plasmid | Primers (5'→3') | Cloning strategies |
|---|---|---|
| pACYC P$_{araB}$:tig | — | The chaperone plasmid kit was purchased from TaKaRa Bio Inc. (Cat. #3340). |
| pACYC P$_{araB}$:groES::groEL | — | |
| pACYC P$_{pzt-1}$::groES::groEL::tig | — | |
| pACYC P$_{araB}$::dnaK::dnaJ::grpE | — | |
| pACYC P$_{araB}$::dnaK::dnaJ::grpE-P$_{pzt-1}$::groES::groEL | — | |
| pACYC P$_{araB}$::groES::groEL (Amp$^R$) | Amp$^R$_F: ATTAGTTAAGTATAAGAAGGAGATATACATATGATGAACGAAATCGACGAAAAAAATCAG (SEQ ID NO: 95)<br>Amp$^R$_R: TTTCGCAGCAGCGGTTTCTTTACCAGACTCGAGCGGACCCAGTAACAAAGCTTTATATAT (SEQ ID NO: 96)<br>BB_groES/EL_F: CTCGAGTCTGGTAAAGAAACC (SEQ ID NO: 41)<br>BB_groES/EL_R: CATATGTATATCTCCTTCTTATACTTAACTAATATACT (SEQ ID NO: 57) | The chloramphenicol resistance marker of pACYC P$_{araB}$::groES::groEL was replaced with the ampicillin resistance marker from pETDuet-1 by Gibson Assembly method[6]. |

Abbreviations: F forward; R, reverse; BB, backbone; MSC, multiple cloning site.

What is claimed is:

1. A method of selectively synthesizing a butyryl-coenzyme A (CoA) derived ester via microbial biosynthesis, the method comprising:
selecting a target ester to be synthesized by microbial biosynthesis from the group consisting of butyl acetate, butyl butyrate, and ethyl butyrate;
providing a first expression vector, the first expression vector encoding a first plurality of enzymes that convert acetyl-CoA to butyryl-CoA selected from *Escherichia coli* atoB (atoB$_{Ec}$), *Clostridium acetobutylicum* Hbd (hbd$_{Ca}$), *Clostridium acetobutylicum* crt (crt$_{Ca}$), and *Treponema denticola* ter (terra);
providing a second expression vector that encodes a second plurality of enzymes selected from *Zymomonas mobilis* pdc (pdc$_{Zm}$) and *Zymomonas mobilis* adhB (adhB$_{Zm}$) or *Clostridium acetobutylicum* adhE2 (adhE2$_{Ca}$) for alcohol synthesis and *Candida boidinii* fdh (fdh$_{Cb}$) for facilitating the NADH production, wherein (i) at least one of the second plurality of enzymes facilitates production of nicotinamide adenine dinucleotide and hydrogen (NADH), (ii) at least one of the enzymes is an alcohol acetyltransferase selected from *Saccharomyces cerevisiae* ATF1 (ATF1$_{Sc}$) when an acetate ester is the target ester or Fragaria *ananassa* (cultivated strawberry) SAAT (SAAT$_{Fa}$) when an acylate ester is the target ester, and wherein (iii) at least one of the second plurality of enzymes selectively determines a pathway for either butanol or ethanol synthesis; and
inserting the first expression vector and the second expression vector into a microbial host cell selected from the group consisting of EcJWBA2, EcJWEB2, EcJWBB2, EcJWBA15, EcJWEB7, and EcJWBB8,
contacting the microbial cells with carbon source in culture media; and
culturing the microbial host to produce butyryl-coenzyme A derived esters;
wherein expression of the first and second expression vectors in the microbial host cell produces the target ester.

2. The method of claim 1, wherein the first expression vector and the second expression vector each comprise a predetermined copy number of genes encoding the respective first plurality of enzymes and second plurality of enzymes, and the method includes determining a predetermined copy number of genes that produces the highest concentration of the target ester in a culture comprising the microbial host cell.

3. The method of claim 1, wherein the first expression vector and the second expression vector each comprise a predetermined copy number of genes encoding the respective first plurality of enzymes and second plurality of enzymes, wherein the copy number of genes encoding the first plurality of enzymes is lower than the copy number of genes encoding the second plurality of enzymes.

4. The method of claim 2, wherein the first expression vector has a copy number in a range of 5 to 15 and the second expression vector has a copy number in a range of 80 to 120.

5. The method of claim 1, further comprising introducing a codon, fusion tag, co-expression of a chaperone or combinations thereof to improve the solubility of the alcohol acetyltransferase or *Clostridium acetobutylicum* adhE2.

6. The method of claim 5, wherein the alcohol acetyltransferase is ATF1$_{Sc}$ and introducing comprises a fusion tag.

7. The method of claim 5, wherein the alcohol acetyltransferase is SAAT$_{Fa}$ and introducing comprises a co-expression of a chaperone.

8. The method of claim 5, wherein the alcohol acetyltransferase is ATF1$_{Sc}$, the second expression vector is AdhE2$_{Ca}$, introducing comprises codon configuration and a fusion tag of thioredoxin 1 (TrxA) to both thereof, and inserting comprises induction conditions of 0.1 mM isopropyl-β-D-thiogalactopyranoside (IPTG) at 28° C., and optionally, an adhE-deficient chassis, or an adhE-deficient chassis and an anaerobic condition/pH adjustment.

9. The method of claim 5, wherein the microbial host cell is EcJWBA15.

10. The method of claim 5, wherein the alcohol acetyltransferase is SAAT$_{Fa}$, introducing comprises coexpression of the chaperone Gro ES/EL, and inserting comprising induction conditions of 0.1 mM isopropyl-β-D-thiogalactopyranoside (IPTG) at 28° C., an arabinose concentration of at least 1 mg/ml, and optionally, an anaerobic condition/pH adjustment.

11. The method of claim 10, wherein the microbial host cell is EcJWEB2 or EcJWEB7.

12. The method of claim 5, wherein the alcohol acetyltransferase is SAAT$_{Fa}$, the second expression vector is AdhE2$_{Ca}$, introducing comprises codon configuration and a fusion tag of thioredoxin 1 (TrxA) to AdhE2$_{Ca}$, and inserting comprises induction conditions of 0.1 mM isopropyl-β-D-thiogalactopyranoside (IPTG) at 37° C., and optionally, an anaerobic condition/pH adjustment.

13. The method of claim 12, wherein the microbial host cell is EcJWBB2 or EcJWBB8.

* * * * *

SEQUENCE LISTING

```
Sequence total quantity: 98
SEQ ID NO: 1              moltype = DNA   length = 59
FEATURE                   Location/Qualifiers
misc_feature              1..59
                          note = Synthetic: ATF1Sc_fwd
source                    1..59
                          mol_type = other DNA
                          organism = synthetic construct
SEQUENCE: 1
ataattttgt ttaactttaa gaaggagata tagatatgaa tgaaatcgat gagaaaaat    59

SEQ ID NO: 2              moltype = DNA   length = 59
FEATURE                   Location/Qualifiers
misc_feature              1..59
                          note = Synthetic: ATF1Sc_R
source                    1..59
                          mol_type = other DNA
                          organism = synthetic construct
SEQUENCE: 2
tttgttagca gccggatctc agtggtggtg gtggtggtgg ataggcccta aaaggagag    59

SEQ ID NO: 3              moltype = DNA   length = 16
FEATURE                   Location/Qualifiers
misc_feature              1..16
                          note = Synthetic: BB_ATF1Sc_fwd / BB_pET29_F
source                    1..16
                          mol_type = other DNA
                          organism = synthetic construct
SEQUENCE: 3
atccaccacc accacc                                                   16

SEQ ID NO: 4              moltype = DNA   length = 41
FEATURE                   Location/Qualifiers
misc_feature              1..41
                          note = Synthetic: BB_ATF1Sc_rev / BB_pET29_R
source                    1..41
                          mol_type = other DNA
                          organism = synthetic construct
SEQUENCE: 4
atctatatct ccttcttaaa gttaaacaaa attatttcta g                       41

SEQ ID NO: 5              moltype = DNA   length = 33
FEATURE                   Location/Qualifiers
misc_feature              1..33
                          note = Synthetic: P348W fwd
source                    1..33
                          mol_type = other DNA
                          organism = synthetic construct
SEQUENCE: 5
atttttatct gggcagattg ccgctcacaa cta                                33

SEQ ID NO: 6              moltype = DNA   length = 33
FEATURE                   Location/Qualifiers
misc_feature              1..33
                          note = Synthetic: P348W rev
source                    1..33
                          mol_type = other DNA
                          organism = synthetic construct
SEQUENCE: 6
ggcaatctgc ccagataaaa atatccgtaa gcc                                33

SEQ ID NO: 7              moltype = DNA   length = 33
FEATURE                   Location/Qualifiers
misc_feature              1..33
                          note = Synthetic: P348R_fwd
source                    1..33
                          mol_type = other DNA
                          organism = synthetic construct
SEQUENCE: 7
atttttatcc gtgcagattg ccgctcacaa cta                                33

SEQ ID NO: 8              moltype = DNA   length = 33
FEATURE                   Location/Qualifiers
misc_feature              1..33
                          note = Synthetic: P348R_rev
source                    1..33
                          mol_type = other DNA
                          organism = synthetic construct
```

```
SEQUENCE: 8
ggcaatctgc acggataaaa atatccgtaa gcc                                33

SEQ ID NO: 9            moltype = DNA   length = 33
FEATURE                 Location/Qualifiers
misc_feature            1..33
                        note = Synthetic: P348M_fwd
source                  1..33
                        mol_type = other DNA
                        organism = synthetic construct
SEQUENCE: 9
atttttatca tggcagattg ccgctcacaa cta                                33

SEQ ID NO: 10           moltype = DNA   length = 33
FEATURE                 Location/Qualifiers
misc_feature            1..33
                        note = Synthetic: P348M_rev
source                  1..33
                        mol_type = other DNA
                        organism = synthetic construct
SEQUENCE: 10
ggcaatctgc catgataaaa atatccgtaa gcc                                33

SEQ ID NO: 11           moltype = DNA   length = 33
FEATURE                 Location/Qualifiers
misc_feature            1..33
                        note = Synthetic: P348H_fwd
source                  1..33
                        mol_type = other DNA
                        organism = synthetic construct
SEQUENCE: 11
atttttatcc atgcagattg ccgctcacaa cta                                33

SEQ ID NO: 12           moltype = DNA   length = 33
FEATURE                 Location/Qualifiers
misc_feature            1..33
                        note = Synthetic: P348H_rev
source                  1..33
                        mol_type = other DNA
                        organism = synthetic construct
SEQUENCE: 12
ggcaatctgc atggataaaa atatccgtaa gcc                                33

SEQ ID NO: 13           moltype = DNA   length = 33
FEATURE                 Location/Qualifiers
misc_feature            1..33
                        note = Synthetic: P348K_fwd
source                  1..33
                        mol_type = other DNA
                        organism = synthetic construct
SEQUENCE: 13
atttttatca aagcagattg ccgctcacaa cta                                33

SEQ ID NO: 14           moltype = DNA   length = 33
FEATURE                 Location/Qualifiers
misc_feature            1..33
                        note = Synthetic: P348K_rev
source                  1..33
                        mol_type = other DNA
                        organism = synthetic construct
SEQUENCE: 14
ggcaatctgc tttgataaaa atatccgtaa gcc                                33

SEQ ID NO: 15           moltype = DNA   length = 33
FEATURE                 Location/Qualifiers
misc_feature            1..33
                        note = Synthetic: P348N_fwd
source                  1..33
                        mol_type = other DNA
                        organism = synthetic construct
SEQUENCE: 15
atttttatca atgcagattg ccgctcacaa cta                                33

SEQ ID NO: 16           moltype = DNA   length = 33
FEATURE                 Location/Qualifiers
misc_feature            1..33
                        note = Synthetic: P348N_rev
source                  1..33
                        mol_type = other DNA
```

```
                        organism = synthetic construct
SEQUENCE: 16
ggcaatctgc attgataaaa atatccgtaa gcc                                33

SEQ ID NO: 17           moltype = DNA  length = 33
FEATURE                 Location/Qualifiers
misc_feature            1..33
                        note = Synthetic: P348I_fwd
source                  1..33
                        mol_type = other DNA
                        organism = synthetic construct
SEQUENCE: 17
atttttatca ttgcagattg ccgctcacaa cta                                33

SEQ ID NO: 18           moltype = DNA  length = 33
FEATURE                 Location/Qualifiers
misc_feature            1..33
                        note = Synthetic: P348I_rev
source                  1..33
                        mol_type = other DNA
                        organism = synthetic construct
SEQUENCE: 18
ggcaatctgc aatgataaaa atatccgtaa gcc                                33

SEQ ID NO: 19           moltype = DNA  length = 33
FEATURE                 Location/Qualifiers
misc_feature            1..33
                        note = Synthetic: P348S_fwd
source                  1..33
                        mol_type = other DNA
                        organism = synthetic construct
SEQUENCE: 19
atttttatca cagcagattg ccgctcacaa cta                                33

SEQ ID NO: 20           moltype = DNA  length = 33
FEATURE                 Location/Qualifiers
misc_feature            1..33
                        note = Synthetic: P348S_rev
source                  1..33
                        mol_type = other DNA
                        organism = synthetic construct
SEQUENCE: 20
ggcaatctgc tgtgataaaa atatccgtaa gcc                                33

SEQ ID NO: 21           moltype = DNA  length = 33
FEATURE                 Location/Qualifiers
misc_feature            1..33
                        note = Synthetic: P348D_fwd
source                  1..33
                        mol_type = other DNA
                        organism = synthetic construct
SEQUENCE: 21
atttttatcg atgcagattg ccgctcacaa cta                                33

SEQ ID NO: 22           moltype = DNA  length = 33
FEATURE                 Location/Qualifiers
misc_feature            1..33
                        note = Synthetic: P348D_rev
source                  1..33
                        mol_type = other DNA
                        organism = synthetic construct
SEQUENCE: 22
ggcaatctgc atcgataaaa atatccgtaa gcc                                33

SEQ ID NO: 23           moltype = DNA  length = 33
FEATURE                 Location/Qualifiers
misc_feature            1..33
                        note = Synthetic: P348C_fwd
source                  1..33
                        mol_type = other DNA
                        organism = synthetic construct
SEQUENCE: 23
atttttatct gcgcagattg ccgctcacaa cta                                33

SEQ ID NO: 24           moltype = DNA  length = 33
FEATURE                 Location/Qualifiers
misc_feature            1..33
                        note = Synthetic: P348C_rev
source                  1..33
```

```
                         mol_type = other DNA
                         organism = synthetic construct
SEQUENCE: 24
ggcaatctgc gcagataaaa atatccgtaa gcc                                    33

SEQ ID NO: 25            moltype = DNA   length = 33
FEATURE                  Location/Qualifiers
misc_feature             1..33
                         note = Synthetic: P348A_fwd
source                   1..33
                         mol_type = other DNA
                         organism = synthetic construct
SEQUENCE: 25
atttttatcg ctgcagattg ccgctcacaa cta                                    33

SEQ ID NO: 26            moltype = DNA   length = 33
FEATURE                  Location/Qualifiers
misc_feature             1..33
                         note = Synthetic: P348A_rev
source                   1..33
                         mol_type = other DNA
                         organism = synthetic construct
SEQUENCE: 26
ggcaatctgc agcgataaaa atatccgtaa gcc                                    33

SEQ ID NO: 27            moltype = DNA   length = 33
FEATURE                  Location/Qualifiers
misc_feature             1..33
                         note = Synthetic: P348Q_fwd
source                   1..33
                         mol_type = other DNA
                         organism = synthetic construct
SEQUENCE: 27
atttttatcc aggcagattg ccgctcacaa cta                                    33

SEQ ID NO: 28            moltype = DNA   length = 33
FEATURE                  Location/Qualifiers
misc_feature             1..33
                         note = Synthetic: P348Q_rev
source                   1..33
                         mol_type = other DNA
                         organism = synthetic construct
SEQUENCE: 28
ggcaatctgc ctggataaaa atatccgtaa gcc                                    33

SEQ ID NO: 29            moltype = DNA   length = 1356
FEATURE                  Location/Qualifiers
misc_feature             1..1356
                         note = Synthetic: SAATFa
source                   1..1356
                         mol_type = other DNA
                         organism = synthetic construct
SEQUENCE: 29
atggaaaaaa tcgaagtctc aattaactcc aagcatacca tcaaaccctc tacctctagt        60
accccgctac aaccctataa actgacctta ctggatcagc tgacgccacc agcctatgtc       120
ccgatcgtgt ttttttaccc gatcaccgat cacgatttta atctgccgca gacgctggcg       180
gacttacgtc aagctctgtc ggagactctc acgctgtatt atcccctgag cggacgtgtt       240
aaaaacaatt tgtatattga tgactttgag gaaggcgtgc cgtacttaga agcgcgtgta       300
aattgcgata tgaccgattt tctgcgtctg cgcaaaattg agtgcctgaa cgaatttgta       360
ccgattaaac ctttcagtat ggaagcaatt agcgatgaac gttacccgtt gctgggcgtc       420
caggttaatg ttttttgattc gggcatcgcg atcggagtgt cagtcagtca taaattgata       480
gatggtggca cggcagattg tttccttaaa tcttggggcg ccgtgtttcg tggctgccgt       540
gaaaatatta tccaccccgag tctgagtgag gctgcgctgt tgttcccccc acgcgatgac       600
ctgccagaaa aatacgttga ccaaatggag gccctgtcgt ttgcggggaa aaaagtcgcc       660
acccgacgct ttgttttcgg tgtgaaagcg attagcagca ttcaagacga gcaaaaatct       720
gagagcgtcc caaaaccgtc tcgcgttcat gccgtgacag gcttcttatg gaagcacctg       780
atagctgcgt cccgcgcatt gacaagtggg actacatcga cccgtctgtc aattgccgcg       840
caagcagtga acctgcgtac tcgcatgaac atggaaaccg ttttagataa cgctacgggt       900
aacctgttct ggtgggccca ggctccctta gaactgctgc ataccaccgc ggagatttct       960
gaccttaaac tgtgtgatct ggttaacttg ctgaacggat ccgtcaagca gtgcaatggc      1020
gactatttcg agacctttaa aggtaaagaa ggctatggcc ggatgtgtga atacttggat      1080
ttccagcgaa caatgtcgtc catggaaccg gctccggaca tttatctgtt tcatcctgg       1140
actaactttt ttaacccgtt ggatttcggc tgggccgca cctcctggat ggagttgca        1200
ggtaaaattg agagtgcgtc ctgcaaattt ataatcctcg tgcccacaca gtggttccg       1260
ggtatcgagg cctggagtca cttggaggaa gaaaaaatgg ccatgctcga acaggatccg      1320
cattttctag cgctggcgtc acctaaaacc ctgatc                                 1356

SEQ ID NO: 30            moltype = DNA   length = 1575
FEATURE                  Location/Qualifiers
```

```
misc_feature            1..1575
                        note = Synthetic: ATF1Scopt
source                  1..1575
                        mol_type = other DNA
                        organism = synthetic construct
SEQUENCE: 30
atgaacgaaa tcgacgaaaa aaatcaggcg ccagttcagc aggagtgtct gaaagaaatg      60
attcaaaatg gtcatgcgcg tagaatgggt tcagtggagg attttgtacgt tgcgctgaat   120
cgccaaaacc tttaccgtaa cttttgcacg tatggtgagc tgtcagatta ctgcactcgt   180
gatcagttga cgctggcgct ccgtgaaatc tgcttaaaaa acccgactct tctgcatatt   240
gtgttaccga cgcgctggcc gaaccacgaa aactattata gaagcagtga atattacagc   300
cgtcctcacc ctgtgcacga ctacatatcg gtcttacagg aattaaagct gtcgggcgtg   360
gtgttgaatg aacaacctga atactcagcg gttatgaaac agattctgga agaattcaaa   420
aatagcaagg gcagctatac ggctaagatc tttaaactta ccaccaccct gacaatccca   480
tacttcggcc ccacaggccc atcttggcgc ttgatttgtt tgcccgaaga gcacactgaa   540
aaatggaaga aattcatatt tgtgagcaat cattgcatgt cagatggccg ctcctccatt   600
catttcttcc acgatctgcg tgacgaactt aacaatatta aaactccgcc gaagaagcta   660
gattacatct tcaaatacga agaagactac cagctgctgc gtaaactgcc ggagccgatc   720
gaaaaagtga ttgattttcg tccgccgtat ctttttattc ctaaatccct cttatcggga   780
tttatataca atcaccttcg attttcatca aaagggtat gtatgcgcat ggatgatgtg    840
gaaaagacga cgacgtcgt taccgaaatc attaatatta gcccgactga atttcaagcg    900
ataaaagcaa acatcaaatc gaacatccag ggcaaatgta ccattactcc ctttctccat   960
gtttgttggt tcgtgtctct gcataaatgg ggcaagttct ttaaacctct gaactttgaa  1020
tggctgactg atattttcat ccctgcggac tgccgctctc agttgcctga tgacgatgaa  1080
atgcgccaga tgtaccggta tggtgcgaat gtgggcttca ttgacttcac tccgtggatc  1140
agcgaatttg acatgaatga taacaaagaa aattttttgc cactgattga gcactatcat  1200
gaggtgatca gtgaggcgct tcgtaacaaa aaacatctgc atggtttggg tttcaacatt  1260
cagggtttcg tacaaaagta cgtgaacata gataaagtca tgtgtgaccg ggctattggt  1320
aaacgtcgtg gcgtactct actcagcaat gttggtctgt tcaatcaact gaagaacct   1380
gacgccaaat attctatttg cgacttagct tttggccaat tccagggcag ctggcaccag  1440
gcttttagtc tcggtgtgtg ctctacgaat gttaaggta tgaatatcgt cgtcgcgtcg  1500
acaaaaaacg tcgtaggttc acaggagtcc ctggaagagc tttgtagcat atataaagct   1560
ttgttactgg gtccg                                                    1575

SEQ ID NO: 31           moltype = DNA  length = 1356
FEATURE                 Location/Qualifiers
misc_feature            1..1356
                        note = Synthetic: SAATFaopt
source                  1..1356
                        mol_type = other DNA
                        organism = synthetic construct
SEQUENCE: 31
atggaaaaaa tcgaagtctc aattaactcc aagcatacca tcaaaccctc tacctctagt     60
acccccgctac aaccctataa actgacctta ctggatcagc tgacgccacc agcctatgtc   120
ccgatcgtgt ttttttaccc gatcaccgat cacgatttta atctgccgca gacgctggcg   180
gacttacgtc aagctctgtc ggagactctc acgctgtatt atcccctgag cggacgtgtt   240
aaaaacaatt tgtatattga tgactttgag gaaggcgtgc cgtacttaga agcgcgtgta   300
aattgcgata tgaccgattt tctgcgtctg cgcaaaattg agtgcctgaa cgaatttgta   360
ccgattaaac ctttcagtat ggaagcaatt agcgatgaac gttacccgtt gctgggcgtc   420
caggttaatg ttttttgattc gggcatcgcg atcgagtgt cagtcagtca taaattgata   480
gatggtggca cggcagattg tttccttaaa tcttgggagg ccgtgtttcg tggctgccag   540
gaaaatatta tccacccgag tctgagtgag gctgcgctgt tgttcccccc acgcgatgac   600
ctgccagaaa aatacgttga ccaaatggag gccctgtggt ttgcggggaa aaagtcgcc    660
acccgacgct ttgttttcgg tgtgaaagcg attagcagca ttcaagacga agcaaaatct   720
gagagcgtcc caaaaccgtc tcgcgttcat gccgtgacgg gcttcttatg gaagcacctg   780
atagctgcgt cccgcgcatt gacaagtggg actacatcga cccgtctgtc aattgccgcg   840
caagcagtaa acctgcgtac tcgcatgaac atggaaaccg ttttagataa cgctacgggt   900
aacctgttct ggtgggccca ggcgatccta gaactgtcgc ataccacccc ggagatttct   960
gaccttaaac tgtgtgatct ggttaacttg ccgtcaagca gtcaatggc                1020
gactatttcg agaccttaa aggtaaagaa ggctatggcc ggatgtgtga atacttggat   1080
ttccagcgaa caatgtcgtc catggaaccg gctccggaca tttatctgtt tcatcctgg   1140
actaactttt taacccgtt ggatttcggc tggggccgca cctcctggat tggagttgca   1200
ggtaaaattg agagtgcgtc ctgcaaattt ataatcctcg tgcccacaca gtgcggttcg   1260
ggtatcgagg cctgggtcaa cttggaggaa gaaaaaatgg ccatgctcga acaggatccg   1320
cattttctag cgctggcgtc acctaaaacc ctgatc                             1356

SEQ ID NO: 32           moltype = DNA  length = 2574
FEATURE                 Location/Qualifiers
misc_feature            1..2574
                        note = Synthetic: adhE2Caopt
source                  1..2574
                        mol_type = other DNA
                        organism = synthetic construct
SEQUENCE: 32
atgaaagtga ccaatcaaaa agagctgaaa cagaaactga cgaacttcg tgaagcgcaa     60
aaaaattcg caacctacac gcaggagcag gtggataaaa ttttcaagca gtgtgcgatt   120
gcggcggcga aagagcggat taacctggcg aagctggcgg tggaagaaac cgggattggg   180
ctggtggagg acaaaatcat caagaaccat tttgccgcgg aatacattta taacaagtac   240
aaaaacgaaa gacgtgtgg tattattgat cacgatgact ccctgggcat cacgaaggtg   300
```

```
gcagaaccga tcggtatcgt cgctgcgatc gttccgacga ccaatcccac gtcaacggcg    360
atctttaaaa gtttgattag cctgaaaact cgtaacgcca tcttcttttc ccccaccc     420
cgtgcgaaaa agagcaccat cgcggccgcg aaacttatct tggatgctgc cgtgaaggcg    480
ggggccccga agaacatcat tggctggatc gacgagccgt caattgagct cagccaagac    540
ctgatgagcg aagcggatat tattctggcg acaggcgtc cgagcatggt taaagcgggc     600
tactcgtctg gcaaaccagc cattggtgtt ggagccggca acactccggc aattattgat    660
gagagcgccg atatcgatat ggcggttagt agcatcatcc tgtctaaaac ctacgacaat    720
ggtgtgatct cgcgcgagcga acaaagtatt ctcgtcatga actctatcta tgaaaaggtg   780
aaagaagagt ttgtgaagcg tggtagctat atcctgaacc agaacgaaat tgccaaaatc    840
aaagaaacaa tgtttaagaa tggagctatc aatgccgata tcgttggtaa aagtgcctat    900
attatcgcga aaatggctgg catcgaagtc ccgcaaacta ccaaaatttt aattggtgag    960
gttcagagcg tggaaaaatc ggagttgttt cccacgaaa aactgtcgcc ggtattagca    1020
atgtataaag taaaagattt tgacgaagcc ctgaaaaagg cccagcgctt aattgaatta   1080
ggcggctctg gtcatacctc atcgctgtac atcgatagcc agaacaataa agataaagtt   1140
aaagaatttg gcctggccat gaagacaagt cgcacgttta tcaatatgcc ttcaagccaa   1200
ggcgcctcgg gtgatcttta aattttgca atcgcgccga gcttcactct gggttgtggg   1260
acgtggggtg gcaatagcgt ctcacagaat gtcgaaccga agcatttact gaacatcaaa   1320
tcagtcgtga aacgccgtga aaacatgctg tggttcaaag tgccgcaaaa aatctatttc   1380
aagtatggtt gcctgcgatt cgcactgaag gaactgaaag atatgaacaa aaacgtgcg   1440
tttattgtta ccgataagga cctgtttaaa ctgggctatg tgaacaaat tactaaagtt   1500
ctggatgaaa ttgatattaa atactcgatc ttcaccgata ttaaaagtga ccctacgatc   1560
gatgcgtga aaaaggcgc gaaagaaatg cttaactttg aaccggatac cattatcgat    1620
attggggtg ttctccgat ggatgcggcc aaagttatgc atctgttgta tgagtatccg     1680
gaagccgaga ttgagaacct ggctatcaat tttatggaca tccgaaagcg gatctgcaac   1740
ttcccaaagt taggtacgaa agccattagc gtagccattc ctaccaccgc gggtaccggt   1800
agtgaggcca cgccgttcgc ggtgattacc aatgatgaca ccggtatgaa atacccgttg   1860
accagctatg aattaacacc aaacatggca attatcgata cggaactgat gctgaacatg   1920
cctcgtaaac ttcagcggc gactgggatt gatgccctgg ttcacgcgat tgaagcatac   1980
gtgagtgtga tggcaaccga ttataccgat gagctggccc tgcgcgctat caaaatgatc   2040
ttcaaatatc tgccgcgtgc ctacaaaaac ggcaccaatg atatcgaagc tcgagaaaa    2100
atggcgcatg cctcaaacat cgcagggatg gcattcgcga acgcgtttct gggcgtgtgc   2160
cactctatgg cacacaaact gggtgcgatg caccatgtgc cacacggcat tgcatgtgct   2220
gtgttaattg aagaagttat taaatataat gcgaccgact gcccaaccaa acaaaccgcg   2280
tttccgcaat acaaaagccc gaatgctaag cgtaaatacg ctgaaattgc ggaatatctg   2340
aatctgaaag gcacctctga taccgagaaa gtgaccgccc tgattgaagc tatctctaag   2400
ttaaaaattg atctgagcat cccgcagaac atctcggcag ctgggatcaa taaaaaagat   2460
ttttacaata ccttggataa aatgtctgaa ctcgcgttcg acgatcaatg cacaaccgcc   2520
aacccacgct atccgctgat ctccgaactc aaagacattt acataaagag tttc         2574

SEQ ID NO: 33         moltype = DNA   length = 1092
FEATURE               Location/Qualifiers
misc_feature          1..1092
                      note = Synthetic: fdhCbopt
source                1..1092
                      mol_type = other DNA
                      organism = synthetic construct
SEQUENCE: 33
atgaaaattg tgctggtttt gtatgatgcg ggaaagcatg cggcggacga agaaaagctt     60
tatgggtgta ccgaaaacaa actgggcatt gctaactggc tgaaagacca gggtcatgaa   120
ctcattacca cgagcgataa agaaggcgaa acctccgaat tagacaagca tattccggat   180
gcggacatta ttatcaccac tccgtttcac ccggcataca ttaccaaaga acgtttagat   240
aaagctaaaa acctgaaact ggtcgtcgtc gccggtgtcg gcagtgatca cattgattta   300
gattatatta accagacggg caaaaaaatc tccgtgttag aggtaacagg tagcaacgtc   360
gtctcagtgg cggaacacgt ggtaatgacc atgctagttt tggtccgtaa ctttgttccg   420
gcacatgaac aaattatcaa tcatgactgg gaggtcgtgc ctatcgcgaa agatgcctac   480
gatattgagg gcaaaaccat tgcgactatt ggtgcgggc gcatcggtta tcgtgtactt   540
gaacgccttc ttccgtttaa cccgaaggag ctgttgtact acgactacca ggcgttacca   600
aaagaggctg aagaaaaagt gggcgcgcgc cgtgttgaga atattgagga actcgttgca   660
caggcagata ttgttaccgt gaatcgcgcc ctgcacgcgg gaaccaaagg tttgatcaac   720
aaagaactac tgagtaaatt taaaaaaggc gcctggctcg tgaatacgac tcgtggtcag   780
atttgcgtag ctgaagatgt ggccgcagca ctggagagcg tcagctgcg cggctatggg    840
ggcgacgtgt ggttccccca accggcacct aaagatcatc cctggcgtga tatgcgtaac   900
aaatacggcg caggcaatgc tatgaccccg cattactccg gcacaacctt ggacgcacaa   960
actcgctacg cggaaggtac taagaacatt ctggagtcgt tttttacggg caagtttgat   1020
taccgaccgc aggataataa tcttctgaac ggtgaatacg tgaccaaggc gtatggtaaa   1080
cacgataaaa aa                                                       1092

SEQ ID NO: 34         moltype = DNA   length = 60
FEATURE               Location/Qualifiers
misc_feature          1..60
                      note = Synthetic: CrCoA_F
source                1..60
                      mol_type = other DNA
                      organism = synthetic construct
SEQUENCE: 34
cagcagccat caccatcatc accacagcca ggatccgatg aaaaattgtg tcatcgtcag   60

SEQ ID NO: 35         moltype = DNA   length = 26
FEATURE               Location/Qualifiers
```

```
misc_feature             1..26
                         note = Synthetic: CrCoA_R
source                   1..26
                         mol_type = other DNA
                         organism = synthetic construct
SEQUENCE: 35
ctatctattt ttgaagcctt caattt                                    26

SEQ ID NO: 36            moltype = DNA   length = 60
FEATURE                  Location/Qualifiers
misc_feature             1..60
                         note = Synthetic: MCS1_MCS2 linker_F
source                   1..60
                         mol_type = other DNA
                         organism = synthetic construct
SEQUENCE: 36
gctttcatag agaaagaaa aattgaaggc ttcaaaaata gataggaatt cgagctcggc  60

SEQ ID NO: 37            moltype = DNA   length = 60
FEATURE                  Location/Qualifiers
misc_feature             1..60
                         note = Synthetic: MCS1_MCS2 linker_R
source                   1..60
                         mol_type = other DNA
                         organism = synthetic construct
SEQUENCE: 37
attgttccta accattggtt ttacaatcat catatgtata tctccttctt atacttaact  60

SEQ ID NO: 38            moltype = DNA   length = 54
FEATURE                  Location/Qualifiers
misc_feature             1..54
                         note = Synthetic: terTd_F
source                   1..54
                         mol_type = other DNA
                         organism = synthetic construct
SEQUENCE: 38
agttaagtat aagaaggaga tatacatatg atgattgtaa aaccaatggt tagg       54

SEQ ID NO: 39            moltype = DNA   length = 60
FEATURE                  Location/Qualifiers
misc_feature             1..60
                         note = Synthetic: terTd_R
source                   1..60
                         mol_type = other DNA
                         organism = synthetic construct
SEQUENCE: 39
tcaaatttcg cagcagcggt ttctttacca gactcgagtt aaatcctgtc gaacctttct  60

SEQ ID NO: 40            moltype = DNA   length = 16
FEATURE                  Location/Qualifiers
misc_feature             1..16
                         note = Synthetic: BB_Duet_F / BB_BA_FP_adhE2Caopt_F
source                   1..16
                         mol_type = other DNA
                         organism = synthetic construct
SEQUENCE: 40
cggatcctgg ctgtgg                                               16

SEQ ID NO: 41            moltype = DNA   length = 21
FEATURE                  Location/Qualifiers
misc_feature             1..21
                         note = Synthetic: BB_Duet_R / BB_groES/EL_F
source                   1..21
                         mol_type = other DNA
                         organism = synthetic construct
SEQUENCE: 41
ctcgagtctg gtaaagaaac c                                         21

SEQ ID NO: 42            moltype = DNA   length = 60
FEATURE                  Location/Qualifiers
misc_feature             1..60
                         note = Synthetic: adhE2Ca_F
source                   1..60
                         mol_type = other DNA
                         organism = synthetic construct
SEQUENCE: 42
gccatcacca tcatcaccac agccaggatc cgatgaaagt tacaaatcaa aaagaactaa  60

SEQ ID NO: 43            moltype = DNA   length = 46
```

```
FEATURE                 Location/Qualifiers
misc_feature            1..46
                        note = Synthetic: adhE2Ca_R
source                  1..46
                        mol_type = other DNA
                        organism = synthetic construct
SEQUENCE: 43
tatatctcct tttaaaatga ttttatatag atatccttaa gttcac              46

SEQ ID NO: 44           moltype = DNA   length = 60
FEATURE                 Location/Qualifiers
misc_feature            1..60
                        note = Synthetic: fdhCbopt_F / BB_BB_R
source                  1..60
                        mol_type = other DNA
                        organism = synthetic construct
SEQUENCE: 44
aggatatcta tataaaatca ttttaaaagg agatataatg aaaattgtgc tggttttgta  60

SEQ ID NO: 45           moltype = DNA   length = 60
FEATURE                 Location/Qualifiers
misc_feature            1..60
                        note = Synthetic: fdhCbopt_R
source                  1..60
                        mol_type = other DNA
                        organism = synthetic construct
SEQUENCE: 45
ttgtcgacct gcaggcgcgc cgagctcgaa ttcttatttt ttatcgtgtt taccatacgc  60

SEQ ID NO: 46           moltype = DNA   length = 18
FEATURE                 Location/Qualifiers
misc_feature            1..18
                        note = Synthetic: MCS1_MCS2 linker_BA_F
source                  1..18
                        mol_type = other DNA
                        organism = synthetic construct
SEQUENCE: 46
taagaattcg agctcggc                                              18

SEQ ID NO: 47           moltype = DNA   length = 42
FEATURE                 Location/Qualifiers
misc_feature            1..42
                        note = Synthetic: MCS1_MCS2 linker_BA_R
source                  1..42
                        mol_type = other DNA
                        organism = synthetic construct
SEQUENCE: 47
gatttcattc atcatatgta tatctccttc ttatacttaa ct                   42

SEQ ID NO: 48           moltype = DNA   length = 60
FEATURE                 Location/Qualifiers
misc_feature            1..60
                        note = Synthetic: ATF1Sc_F
source                  1..60
                        mol_type = other DNA
                        organism = synthetic construct
SEQUENCE: 48
atattagtta agtataagaa ggagatatac atatgatgaa tgaaatcgat gagaaaaatc  60

SEQ ID NO: 49           moltype = DNA   length = 60
FEATURE                 Location/Qualifiers
misc_feature            1..60
                        note = Synthetic: ATF1Sc_R
source                  1..60
                        mol_type = other DNA
                        organism = synthetic construct
SEQUENCE: 49
cgttcaaatt tcgcagcagc ggtttcttta ccagactcga gctaagggcc taaaaggaga  60

SEQ ID NO: 50           moltype = DNA   length = 27
FEATURE                 Location/Qualifiers
misc_feature            1..27
                        note = Synthetic: ATF1Scopt_F
source                  1..27
                        mol_type = other DNA
                        organism = synthetic construct
SEQUENCE: 50
atgaacgaaa tcgacgaaaa aaatcag                                    27
```

```
SEQ ID NO: 51              moltype = DNA  length = 24
FEATURE                    Location/Qualifiers
misc_feature               1..24
                           note = Synthetic: ATF1Scopt_R
source                     1..24
                           mol_type = other DNA
                           organism = synthetic construct
SEQUENCE: 51
cggacccagt aacaaagctt tata                                        24

SEQ ID NO: 52              moltype = DNA  length = 59
FEATURE                    Location/Qualifiers
misc_feature               1..59
                           note = Synthetic: BB_BA_ATF1Scopt_F
source                     1..59
                           mol_type = other DNA
                           organism = synthetic construct
SEQUENCE: 52
gagctttgta gcatatataa agctttgtta ctgggtccgc tcgagtctgg taaagaaac   59

SEQ ID NO: 53              moltype = DNA  length = 60
FEATURE                    Location/Qualifiers
misc_feature               1..60
                           note = Synthetic: BB_BA_ATF1Scopt_R
source                     1..60
                           mol_type = other DNA
                           organism = synthetic construct
SEQUENCE: 53
gcgcctgatt tttttcgtcg atttcgttca tcatatgtat atctccttct tatacttaac  60

SEQ ID NO: 54              moltype = DNA  length = 60
FEATURE                    Location/Qualifiers
misc_feature               1..60
                           note = Synthetic: malE_ATF1Scopt_F
source                     1..60
                           mol_type = other DNA
                           organism = synthetic construct
SEQUENCE: 54
atattagtta agtataagaa ggagatatac atatgatgaa atcgaagaa ggtaaactgg   60

SEQ ID NO: 55              moltype = DNA  length = 59
FEATURE                    Location/Qualifiers
misc_feature               1..59
                           note = Synthetic: malE_ATF1Scopt_R
source                     1..59
                           mol_type = other DNA
                           organism = synthetic construct
SEQUENCE: 55
cctgctgaac tggcgcctga ttttttttcgt cgatttcgtt cttggtgata cgagtctgc  59

SEQ ID NO: 56              moltype = DNA  length = 24
FEATURE                    Location/Qualifiers
misc_feature               1..24
                           note = Synthetic: BB_BA_ FP_ATF1Scopt_F
source                     1..24
                           mol_type = other DNA
                           organism = synthetic construct
SEQUENCE: 56
aacgaaatcg acgaaaaaaa tcag                                        24

SEQ ID NO: 57              moltype = DNA  length = 38
FEATURE                    Location/Qualifiers
misc_feature               1..38
                           note = Synthetic: BB_BA_FP_ATF1Scopt_R / BB_groES/EL_R
source                     1..38
                           mol_type = other DNA
                           organism = synthetic construct
SEQUENCE: 57
catatgtata tctccttctt atacttaact aatatact                         38

SEQ ID NO: 58              moltype = DNA  length = 60
FEATURE                    Location/Qualifiers
misc_feature               1..60
                           note = Synthetic: nusA_ATF1Scopt_F
source                     1..60
                           mol_type = other DNA
                           organism = synthetic construct
SEQUENCE: 58
atattagtta agtataagaa ggagatatac atatgatgaa caaagaaatt tggctgtag   60
```

```
SEQ ID NO: 59            moltype = DNA  length = 60
FEATURE                  Location/Qualifiers
misc_feature             1..60
                         note = Synthetic: nusA_ATF1Scopt_R
source                   1..60
                         mol_type = other DNA
                         organism = synthetic construct
SEQUENCE: 59
cactcctgct gaactggcgc ctgattttt tcgtcgattt cgttcgcttc gtcaccgaac    60

SEQ ID NO: 60            moltype = DNA  length = 60
FEATURE                  Location/Qualifiers
misc_feature             1..60
                         note = Synthetic: trxA_ATF1Scopt_F
source                   1..60
                         mol_type = other DNA
                         organism = synthetic construct
SEQUENCE: 60
tattagttaa gtataagaag gagatataca tatgatgagc gataaaatta ttcacctgac   60

SEQ ID NO: 61            moltype = DNA  length = 54
FEATURE                  Location/Qualifiers
misc_feature             1..54
                         note = Synthetic: trxA_ATF1Scopt_R
source                   1..54
                         mol_type = other DNA
                         organism = synthetic construct
SEQUENCE: 61
ctgctgaact ggcgcctgat ttttttcgtc gatttcgttc gccaggttag cgtc          54

SEQ ID NO: 62            moltype = DNA  length = 25
FEATURE                  Location/Qualifiers
misc_feature             1..25
                         note = Synthetic: adhE2Caopt_F
source                   1..25
                         mol_type = other DNA
                         organism = synthetic construct
SEQUENCE: 62
atgaaagtga ccaatcaaaa agagc                                          25

SEQ ID NO: 63            moltype = DNA  length = 34
FEATURE                  Location/Qualifiers
misc_feature             1..34
                         note = Synthetic: adhE2Caopt_R
source                   1..34
                         mol_type = other DNA
                         organism = synthetic construct
SEQUENCE: 63
ttagaaactc tttatgtaaa tgtctttgag ttcg                                34

SEQ ID NO: 64            moltype = DNA  length = 60
FEATURE                  Location/Qualifiers
misc_feature             1..60
                         note = Synthetic: BB_BA_adhE2Caopt_F
source                   1..60
                         mol_type = other DNA
                         organism = synthetic construct
SEQUENCE: 64
caaagacatt tacataaaga gtttctaaaa ggagatataa tgaaaattgt gctggttttg   60

SEQ ID NO: 65            moltype = DNA  length = 58
FEATURE                  Location/Qualifiers
misc_feature             1..58
                         note = Synthetic: BB_BA_adhE2Caopt_R
source                   1..58
                         mol_type = other DNA
                         organism = synthetic construct
SEQUENCE: 65
gttcagtttc tgtttcagct cttttttgatt ggtcactttc atcggatcct ggctgtgg     58

SEQ ID NO: 66            moltype = DNA  length = 60
FEATURE                  Location/Qualifiers
misc_feature             1..60
                         note = Synthetic: malE_adhE2Caopt_F
source                   1..60
                         mol_type = other DNA
                         organism = synthetic construct
SEQUENCE: 66
```

```
gcagccatca ccatcatcac cacagccagg atccgatgaa aatcgaagaa ggtaaactgg    60

SEQ ID NO: 67          moltype = DNA   length = 59
FEATURE                Location/Qualifiers
misc_feature           1..59
                       note = Synthetic: malE_adhE2Caopt_R
source                 1..59
                       mol_type = other DNA
                       organism = synthetic construct
SEQUENCE: 67
cgttcagttt ctgtttcagc tcttttgat tggtcacttt cttggtgata cgagtctgc     59

SEQ ID NO: 68          moltype = DNA   length = 24
FEATURE                Location/Qualifiers
misc_feature           1..24
                       note = Synthetic: BB_BA_FP_adhE2Caopt_R
source                 1..24
                       mol_type = other DNA
                       organism = synthetic construct
SEQUENCE: 68
aaagtgacca atcaaaaaga gctg                                          24

SEQ ID NO: 69          moltype = DNA   length = 60
FEATURE                Location/Qualifiers
misc_feature           1..60
                       note = Synthetic: nusA_adhE2Caopt_F
source                 1..60
                       mol_type = other DNA
                       organism = synthetic construct
SEQUENCE: 69
gcagccatca ccatcatcac cacagccagg atccgatgaa caaagaaatt ttggctgtag    60

SEQ ID NO: 70          moltype = DNA   length = 56
FEATURE                Location/Qualifiers
misc_feature           1..56
                       note = Synthetic: nusA_adhE2Caopt_R
source                 1..56
                       mol_type = other DNA
                       organism = synthetic construct
SEQUENCE: 70
cgttcagttt ctgtttcagc tcttttgat tggtcacttt cgcttcgtca ccgaac         56

SEQ ID NO: 71          moltype = DNA   length = 60
FEATURE                Location/Qualifiers
misc_feature           1..60
                       note = Synthetic: trxA_adhE2Caopt_F
source                 1..60
                       mol_type = other DNA
                       organism = synthetic construct
SEQUENCE: 71
cagccatcac catcatcacc acagccagga tccgatgagc gataaaatta ttcacctgac    60

SEQ ID NO: 72          moltype = DNA   length = 55
FEATURE                Location/Qualifiers
misc_feature           1..55
                       note = Synthetic: trxA_adhE2Caopt_R
source                 1..55
                       mol_type = other DNA
                       organism = synthetic construct
SEQUENCE: 72
cgttcagttt ctgtttcagc tcttttgat tggtcacttt cgccaggtta gcgtc          55

SEQ ID NO: 73          moltype = DNA   length = 60
FEATURE                Location/Qualifiers
misc_feature           1..60
                       note = Synthetic: EtOH_F
source                 1..60
                       mol_type = other DNA
                       organism = synthetic construct
SEQUENCE: 73
ggcagcagcc atcaccatca tcaccacagc caggatccga tgagttatac tgtcggtacc    60

SEQ ID NO: 74          moltype = DNA   length = 60
FEATURE                Location/Qualifiers
misc_feature           1..60
                       note = Synthetic: EtOH_R
source                 1..60
                       mol_type = other DNA
                       organism = synthetic construct
```

```
SEQUENCE: 74
cgcatcatac aaaaccagca caattttcat tatatctcct tttagaaagc gctcaggaag    60

SEQ ID NO: 75           moltype = DNA   length = 46
FEATURE                 Location/Qualifiers
misc_feature            1..46
                        note = Synthetic: fdhCbopt_F
source                  1..46
                        mol_type = other DNA
                        organism = synthetic construct
SEQUENCE: 75
atgaaaattg tgctggtttt gtaatgaaaa ttgtgctggt tttgta                  46

SEQ ID NO: 76           moltype = DNA   length = 60
FEATURE                 Location/Qualifiers
misc_feature            1..60
                        note = Synthetic: MCS1_MCS2 linker_R
source                  1..60
                        mol_type = other DNA
                        organism = synthetic construct
SEQUENCE: 76
ggaatttata ctgacctcaa ttttctccat catatgtata tctccttctt atacttaact    60

SEQ ID NO: 77           moltype = DNA   length = 54
FEATURE                 Location/Qualifiers
misc_feature            1..54
                        note = Synthetic: SAATFa_F
source                  1..54
                        mol_type = other DNA
                        organism = synthetic construct
SEQUENCE: 77
agtaagtat aagaaggaga tatacatatg atggagaaaa ttgaggtcag tata           54

SEQ ID NO: 78           moltype = DNA   length = 60
FEATURE                 Location/Qualifiers
misc_feature            1..60
                        note = Synthetic: SAATFa_R
source                  1..60
                        mol_type = other DNA
                        organism = synthetic construct
SEQUENCE: 78
aaatttcgca gcagcggttt ctttaccaga ctcgagttaa attaaggtct ttggagatgc    60

SEQ ID NO: 79           moltype = DNA   length = 42
FEATURE                 Location/Qualifiers
misc_feature            1..42
                        note = Synthetic: BB_trxA_adhE2Caopt_F
source                  1..42
                        mol_type = other DNA
                        organism = synthetic construct
SEQUENCE: 79
atgtatatct ccttcttata cttaactaat atactaagat gg                      42

SEQ ID NO: 80           moltype = DNA   length = 60
FEATURE                 Location/Qualifiers
misc_feature            1..60
                        note = Synthetic: SAATFa_F
source                  1..60
                        mol_type = other DNA
                        organism = synthetic construct
SEQUENCE: 80
tagaaataat tttgtttaac tttaagaagg agatatagat atggagaaaa ttgaggtcag    60

SEQ ID NO: 81           moltype = DNA   length = 60
FEATURE                 Location/Qualifiers
misc_feature            1..60
                        note = Synthetic: SAATFa_R
source                  1..60
                        mol_type = other DNA
                        organism = synthetic construct
SEQUENCE: 81
gttagcagcc ggatctcagt ggtggtggtg gtggtggata attaaggtct ttggagatgc    60

SEQ ID NO: 82           moltype = DNA   length = 37
FEATURE                 Location/Qualifiers
misc_feature            1..37
                        note = Synthetic: univ_F
source                  1..37
                        mol_type = other DNA
```

```
                            organism = synthetic construct
SEQUENCE: 82
cctctagaaa taattttgtt taactttaag aaggaga                                37

SEQ ID NO: 83           moltype = DNA  length = 20
FEATURE                 Location/Qualifiers
misc_feature            1..20
                        note = Synthetic: univ_R
source                  1..20
                        mol_type = other DNA
                        organism = synthetic construct
SEQUENCE: 83
cggatctcag tggtggtggt                                                   20

SEQ ID NO: 84           moltype = DNA  length = 60
FEATURE                 Location/Qualifiers
misc_feature            1..60
                        note = Synthetic: malE_ATF1Sc_F
source                  1..60
                        mol_type = other DNA
                        organism = synthetic construct
SEQUENCE: 84
tttgtttaac tttaagaagg agatatagat atgaaaatcg aagaaggtaa actggtaatc       60

SEQ ID NO: 85           moltype = DNA  length = 60
FEATURE                 Location/Qualifiers
misc_feature            1..60
                        note = Synthetic: malE_ATF1Sc_R
source                  1..60
                        mol_type = other DNA
                        organism = synthetic construct
SEQUENCE: 85
cttgttgcac gggggcctga ttttctcat cgatttcatt cttggtgata cgagtctgcg        60

SEQ ID NO: 86           moltype = DNA  length = 26
FEATURE                 Location/Qualifiers
misc_feature            1..26
                        note = Synthetic: BB_pET29 ATF1Sc_F
source                  1..26
                        mol_type = other DNA
                        organism = synthetic construct
SEQUENCE: 86
aatgaaatcg atgagaaaaa tcaggc                                            26

SEQ ID NO: 87           moltype = DNA  length = 60
FEATURE                 Location/Qualifiers
misc_feature            1..60
                        note = Synthetic: nusA_ATF1Sc_F
source                  1..60
                        mol_type = other DNA
                        organism = synthetic construct
SEQUENCE: 87
attttgttta actttaagaa ggagatatag atatgaacaa agaaattttg gctgtagttg       60

SEQ ID NO: 88           moltype = DNA  length = 60
FEATURE                 Location/Qualifiers
misc_feature            1..60
                        note = Synthetic: nusA_ATF1Sc_R
source                  1..60
                        mol_type = other DNA
                        organism = synthetic construct
SEQUENCE: 88
attcttgttg cacgggggcc tgattttct catcgatttc attcgcttcg tcaccgaacc        60

SEQ ID NO: 89           moltype = DNA  length = 60
FEATURE                 Location/Qualifiers
misc_feature            1..60
                        note = Synthetic: trxA_ATF1Sc_F
source                  1..60
                        mol_type = other DNA
                        organism = synthetic construct
SEQUENCE: 89
attttgttta actttaagaa ggagatatag atatgagcga taaaattatt cacctgactg       60

SEQ ID NO: 90           moltype = DNA  length = 60
FEATURE                 Location/Qualifiers
misc_feature            1..60
                        note = Synthetic: trxA_ATF1Sc_R
source                  1..60
```

```
                              mol_type = other DNA
                              organism = synthetic construct
SEQUENCE: 90
cattcttgtt gcacgggggc ctgattttc tcatcgattt cattcgccag gttagcgtcg    60

SEQ ID NO: 91            moltype = DNA   length = 60
FEATURE                  Location/Qualifiers
misc_feature             1..60
                         note = Synthetic: malE_ATF1Sc_R
source                   1..60
                         mol_type = other DNA
                         organism = synthetic construct
SEQUENCE: 91
tgatggtgtg tttggaattt atactgacct caattttctc cttggtgata cgagtctgcg    60

SEQ ID NO: 92            moltype = DNA   length = 31
FEATURE                  Location/Qualifiers
misc_feature             1..31
                         note = Synthetic: BB_pET29_SAATFa_F
source                   1..31
                         mol_type = other DNA
                         organism = synthetic construct
SEQUENCE: 92
gagaaaattg aggtcagtat aaattccaaa c                                   31

SEQ ID NO: 93            moltype = DNA   length = 60
FEATURE                  Location/Qualifiers
misc_feature             1..60
                         note = Synthetic: nusA_ATF1Sc_R
source                   1..60
                         mol_type = other DNA
                         organism = synthetic construct
SEQUENCE: 93
gtttgatggt gtgtttggaa tttatactga cctcaatttt ctccgcttcg tcaccgaacc    60

SEQ ID NO: 94            moltype = DNA   length = 60
FEATURE                  Location/Qualifiers
misc_feature             1..60
                         note = Synthetic: trxA_ATF1Sc_R
source                   1..60
                         mol_type = other DNA
                         organism = synthetic construct
SEQUENCE: 94
ggtttgatgg tgtgtttgga atttatactg acctcaatttt tctccgccag gttagcgtcg    60

SEQ ID NO: 95            moltype = DNA   length = 60
FEATURE                  Location/Qualifiers
misc_feature             1..60
                         note = Synthetic: AmpR_F
source                   1..60
                         mol_type = other DNA
                         organism = synthetic construct
SEQUENCE: 95
attagttaag tataagaagg agatatacat atgatgaacg aaatcgacga aaaaaatcag    60

SEQ ID NO: 96            moltype = DNA   length = 60
FEATURE                  Location/Qualifiers
misc_feature             1..60
                         note = Synthetic: AmpR_R
source                   1..60
                         mol_type = other DNA
                         organism = synthetic construct
SEQUENCE: 96
tttcgcagca gcggtttctt taccagactc gagcggaccc agtaacaaag ctttatatat    60

SEQ ID NO: 97            moltype = AA   length = 25
FEATURE                  Location/Qualifiers
REGION                   1..25
                         note = Synthetic: maltose binding protein without the
                         N-terminus signal sequence
source                   1..25
                         mol_type = protein
                         organism = synthetic construct
SEQUENCE: 97
KIKTGARILA LSALTTMMFS ASALA                                          25

SEQ ID NO: 98            moltype = DNA   length = 22
FEATURE                  Location/Qualifiers
misc_feature             1..22
```

```
                        note = Synthetic: MCS1_MCS2 linker_F
source                  1..22
                        mol_type = other DNA
                        organism = synthetic construct
SEQUENCE: 98
aaaataagaa ttcgagctcg gc                                         22
```